US007968560B2

(12) United States Patent
Clary et al.

(10) Patent No.: US 7,968,560 B2
(45) Date of Patent: Jun. 28, 2011

(54) COMPOUNDS THAT MODULATE PPARγ-TYPE RECEPTORS AND COSMETIC/PHARMACEUTICAL COMPOSITIONS COMPRISING SAID COMPOUNDS

(75) Inventors: Laurence Clary, La Colle sur Loop (FR); Etienne Thoreau, Saint Vallier de Thiey (FR); Michel Rivier, Nice (FR); Jerome Aubert, Grasse (FR); Laurent Chantalat, Grasse (FR); Johannes Voegel, Chateauneuf/Grasse (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 12/585,634

(22) Filed: Sep. 21, 2009

(65) Prior Publication Data

US 2010/0247468 A1     Sep. 30, 2010

Related U.S. Application Data

(63) Continuation of application No. 11/311,449, filed on Dec. 20, 2005, now Pat. No. 7,625,914, which is a continuation of application No. PCT/EP2004/007200, filed on Jun. 16, 2004.

(60) Provisional application No. 60/489,672, filed on Jul. 24, 2003.

(30) Foreign Application Priority Data

Jun. 20, 2003   (FR) ..................... 03 07487

(51) Int. Cl.
| A61K 31/505 | (2006.01) |
| A61K 31/445 | (2006.01) |
| A61K 31/44  | (2006.01) |
| A61K 31/41  | (2006.01) |
| A61K 31/425 | (2006.01) |
| A61K 31/415 | (2006.01) |
| A61K 31/38  | (2006.01) |
| A61K 31/34  | (2006.01) |
| C07D 239/02 | (2006.01) |
| C07D 211/06 | (2006.01) |
| C07D 213/00 | (2006.01) |
| C07D 285/10 | (2006.01) |
| C07D 277/20 | (2006.01) |
| C07D 249/14 | (2006.01) |
| C07D 233/28 | (2006.01) |
| C07D 333/36 | (2006.01) |
| C07D 307/02 | (2006.01) |

(52) U.S. Cl. ........ 514/275; 514/317; 514/332; 514/361; 514/370; 514/383; 514/396; 514/447; 514/461; 544/330; 546/194; 546/309; 548/134; 548/146; 548/262.6; 548/328.1; 549/63; 549/480

(58) Field of Classification Search .............. 514/275, 514/317, 332, 361, 370, 383, 396, 447, 461; 544/330; 546/194, 309; 548/134, 146, 262.6, 548/328.1; 549/63, 480
See application file for complete search history.

(56) References Cited

U.S. PATENT DOCUMENTS

| 6,699,904 B2 * | 3/2004 | Hayward et al. ............. 514/535 |
| 6,927,228 B2 | 8/2005 | Bernardon et al. |

FOREIGN PATENT DOCUMENTS

| EP | 1 216 980 | 6/2002 |
| WO | WO 02/12210 A1 | 2/2002 |
| WO | WO 2004/024939 A2 | 3/2004 |

OTHER PUBLICATIONS

M.M.T. Downie et al., "Peroxisome proliferator-activated receptor and farnesoid X receptor ligands differentially regulate sebaceous differentiation in human sebaceous gland organ cultures in vitro", British Journal of Dermatology, 2004: 151: 766-775, published by Blackwell Publishing, UK.
Ramona Behshad et al., "A Retrospective Case Series Review of the Peroxisome Proliferator-Activated Receptor Ligand Rosiglitazone in the Treatment of Atopic Dermatitis," Arch Dermatol. 2008; 144(1):84-88, published by AMA, Chicago, IL, US.
Tamar Nijsten et al., "Peroxisome proliferator-activated receptors in squamous cell carcinoma and its precursors," Journal of Cutaneous Pathology, 2005: 32:340-347, published by Blackwell Munksgaard, Denmark.
Joong Sun Lee et al., "PPAR-gamma agonist, ciglitazone, increases pigmentation and migration of human melanocytes," Experimental Dermatology, 2007, 16, 118-123, published by Blackwell Munksgaard, Denmark.
James Varani et al. "Thiazolidinediones: potential as therapeutics for psoriasis and perhaps other hyperproliferative skin disease," Expert Opin. Investig. Drugs, 2006, 15(11):1453-1468, published by Informa HealthCare, UK.
George Patani et al., "Bioisosterism: A Rational Approach in Drug Design," Chem.Rev. 1996, vol. 96, No. 8, pp. 3147-3176, American Chemical Society, US.

* cited by examiner

*Primary Examiner* — Joseph Kosack
(74) *Attorney, Agent, or Firm* — Buchanan Ingersoll & Rooney, P.C.

(57) ABSTRACT

Novel compounds having the general formula (I) below:

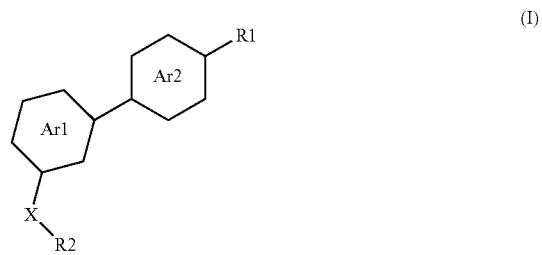

are useful in a wide variety of applications in human or veterinary medicine (in dermatology, and also in the fields of cardiovascular diseases, immune diseases and/or diseases associated with lipid metabolism), or, alternatively are formulated into cosmetic compositions.

31 Claims, 21 Drawing Sheets

18

R''' = NR14G or CH₂NR14G

Y = O, N, S

COMPOUNDS THAT MODULATE PPARγ-TYPE RECEPTORS AND COSMETIC/PHARMACEUTICAL COMPOSITIONS COMPRISING SAID COMPOUNDS

CROSS-REFERENCE TO EARLIER APPLICATIONS

This application is a continuation of U.S. patent application Ser. No. 11/311,449, filed Dec. 20, 2005 now U.S. Pat. No. 7,625,914, now allowed, which is a continuation of PCT/EP2004/007200 filed Jun. 16, 2004 and designating the United States, published on Dec. 29, 2004 as WO 2004/113331 A1, which claims the benefit of U.S. Provisional Application No. 60/489,672, filed Jul. 24, 2003, and the foreign priority of FR03/07487, filed Jun. 20, 2003, each earlier application hereby expressly incorporated by reference and each assigned to the assignee hereof.

BACKGROUND OF THE INVENTION

1. Technical Field of the Invention

The present invention relates to, as novel and useful industrial products, a novel class of compounds that are modulators of receptors of Peroxisome Proliferator-Activated Receptor type of subtype γ (PPARγ). The present invention also relates to a process for preparing such novel compounds and to their formulation into pharmaceutical compositions suited for administration in human or veterinary medicine, or, alternatively formulated into cosmetic compositions.

2. Description of Background and/or Related and/or Prior Art

The activity of receptors of PPAR type has been the subject of many studies. Mention may be made, as a guide, of the publication entitled "Differential Expression of Peroxisome Proliferator-Activated Receptor Subtypes During the Differentiation of Human Keratinocytes", Michel Rivier et al., *J. Invest. Dermatol.*, 111, 1998, pp. 1116-1121, in which is listed a large number of bibliographic references relating to receptors of PPAR type. Mention may also be made, as a guide, of the report entitled "The PPARs: From orphan receptors to Drug Discovery", Timothy M. Willson, Peter J. Brown, Daniel D. Sternbach and Brad R. Henke, *J. Med. Chem.*, 2000, Vol. 43, pp. 527-550.

PPAR receptors activate transcription by binding to elements of DNA sequences, known as peroxisome proliferator response elements (PPRE), in the form of a heterodimer with retinoid X receptors (known as RXRs).

Three subtypes of human PPARs have been identified and described: PPARα, PPARγ and PPARδ (or NUC1).

PPARα is mainly expressed in the liver, while PPARδ is ubiquitous.

PPARγ is the most extensively studied of the three subtypes. All the references suggest a critical role of PPARγ in regulating the differentiation of adipocytes, where it is greatly expressed. It also has a key role in systemic lipid homeostasis.

It has been described in particular in patent application WO 96/33724 that PPARγ-selective compounds, such as a prostaglandin-J2 or -D2, are potential active agents for treating obesity and diabetes.

Moreover, the assignee hereof has already described PPARγ compounds and/or the use thereof in FR-2,773,075, which describes the use of PPARγ activator compounds in the preparation of a pharmaceutical composition, the composition being intended to treat skin disorders associated with an anomaly of epidermal cell differentiation.

SUMMARY OF THE INVENTION

The present invention features a novel class of PPARγ-modulating compounds that show very good specific affinity for PPARγ.

Thus, the present invention features compounds having the general formula (I) below:

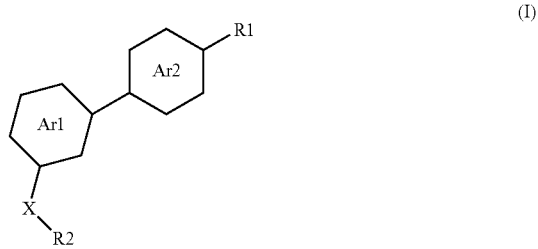

in which:

R1 is a radical of formula (a) or (b) below:

(a)

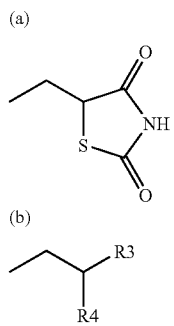

(b)

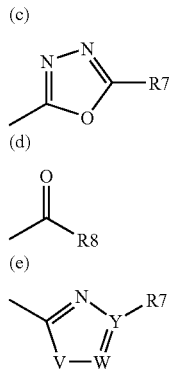

R3 and R4 are as defined below;

R2 is an alkyl radical having from 1 to 12 carbon atoms, an aryl radical, an aralkyl radical, a heteroaryl radical, a heterocyclic radical, a 9-fluorenylmethyl radical or a radical of formula $(CH_2)_m(NR5)_m(C(O,N)_pR6$;

R5, R6, m, n and p are as defined below;

R3 is a radical selected from among the following formulae:

(c)

$$\underset{\text{N}}{\overset{\text{N}-\text{N}}{\Big\langle}}\underset{\text{O}}{\Big\rangle}-R7$$

(d)

$$\underset{}{\overset{\text{O}}{\|}}\underset{}{\text{—}}R8$$

(e)

$$\underset{V-W}{\overset{N}{\diagdown}}\underset{}{Y}\text{—}R7$$

R7, R8, V, W and Y are as defined below;

R4 is an alkyl radical having from 1 to 12 carbon atoms, a radical OR9 or a radical SR9 or NHR9;

R5 and R7, which may be identical or different, are each a hydrogen atom, an alkyl radical having from 1 to 12 carbon atoms, an aryl radical, an aralkyl radical, a heteroaryl radical or a heterocyclic radical, with the proviso that when Y is an nitrogen atom, then formula (e) is not substituted by a radical R7;

R6 and R8, which may be identical or different, are each:
a radical O—(CH$_2$)$_v$—R10,
a hydroxyl radical, an alkyl radical having from 1 to 12 carbon atoms, an aryl radical, an aralkyl radical, a heteroaryl radical, a heterocyclic radical,
a radical

or a radical NR'(CH$_2$)$_v$R10;
R10, R', R" and v are as defined below;
R9 is an alkyl radical having from 1 to 12 carbon atoms, or a radical selected from among those of the following formulae:

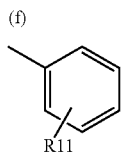

(f)

(g) —CO-(Q)$_p$-R11; and
(h) α-amino acid N-protected with standard amine-protecting groups, such as 9-fluorenylmethylcarbamate (FMOC), t-butylcarbamate (BOC), benzyl or trifluoroacetyl;
R11, Q and p are as defined below;
m has the values 0, 1 or 2;
n and p have the values 0 or 1;
Q is an oxygen or sulfur atom or NR5;
V is an oxygen, a nitrogen or sulfur atom;
W is a nitrogen atom or a radical C—R5;
Y is a nitrogen atom or a carbon atom;
Z is an oxygen, nitrogen or sulfur atom;
v has the values 1, 2 or 3;
R10 is an alkyl radical having from 1 to 12 carbon atoms, an aryl, aralkyl, heteroaryl or heterocyclic radical, a radical NH—CO—R12, a radical NH—CO—O—R12 or C—R12R13 or a radical N—R12R13, wherein R12 and R13 are as defined below;
R' is a hydrogen atom, an alkyl radical having from 1 to 12 carbon atoms, a heteroaryl radical or a heterocyclic radical;
R" is a hydrogen atom, an alkyl radical having from 1 to 12 carbon atoms, an aryl radical, an aralkyl radical, optionally substituted with one or more halogens, a heteroaryl radical, a heterocyclic radical, a radical (CH$_2$)$_v$—R10, or a radical NHR$_{10}$ or NR10R10;
R11 is a hydrogen atom, an alkyl radical having from 1 to 12 carbon atoms, an aryl radical, an aralkyl radical, a heteroaryl radical, a heterocyclic radical or a radical (CO)$_s$(Z)$_t$R10 with s and t having the values 0, 1 or 2;
R12 is a hydrogen atom, an alkyl radical having from 1 to 12 carbon atoms, an aryl radical, an aralkyl radical, a heteroaryl radical or a heterocyclic radical;
R13 is a hydrogen atom or an alkyl radical having from 1 to 12 carbon atoms;

X is a radical having the following structure:

—(CH$_2$)$_z$—NR14-C(T)-(D)$_w$- wherein D, z, T and R14 are as defined below;
T is an oxygen or sulfur atom;
D is an oxygen or sulfur atom, a radical —NR15 or a radical CH$_2$, wherein R15 is as defined below;
z has the values 0 or 1;
w has the values from 0 to 6; and
R14 and R15 are each a hydrogen atom or an alkyl radical having from 1 to 12 carbon atoms, Ar1 and Ar2, which may be identical or different, are each an optionally substituted aromatic radical of one of the formulae:

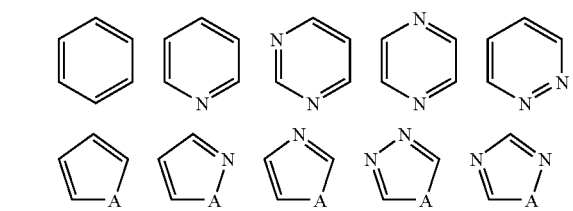

wherein A is an S or O atom or a radical N—R13, with the proviso that, when Ar1 or Ar2 is a phenyl radical, then Ar2 or Ar1 is necessarily a heteroaryl radical, and the optical and geometrical isomers and also the salts thereof.

When the compounds according to the invention are in the form of a carboxylic acid salt, the said salt is preferably an alkali metal salt, in particular the sodium salt, an alkaline-earth metal salt or a salt of an organic amine, more particularly of amino acids such as arginine or lysine.

When the compounds according to the invention are in the form of a salt of an amine function, for example of a pyridine, the said salt is preferably a salt of a halogen atom, such as the hydrochloride or the hydrobromide, or an organic acid salt, such as a fumarate or a maleate, or a nitrate.

Figure 1A:
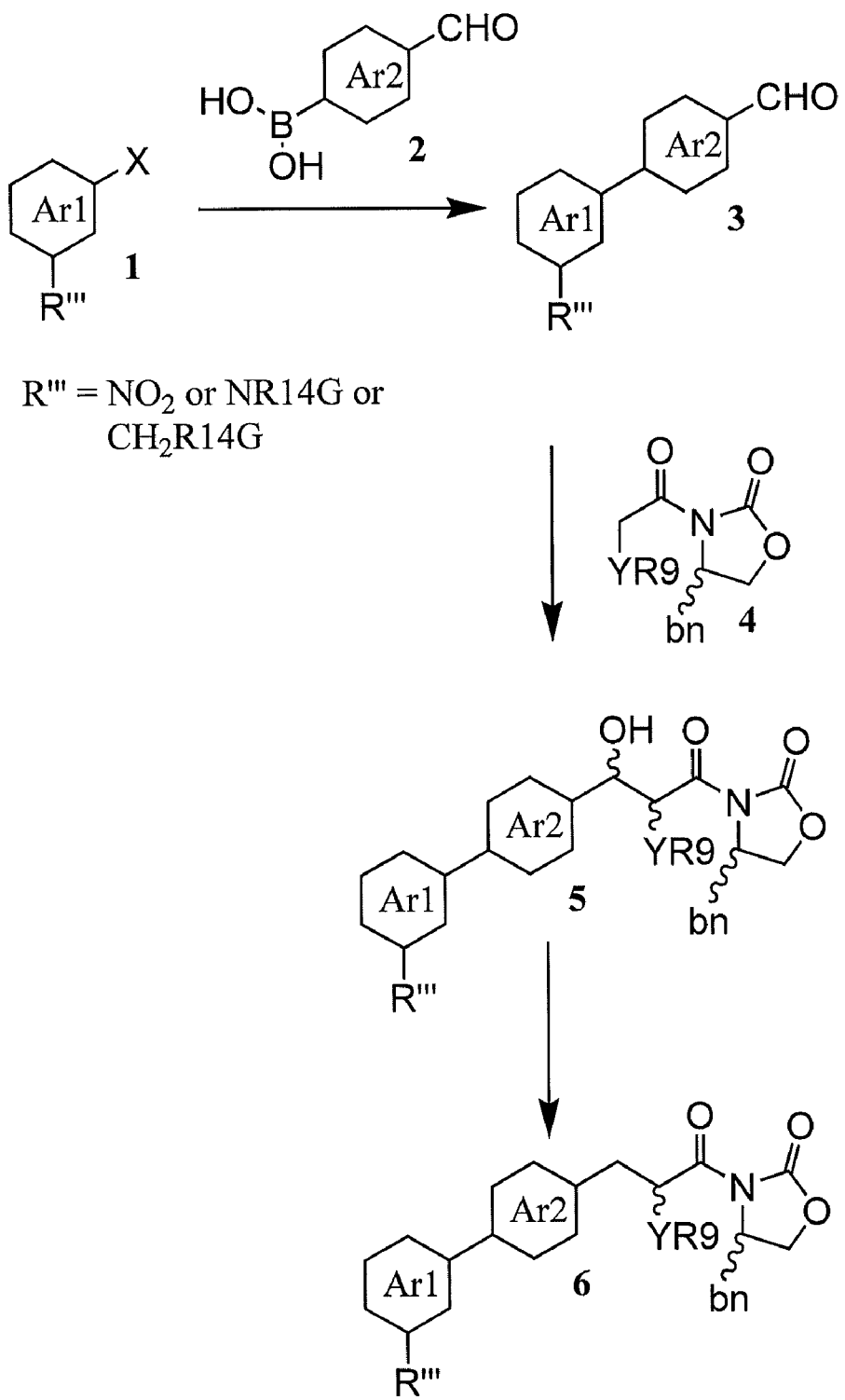
FIGS. 1A, 1B, 1C and 1D describe a reaction scheme for preparing compounds of formula (I) with R1 having formula (b) such as compounds of formulas 12 to 16.
Figure 1B:
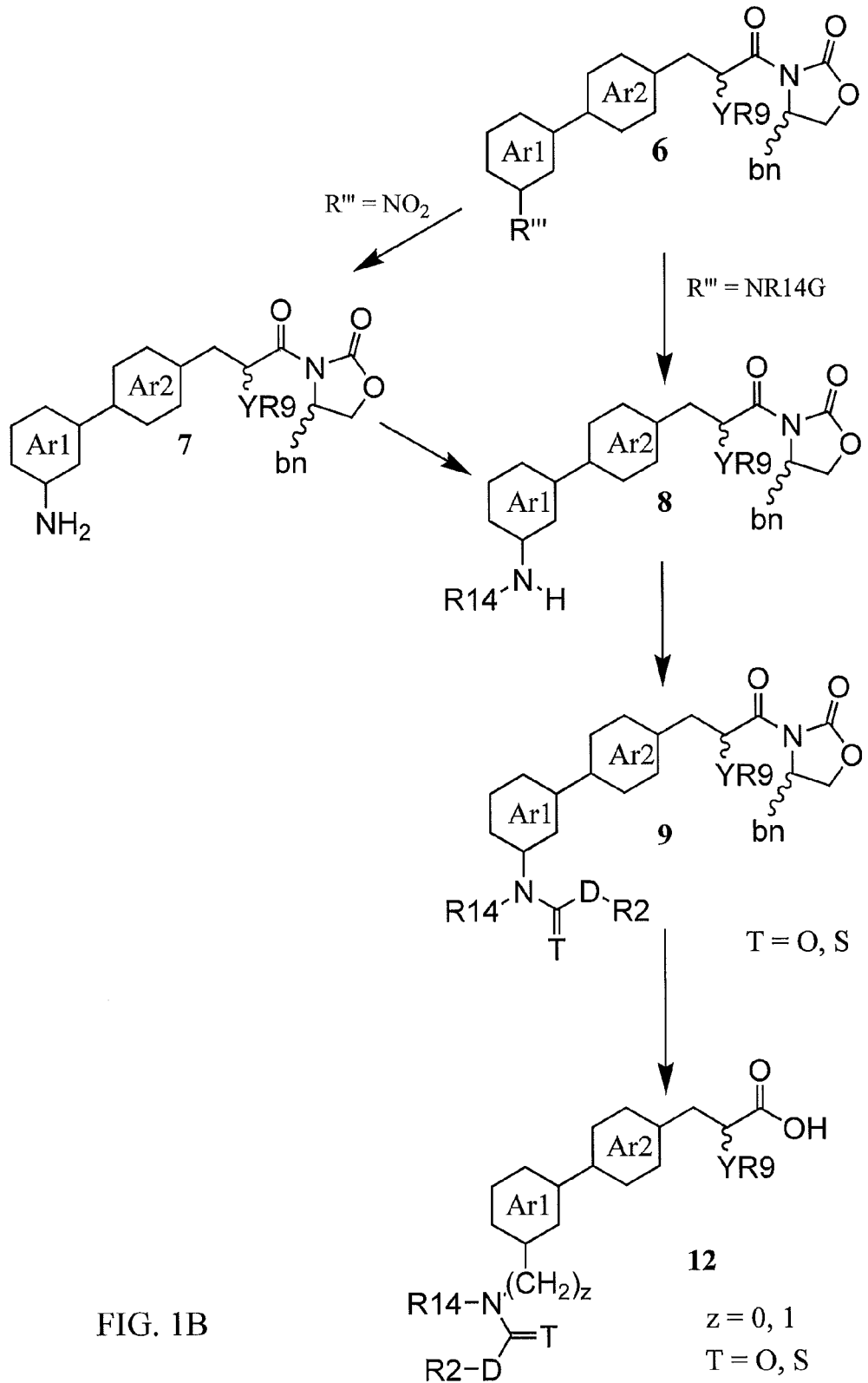
Figure 1C:
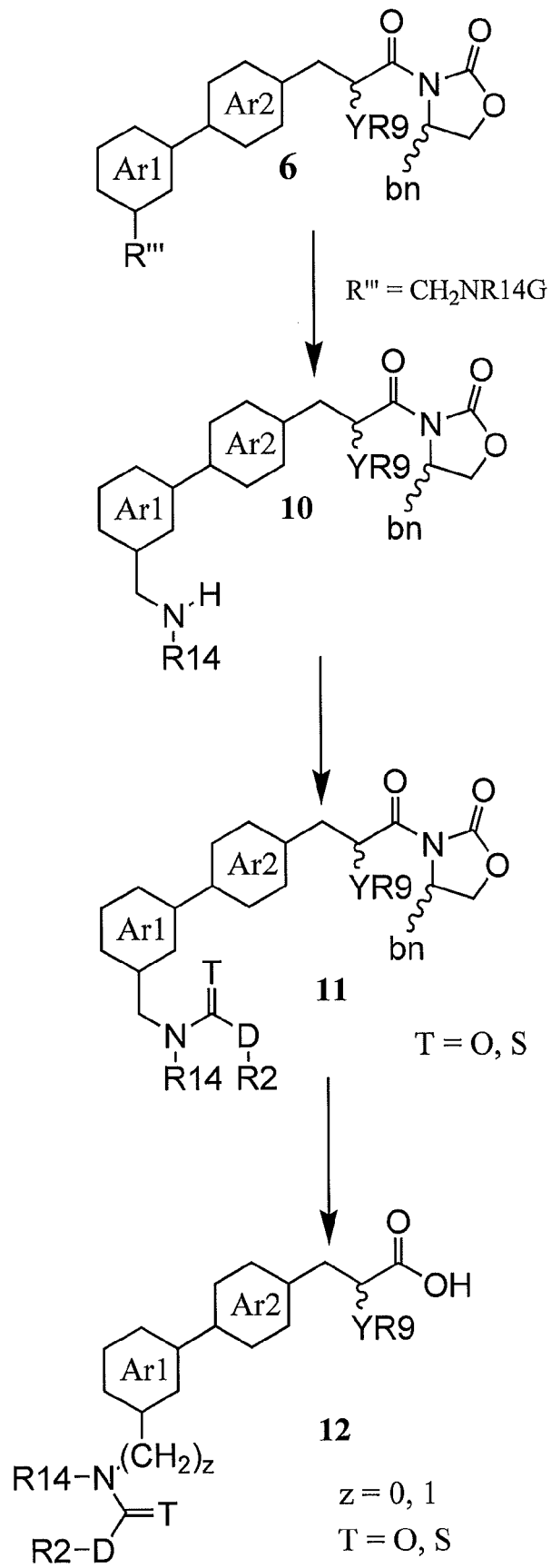
Figure 1D:
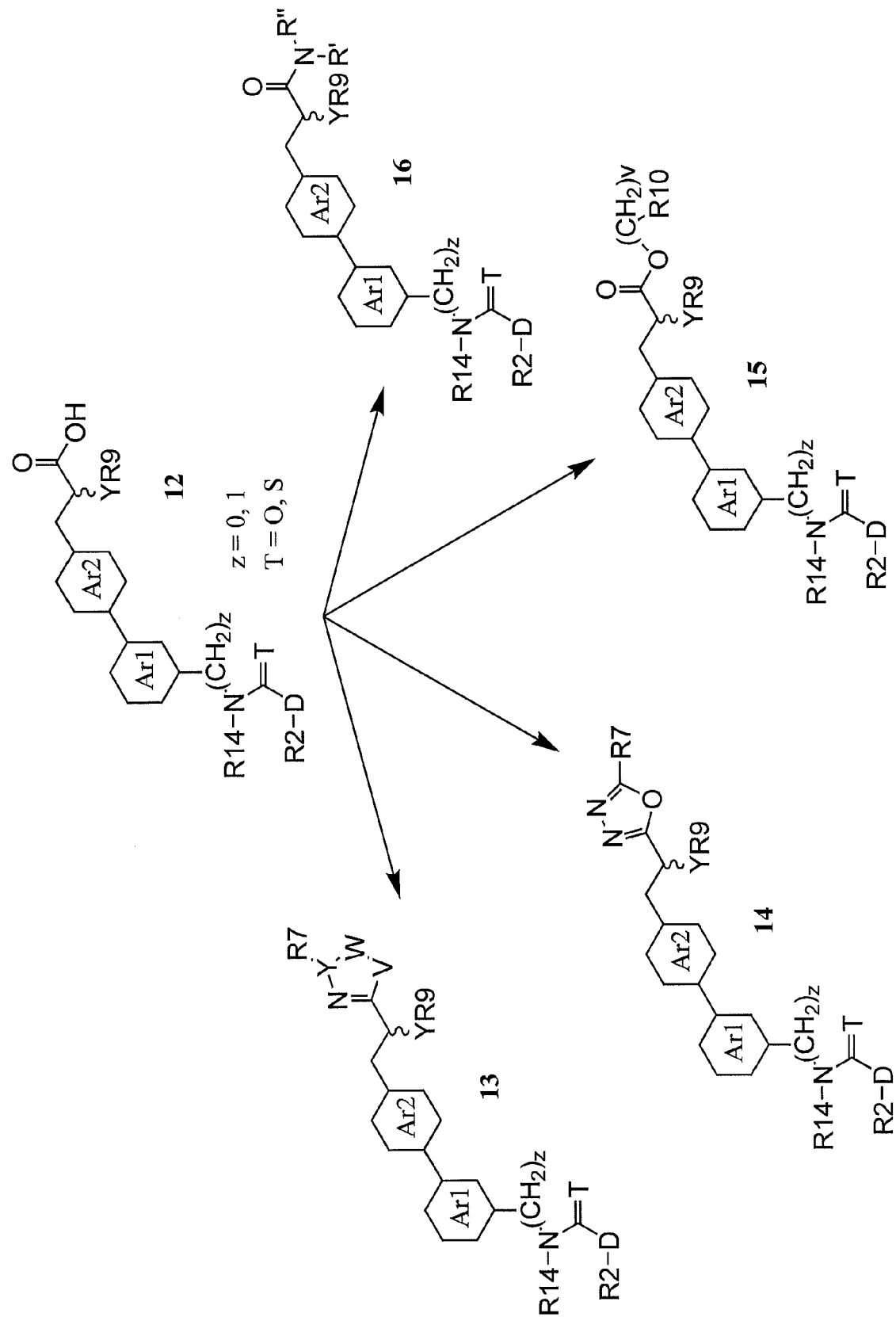
Figure 2A:
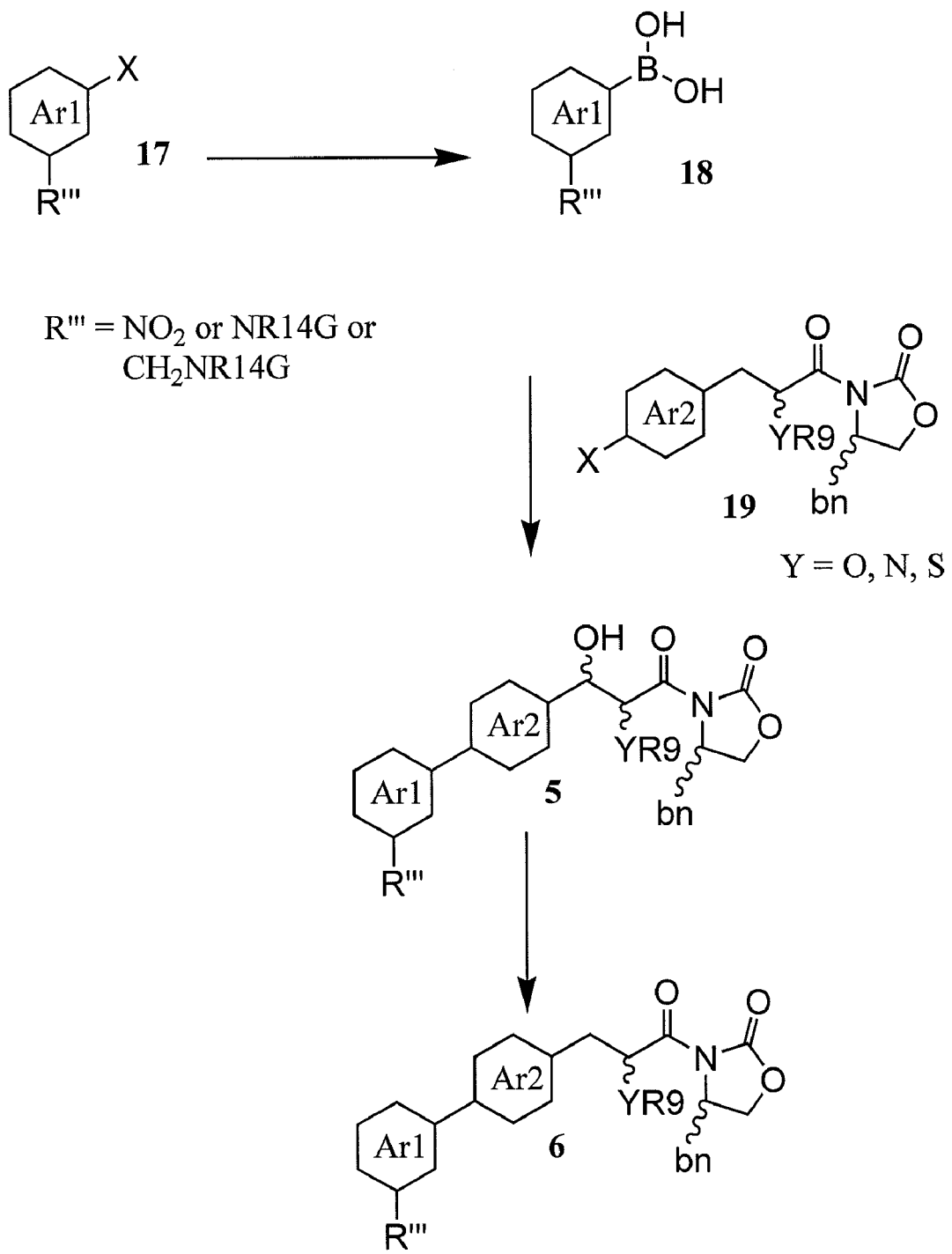
FIGS. 2A, 2B, 2C and 2D describe another reaction route for obtaining compounds of formulas 12 to 16.
Figure 2B:
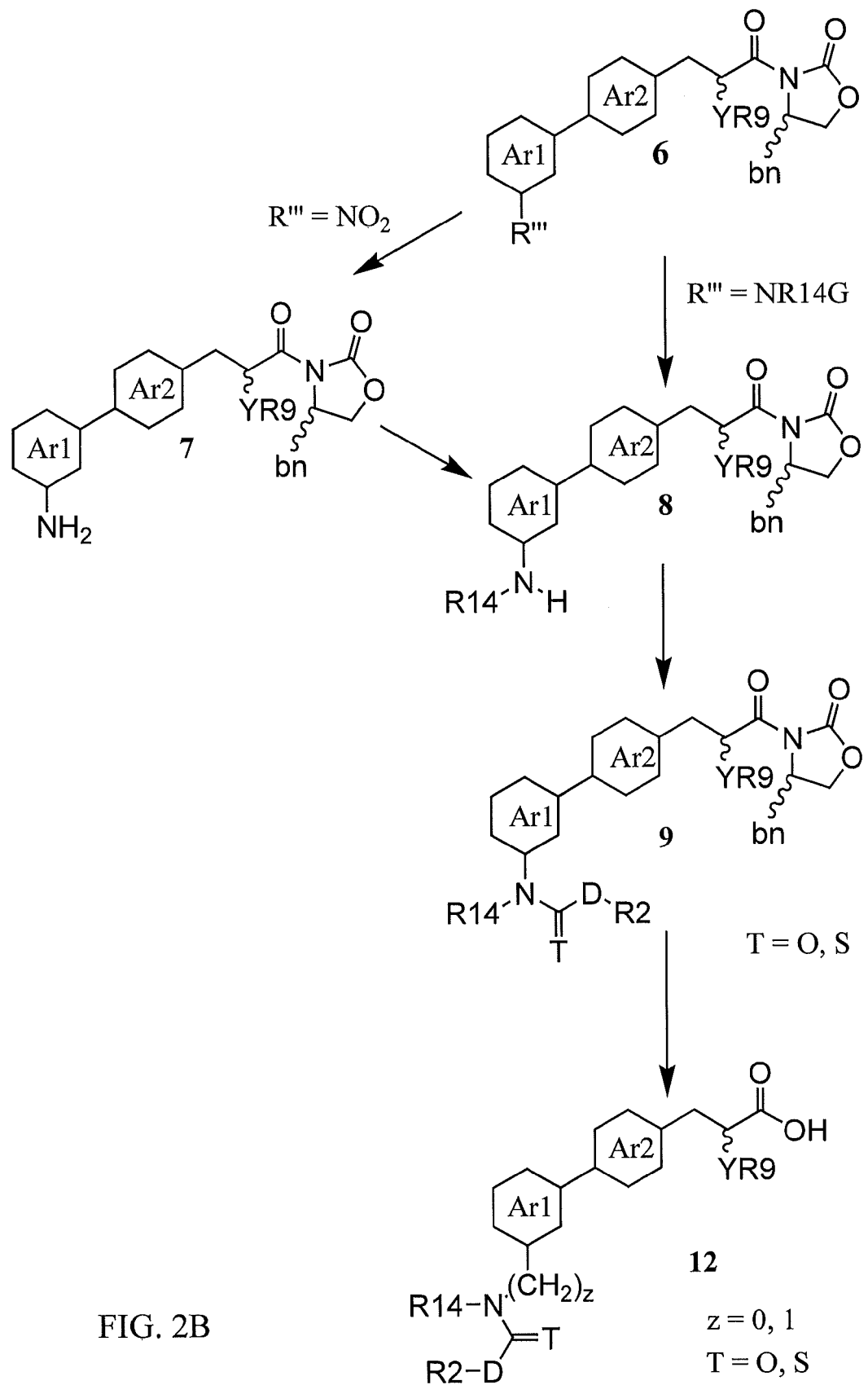
Figure 2C:
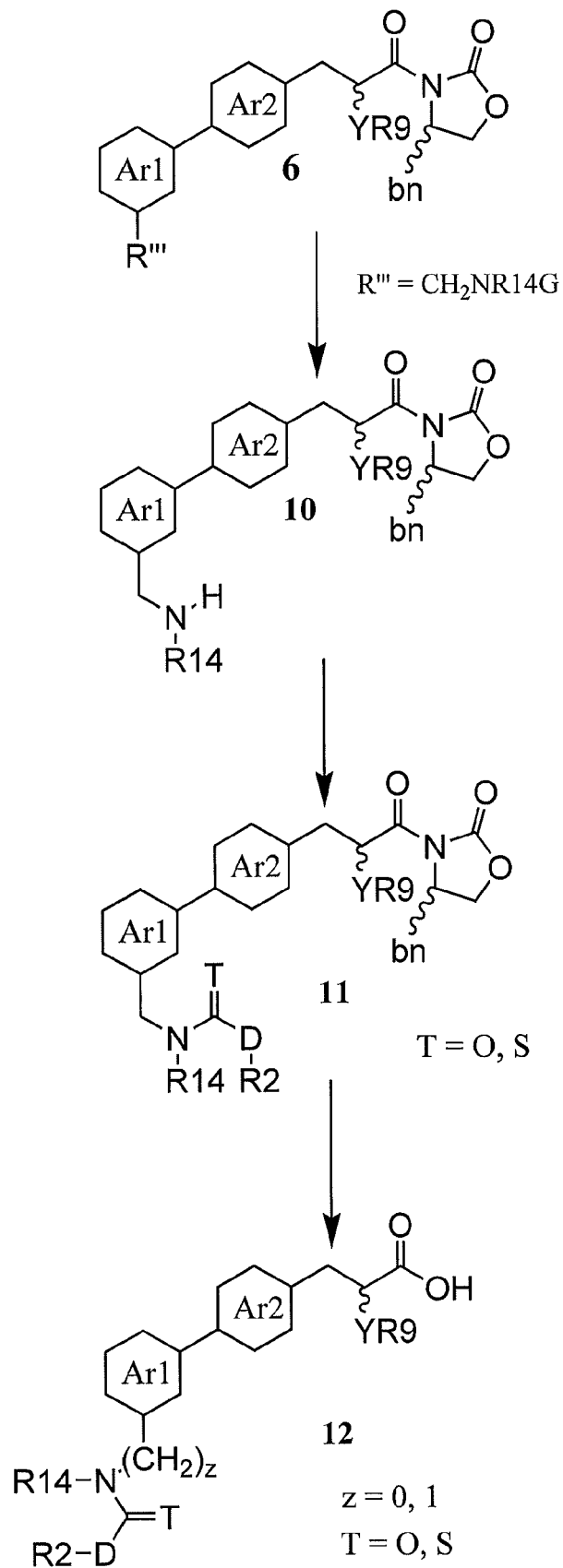
Figure 2D:
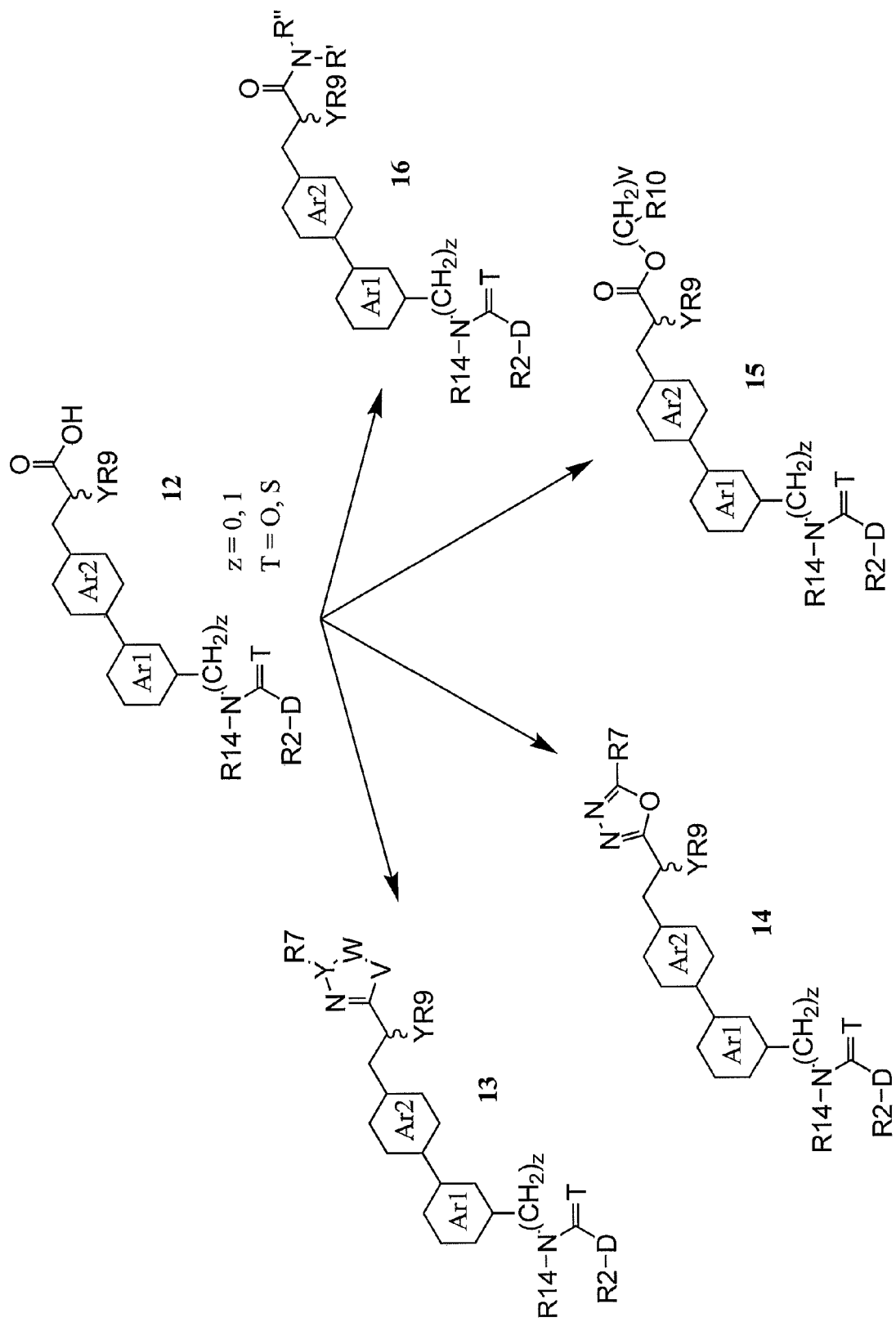

DETAILED DESCRIPTION OF BEST MODE AND SPECIFIC/PREFERRED EMBODIMENTS OF THE INVENTION

According to the present invention, the term "hydroxyl radical" means the —OH radical.

According to the present invention, the expression "alkyl radical having from 1 to 12 carbon atoms" means a linear or cyclic, saturated or unsaturated, optionally branched, hydrogen-containing or fluorine-containing radical having 1 to 12 carbon atoms, which may be interrupted with a hetero atom, and the alkyl radicals having from 1 to 12 carbon atoms are preferably methyl, ethyl, isopropyl, butyl, tert-butyl, hexyl, heptyl, octyl, decyl, cyclohexyl or methylenecyclopropyl radicals.

The term "polyether radical" means a polyether radical having from 1 to 6 carbon atoms interrupted with at least one oxygen atom, such as methoxymethoxy, ethoxymethoxy or methoxyethoxymethoxy radicals.

The term "halogen atom" means a fluorine, chlorine or bromine atom.

The term "alkoxy radical having from 1 to 7 carbon atoms" means a methoxy, ethoxy, isopropyloxy, tert-butoxy, hexyloxy, heptyloxy, benzyloxy or phenoxy radical, which may optionally be substituted with an alkyl radical having from 1 to 12 carbon atoms.

The term "aryl radical" means a phenyl, biphenyl, cinnamyl or naphthyl radical, which may be mono- or disubstituted with a halogen atom, a $CF_3$ radical, an alkyl radical having from 1 to 12 carbon atoms, an alkoxy radical having from 1 to 7 carbon atoms, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl having from 1 to 12 carbon atoms.

The term "aralkyl radical" means a benzyl, phenethyl or 2-naphthylmethyl radical, which may be mono- or disubstituted with a halogen atom, a $CF_3$ radical, an alkyl radical having from 1 to 12 carbon atoms, an alkoxy radical having from 1 to 7 carbon atoms, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl having from 1 to 12 carbon atoms.

The term "heteroaryl radical" means an aryl radical interrupted with one or more hetero atoms, such as a pyridyl, furyl, thienyl, isoxazolyl, oxadiazolyl, oxazolyl, isothiazolyl, quinazolinyl, benzothiadiazolyl, benzimidazolyl, quinoxalyl, indolyl or benzofuryl radical, optionally substituted with at least one halogen, an alkyl having from 1 to 12 carbon atoms, an alkoxy having from 1 to 7 carbon atoms, an aryl radical, a nitro function, a polyether radical, a heteroaryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl having from 1 to 12 carbon atoms.

The term "heterocyclic radical" preferably means a morpholino, piperidino, piperazino, 2-oxo-1-piperidyl or 2-oxo-1-pyrrolidinyl radical, optionally substituted with at least one alkyl having from 1 to 12 carbon atoms, an alkoxy having from 1 to 7 carbon atoms, an aryl radical, a nitro function, a polyether radical, a heteroaryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl having from 1 to 12 carbon atoms.

Among the compounds of formula (I) above according to the present invention, especially exemplary are the following compounds (alone or as a mixture):

1. N-{4-[4-(2,4-Dioxothiazolidin-5-ylmethyl)phenyl]thiophen-2-ylmethyl}-N-methylbenzamide,
2. N-{5-[4-(2,4-Dioxothiazolidin-5-ylmethyl)phenyl]thiophen-3-ylmethyl}-N-methylbenzamide,
3. N-{5-[4-(2,4-Dioxothiazolidin-5-ylmethyl)phenyl]pyrid-3-ylmethyl}-N-methylbenzamide,
4. N-{3-[5-(2,4-Dioxothiazolidin-5-ylmethyl)pyrid-2-yl]benzyl}-N-methyloctanoylamide,
5. 2(S)-Ethoxy-3-(4-{5-[(methyloctanoylamino)methyl]thiophen-3-yl}phenyl)propanoic acid,
6. 2(S)-Ethoxy-3-(4-{5-[(methyloctanoylamino)methyl]thiophen-2-yl}phenyl)propanoic acid,
7. 2(S)-Ethoxy-3-{4-[2-(3-heptyl-1-methylureido)thiazol-4-yl]phenyl}propanoic acid,
8. 2(S)-Ethoxy-3-{4-[2-(3-pentyl-1-methylureido)thiazol-5-yl]phenyl}propanoic acid,
9. 2(S)-Ethoxy-3-{4-[6-(3-heptyl-1-methylureido)pyrid-2-yl]phenyl}propanoic acid,
10. 2-[4-(2-Carboxy-2(S)-ethoxyethyl)phenyl]-6-(3-heptyl-1-methylureido)pyridinium chloride,
11. 2(S)-Ethoxy-3-{4-[5-(3-heptyl-1-methylureido)-2-methyl-2H-[1,2,4]triazol-3-yl]phenyl}propanoic acid,
12. {3-[5-(2,4-Dioxothiazolidin-5-ylmethyl)thiophen-2-yl]benzyl}methyloctanoylcarboxylamide,
13. {3-[5-(2,4-Dioxothiazolidin-5-ylmethyl)thiophen-2-yl]benzyl}methylhexanoylcarboxylamide,
14. 2(S)-(2-Benzoylphenylamino)-3-(4-{5-[(methyloctanoylamino)methyl]thiophen-3-yl}phenyl)propanoic acid,
15. 2(S)-(2-Benzoylphenylamino)-3-(4-{5-[(hexanoylmethylamino)methyl]thiophen-3-yl}phenyl)propanoic acid,
16. 2(S)-Ethoxy-3-(4-{5-[(hexanoylmethylamino)-methyl]thiophen-3-yl}phenyl)propanoic acid,
17. 2(S)-Ethoxy-3-(4-{5-[(methylpentanoylamino)methyl]thiophen-3-yl}phenyl)propanoic acid,
18. 3-[4-(5-{[(2-Cyclopentylacetyl)methylamino]methyl}thiophen-3-yl)phenyl]-2(S)-ethoxypropanoic acid,
19. 3-[4-(5-{[(3-Cyclohexylpropionyl)methylamino]methyl}thiophen-3-yl)phenyl]-2(S)-ethoxypropanoic acid,
20. 2-Ethoxy-3-{6-[3-(3-heptyl-1-methylureido)phenyl]pyrid-3-yl}propanoic acid,
21. 2(S)-(2-Benzoylphenylamino)-3-{4-[6-(1-methyl-3-pentylureido)pyrid-2-yl]phenyl}propanoic acid,
22. 2(S)-(2-Benzoylphenylamino)-3-{4-[6-(3-heptyl-1-methylureido)pyrid-2-yl]phenyl}propanoic acid,
23. 2(S)-Ethoxy-3-{6-[3-(3-heptyl-1-methylureido)phenyl]pyrid-3-yl}propanoic acid,
24. 2(S)-Ethoxy-3-{4-[6-(1-methyl-3-pentylureido)pyrid-2-yl]phenyl}propanoic acid hydrochloride,
25. 3-{4-[6-(3-Butyl-1-methylureido)pyrid-2-yl]phenyl}-2(S)-ethoxypropanoic acid,
26. 2(S)-Ethoxy-3-{4-[6-(1-methyl-3-phenethylureido)pyrid-2-yl]phenyl}propanoic acid hydrochloride,
27. 2(S)-Ethoxy-3-{4-[6-(1-methyl-3-phenylureido)pyrid-2-yl]phenyl}propanoic acid,
28. 2(S)-Ethoxy-3-{4-[6-(1-methyl-3-naphthalen-2-ylureido)pyrid-2-yl]phenyl}propanoic acid, 29. 3-{4-[6-(3-Cyclohexyl-1-methylureido)pyrid-2-yl]phenyl}-2(S)-ethoxypropanoic acid,
30. 2(S)-Ethoxy-3-{4-[3-(3-heptyl-1-methylureido)phenyl]thiazol-2-yl}propanoic acid,
31. 2(S)-Ethoxy-3-{4-[3-(1-methyl-3-pentylureido)phenyl]thiazol-2-yl}propanoic acid,
32. 2(S)-Ethoxy-3-{6-[3-(1-methyl-3-pentylureido)phenyl]pyrid-3-yl}propanoic acid,
33. 2(S)-Ethoxy-3-[4-(6-{3-[2-(4-fluorophenyl)ethyl]-1-methylureido}pyrid-2-yl)phenyl]propanoic acid,
34. 2(S)-Ethoxy-3-{4-[6-(1-methyl-3-pentylureido)pyrid-2-yl]phenyl}propanoic acid,
35. 2(S)-Ethoxy-3-{4-[4-(3-heptyl-1-methylureido)pyrid-2-yl]phenyl}propanoic acid,
36. 2(S)-Ethoxy-3-{4-[4-(1-methyl-3-pentylureido)pyrid-2-yl]phenyl}propanoic acid,
37. 2(S)-Ethoxy-3-{4-[2-(1-methyl-3-pentylureido)pyrid-4-yl]phenyl}propanoic acid,
38. 2(S)-Ethoxy-3-{4-[2-(3-heptyl-1-methylureido)pyrid-4-yl]phenyl}propanoic acid,
39. 2(S)-Ethoxy-3-{4-[2-(3-heptyl-1-methylureido)pyrimidin-4-yl]phenyl}propanoic acid,
40. 2(S)-Ethoxy-3-{4-[2-(1-methyl-3-pentylureido)pyrimidin-4-yl]phenyl}propanoic acid,
41. 2(S)-Ethoxy-3-{5-[3-(3-heptyl-1-methylureido)phenyl]furan-2-yl}propanoic acid,
42. 2(S)-Ethoxy-3-{5-[3-(3-heptyl-1-methylureido)phenyl]thiophen-2-yl}propanoic acid,
43. 2(S)-Ethoxy-3-{2-[3-(3-heptyl-1-methylureido)phenyl]pyrimidin-5-yl}propanoic acid,
44. 2(S)-Ethoxy-3-{6-[3-(3-heptyl-1-methylureido)phenyl]pyrid-3-yl}propanoic acid,
45. 2(S)-Ethoxy-3-{4-[5-(3-heptyl-1-methylureido)thiophen-2-yl]phenyl}propanoic acid,
46. 2(S)-Ethoxy-3-[4-(5-{[methyl(6-propoxynaphthalene-2-carbonyl)amino]methyl}furan-2-yl)phenyl]propanoic acid,
47. 2(S)-Ethoxy-3-{4-[5-(3-heptyl-1-methylureido)furan-2-yl]phenyl}propanoic acid,
48. 2(S)-Ethoxy-3-[4-(5-{[methyl(6-propoxynaphthalene-2-carbonyl)amino]methyl}thiophen-2-yl)phenyl]propanoic acid,
49. 2(S)-Ethoxy-3-[4-(4-{[methyl(6-propoxynaphthalene-2-carbonyl)amino]methyl}thiophen-2-yl)phenyl]propanoic acid,
50. 3-(6-{3-[3-(4-Dimethylaminophenyl)-1-methylureido]phenyl}pyrid-3-yl)-2(S)-ethoxypropanoic acid,
51. 2(S)-Ethoxy-3-[6-(3-{[methyl-(6-propoxynaphthalene-2-carbonyl)amino]methyl}phenyl)pyrid-3-yl]propanoic acid,
52. 2(S)-Ethoxy-3-(6-{3-[(heptanoylmethylamino)methyl]phenyl}pyrid-3-yl)propanoic acid,
53. 2(S)-Ethoxy-3-(6-{3-[(hexanoylmethylamino)methyl]phenyl}pyrid-3-yl)propanoic acid,
54. 2(S)-Ethoxy-3-(4-{5-[(methyloctanoylamino)methyl]furan-2-yl}phenyl)propanoic acid,
55. N-{3-[5-(3-Hydroxy-2(S)-phenylaminobut-3-enyl)pyrid-2-yl]benzyl}-N-methyloctanoylcarboxamide,
56. 2(S)-Ethoxy-3-[6'-(3-heptyl-1-methylureido)-[2,2']bipyridyl-5-yl]propanoic acid,
57. 1-(3-{2-[2(S)-Ethoxy-3-(4-methylpiperid-1-yl)-3-oxopropyl]thiazol-4-yl}phenyl)-1-methyl-3-pentylurea,
58. 1-(3-{5-[2(S)-Ethoxy-2-(5-propyl[1,3,4]oxadiazol-2-yl)ethyl]pyrimidin-2-yl}phenyl)-3-heptyl-1-methylurea,
59. 1-{6-[4-(2(S)-Ethoxy-3-oxo-3-piperid-1-ylpropyl)phenyl]pyrid-2-yl}-1-methyl-3-pentylurea,
60. 1-(6-{4-[2(S)-Ethoxy-3-(4-methylpiperid-1-yl)-3-oxopropyl]phenyl}pyrid-2-yl)-1-methyl-3-pentylurea,
61. 1-{6-[4-(2(S)-Ethoxy-3-morpholin-4-yl-3-oxopropyl]phenyl]pyrid-2-yl}-1-methyl-3-pentylurea,
62. 2(S)-Ethoxy-3-(4-{5-[(hexanoylmethylamino)methyl]thiophen-3-yl}phenyl)propanoic acid,
63. {4-[4-(2(S)-Ethoxy-3-oxo-3-piperid-1-ylpropyl)phenyl]thiophen-2-ylmethyl}methylhexanoylcarboxamide,
64. (4-{4-[2(S)-Ethoxy-3-(4-methylpiperid-1-yl)-3-oxopropyl]phenyl}thiophen-2-ylmethyl)methylhexanoylcarboxamide,
65. {4-[4-(2(S)-Ethoxy-3-morpholin-4-yl-3-oxopropyl)phenyl]thiophen-2-ylmethyl}methylhexanoylcarboxamide,
66. {4-[4-(2(S)-Ethoxy-3-oxo-3-piperid-1-ylpropyl)phenyl]thiophen-2-ylmethyl}methyloctanoylcarboxamide,
67. (4-{4-[2(S)-Ethoxy-3-(4-methylpiperid-1-yl)-3-oxopropyl]phenyl}thiophen-2-ylmethyl)methyloctanoylcarboxamide,
68. 1-{3-[5-(2(S)-Ethoxy-3-oxo-3-piperid-1-ylpropyl)pyrid-2-yl]phenyl}-1-methyl-3-pentylurea,
69. 1-(3-{5-[2(S)-Ethoxy-3-(4-methylpiperid-1-yl)-3-oxopropyl]pyrid-2-yl}phenyl)-1-methyl-3-pentylurea,
70. 1-{3-[5-(2(S)-Ethoxy-3-morpholin-4-yl-3-oxopropyl)pyrid-2-yl]phenyl}-1-methyl-3-pentylurea,
71. 1-{3-[2-(2,4-Dioxothiazolidin-5-ylmethyl)pyrimidin-5-yl]phenyl}-3-heptyl-1-methylurea,
72. 1-{3-[2-(2,4-Dioxothiazolidin-5-ylmethyl)pyrimidin-5-yl]phenyl}-1-methyl-3-pentylurea,
73. 2(S)-Ethoxy-3-{5-[3-(1-methyl-3-pentylureido)phenyl]pyrimidin-2-yl}propanoic acid,
74. 2(S)-Ethoxy-3-{6-[4-fluoro-3-(1-methyl-3-pentylureido)phenyl]pyrid-3-yl}propanoic acid,
75. 2(S)-Ethoxy-3-{2-fluoro-4-[6-(1-methyl-3-pentylureido)pyrid-2-yl]phenyl}propanoic acid,
76. 2(S)-Ethoxy-3-{4-[5-(1-methyl-3-pentylureido)thiophen-2-yl]phenyl}propanoic acid,
77. 2(S)-Ethoxy-3-{4-[5-(3-heptyl-1-methylureido)thiophen-2-yl]phenyl}propanoic acid,
78. 2(S)-Methylamino-3-(4-{5-[(methyloctanoylamino)methyl]thiophen-3-yl}phenyl)propanoic acid,
79. 2(S)-Ethylamino-3-(4-{5-[(methyloctanoylamino)methyl]thiophen-3-yl}phenyl)propanoic acid,
80. 2(S)-Ethylamino-3-(4-{5-[(hexanoylmethylamino)methyl]thiophen-3-yl}phenyl)propanoic acid,
81. 3-(4-{5-[(Hexanoylmethylamino)methyl]thiophen-3-yl}phenyl)-2(S)-methylaminopropanoic acid,
82. 2(S)-Ethylamino-3-{4-[6-(1-methyl-3-pentylureido)pyrid-2-yl]phenyl}propanoic acid,
83. 2(S)-Ethylamino-3-{4-[6-(3-heptyl-1-methylureido)pyrid-2-yl]phenyl}propanoic acid,
84. 3-{4-[6-(3-Heptyl-1-methylureido)pyrid-2-yl]phenyl}-2(S)-methylaminopropanoic acid,
85. 2(S)-Methylamino-3-{4-[6-(1-methyl-3-pentylureido)pyrid-2-yl]phenyl}propanoic acid,
86. 2(S)-Cyclopropylmethoxy-3-{4-[6-(1-methyl-3-pentylureido)pyrid-2-yl]phenyl}propanoic acid,
87. 2(S)-Ethoxy-3-[6'-(1-methyl-3-pentylureido)-[2,2]bipyridyl-5-yl]propanoic acid,
88. 2(S)-Ethoxy-3-(6-{5-[(methyloctanoylamino)methyl]thiophen-3-yl}pyrid-3-yl)propanoic acid,
89. 2(S)-Ethoxy-3-(6-{5-[(hexanoylmethylamino)methyl]thiophen-3-yl}pyrid-3-yl)propanoic acid,
90. 2-[4-(2-Carboxy-2(S)-ethoxyethyl)phenyl]-6-(3-heptyl-1-methylureido)pyridinium fumarate,
91. 2-[4-(2-Carboxy-2(S)-ethoxyethyl)phenyl]-6-(3-heptyl-1-methylureido)pyridinium maleate, 92. 3-{4-[6-(1-Methyl-3-pentylureido)pyrid-2-yl]phenyl}-2 (S)-propoxypropanoic acid,
93. 2(S)-Isopropoxy-3-{4-[6-(1-methyl-3-pentylureido)pyrid-2-yl]phenyl}propanoic acid,
94. 2(S)-Ethoxy-3-[4-(5-{[(3-1H-indol-3-ylpropionyl)methylamino]methyl}thiophen-3-yl)phenyl]propanoic acid,
95. 3-{4-[6-(3-Pentyl-1-methylureido)pyrid-2-yl]phenyl}-2-methylpropanoic acid,
96. 3-{4-[6-(3-Heptyl-1-methylureido)pyrid-2-yl]phenyl}-2-methylpropanoic acid,
97. 2-Methyl-3-(4-{5-[(methyloctanoylamino)methyl]thiophen-2-yl}phenyl)propanoic acid,
98. 3-{6-[3-(3-Heptyl-1-methylureido)phenyl]pyrid-3-yl}-2-methylpropanoic acid,
99. 2(S)-Ethoxy-3-(4-{4-[1-methyl-3-(2-piperidin-1-yl-ethyl)-ureido]-pyridin-2-yl}-phenyl)-propanoic acid,
100. 2(S)-Ethoxy-3-(4-{4-[1-methyl-3-(3-phenyl-propyl)-ureido]-pyridin-2-yl}-phenyl)-propanoic acid,
101. 2(S)-Ethoxy-3-(4-{4-[1-methyl-3-(4-phenyl-butyl)-ureido]-pyridin-2-yl}-phenyl)-propanoic acid,
102. 3-{4-[4-(3-Benzo[1,2,5]thiadiazol-4-yl-1-methyl-ureido)-pyridin-2-yl]-phenyl}-2(S)-ethoxy-propanoic acid,
103. 3-(4-{4-[3-(4-Dimethylamino-phenyl)-1-methyl-ureido]-pyridin-2-yl}-phenyl)-2(S)-ethoxy-propanoic acid,
104. 2(S)-Ethoxy-3-[4-(4-{3-[2-(1H-imidazol-2-yl)-ethyl]-1-methyl-ureido}-pyridin-2-yl)-phenyl]-propanoic acid,
105. 3-(4-{4-[3-(2-Dimethylamino-ethyl)-1-methyl-ureido]-pyridin-2-yl}-phenyl)-2(S)-ethoxy-propanoic acid,
106. 2(S)-Ethoxy-3-{4-[4-(1-methyl-3-naphthalen-2-yl-ureido)-pyridin-2-yl]-phenyl}-propanoic acid,
107. 3-{4-[6-(3-Benzo[1,2,5]thiadiazol-4-yl-1-methyl-ureido)-pyridin-2-yl]-phenyl}-2(S)-ethoxy-propanoic acid,
108. 2(S)-Ethoxy-3-(4-{6-[1-methyl-3-(3-phenyl-propyl)-ureido]-pyridin-2-yl}-phenyl)-propanoic acid,
109. 2(S)-Ethoxy-3-(4-{6-[1-methyl-3-(2-piperidin-1-yl-ethyl)-ureido]-pyridin-2-yl}-phenyl)-propanoic acid,
110. 2(S)-Ethoxy-3-(4-{6-[1-methyl-3-(4-phenyl-butyl)-ureido]-pyridin-2-yl}-phenyl)-propanoic acid,
111. 3-(4-{6-[3-(4-Dimethylamino-phenyl)-1-methyl-ureido]-pyridin-2-yl}-phenyl)-2(S)-ethoxy-propanoic acid,
112. 3-(4-{6-[3-(2-Dimethylamino-ethyl)-1-methyl-ureido]-pyridin-2-yl}-phenyl)-2(S)-ethoxy-propanoic acid,
113. 2(S)-Ethoxy-3-[4-(6-{3-[2-(1H-imidazol-2-yl)-ethyl]-1-methyl-ureido}-pyridin-2-yl)-phenyl]-propanoic acid,
114. 2(S)-Ethoxy-3-{4-[6-(1-methyl-3-pentyl-thioureido)-pyridin-2-yl]-phenyl}-propanoic acid,
115. 2(S)-Ethoxy-3-{4-[6-(1-methyl-3-heptyl-thioureido)-pyridin-2-yl]-phenyl}-propanoic acid,
116. 2(S)-Ethoxy-3-{6-[3-(3-heptyl-1-methyl-thioureido)-phenyl]-pyridin-3-yl}-propanoic acid,
117. 2(S)-Ethoxy-3-{4-[4-(3-heptyl-1-methyl-thioureido)-pyridin-2-yl]-phenyl}-propanoic acid,
118. 2(S)-Ethoxy-3-(6-{3-[1-methyl-3-(2-piperidin-1-yl-ethyl)-ureido]-phenyl}-pyridin-3-yl)-propanoic acid,
119. 3-(6-{3-[3-(2-Benzo[1,2,5]thiadiazol-4-yl-ethyl)-1-methyl-ureido]-phenyl}-pyridin-3-yl)-2(S)-ethoxy-propanoic acid,
120. 2(S)-Ethoxy-3-(6-{3-[1-methyl-3-(3-phenyl-propyl)-ureido]-phenyl}-pyridin-3-yl)-propanoic acid,
121. 3-(6-{3-[3-(4-Dimethylamino-phenyl)-1-methyl-ureido]-phenyl}-pyridin-3-yl)-2(S)-ethoxy-propanoic acid.

According to the present invention, the compounds of formula (I) that are more particularly preferred are those that have at least one of the following characteristics:

R1 is a radical of formula (a) or (b); in the case where R1 corresponds to formula (b), R3 is preferably a radical of formula (d) with R8 being a hydroxyl, NR'R" or heterocyclic radical and R4 preferably being a radical of formula OR9 in which R9 is an alkyl of 1 to 12 carbon atoms or a group of formula (f) with R11 being a hydrogen or a group COOR10;

R2 is an alkyl, aryl or heteroaryl radical;

X is the radical of structure —CH$_2$N(R14)CO— or —N(R14)-CO(D)$_w$- with w=0 or 1;

the preferred compounds contain at least one group Ar1 or Ar2 of pyridine, thiazole, pyrimidine, thiophene or triazole type.

A general description of the preparation of the compounds of general formula (I) with R1 of formula (b), such as compounds 12 to 16 and 25 to 30 of FIGS. 1A, 1B, 1C, 1D; 2A, 2B, 2C, 2D; 3A, 3B, 3C; and 4A, 4B, 4C attached hereto, is given below.

The reaction scheme described in FIGS. 1A, 1B, 1C, 1D is a general scheme for obtaining monoheterocyclic or diheterocyclic derivatives. It is particularly used in the case where Ar2 is a phenyl, since compound 2 is then commercially available.

Compound 1 with R''' equal to NR14G may be obtained from the amino derivative by monoprotection, for example with a protecting group G, for example of "boc", "fmoc" or acetyl type, followed by an alkylation with an alkyl halide in the presence of a base such as sodium hydride. Compound 1 for which R''' is equal to CH$_2$NR14G is generally prepared via a reductive amination reaction on an aldehyde function.

The intermediate 3 is obtained via a Suzuki coupling between an arylboronic acid, such as 4-formylbenzeneboronic acid, or a heteroarylboronic acid, which is commercially available or prepared beforehand from the corresponding halo derivative, and a halogenated heteroaryl derivative, for instance (6-bromo-2-pyridyl)methylamine or (5-bromo-2-thiazolyl)methylamine, optionally protected with a group G as defined above.

Compound 4 is prepared by coupling an Evans chiral reagent, for example (S)-4-benzyloxazolidin-2-one, and an acid chloride, for example of an alkoxyacetic or aralkoxyacetic acid in the case of Y=O, which is preferably commercially available, in the presence of a base, for example butyllithium.

The chiral intermediate 5 is obtained via enantioselective addition of compound 4 to the intermediate 3, in the presence of a boron derivative.

Compound 6 is obtained by dehydroxylation of compound 5 using the Barton reaction: formation of a thiocarbonic bond between the hydroxyl group to be removed and the phenyl chlorothionoformate, followed by heating to 110° C. in the presence of tributyltin hydride and a free-radical agent, AIBN.

The intermediates 9 and 11 may be prepared after deprotection of the amine (-G) by addition to an isocyanate or a thioisocyanate if D=R15 or to an acid halide if D=CH$_2$. The hydrolysis of the benzyloxazolidin-2-one part to give compound 12 is performed under conditions that allow conservation of the stereochemistry of C—OR9, for example with 1.5 equivalents of aqueous 1M lithium hydroxide solution in tetrahydrofuran, at room temperature.

The heterocyclic compounds 13 and 14 are synthesized via standard methods for synthesizing heterocycles, with, in the case of compound 14, condensation of butyric hydrazide and cyclization by heating to 105° C. in the presence of phosphorus oxychloride.

The esters 15 may be prepared, for example, by esterification with alcohols HO(CH$_2$)$_v$R10.

The compounds 16 are obtained via an amidation reaction with an amine of the type HNR'R".

Another reaction route for obtaining compounds 12 to 16 is described in FIGS. 2A, 2B, 2C, 2D.

The variation of the reaction scheme arises essentially in the production of the derivative 5.

Specifically, the intermediate 5 may also be obtained as described in FIGS. 2A, 2B, 2C, 2D via a Suzuki coupling between the boronic acid 18 and the derivative 19, which is an analogue of compound 34 for which G=R9. This synthetic route is particularly suitable for obtaining derivatives for which Ar1 is a phenyl. When Ar1 is an aromatic heterocycle, the corresponding boronic acid should be prepared beforehand according to the standard methods.

Figure 5A:
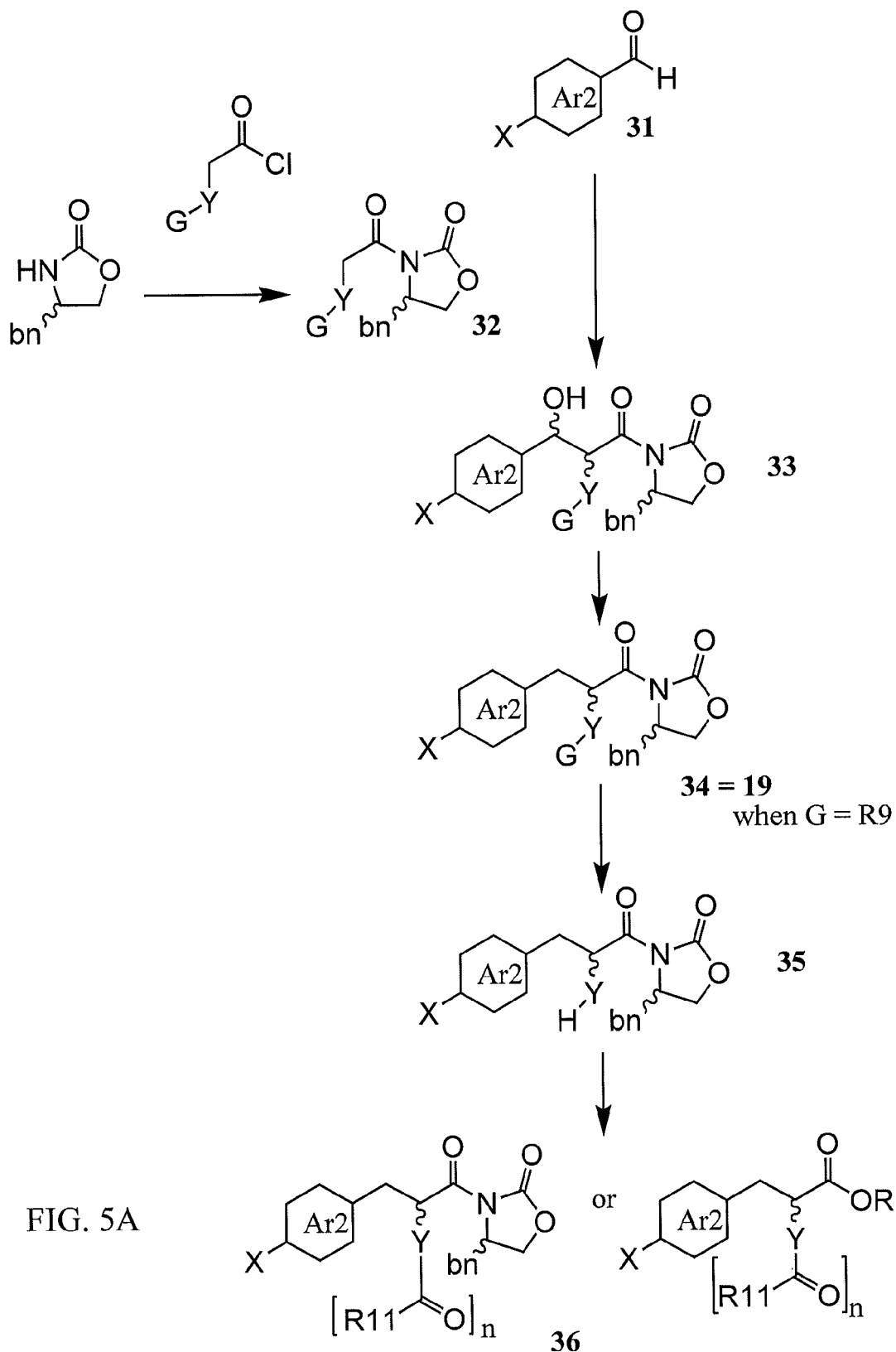
FIGS. 5A and 5B describe yet other synthetic routes.
Figure 5B:
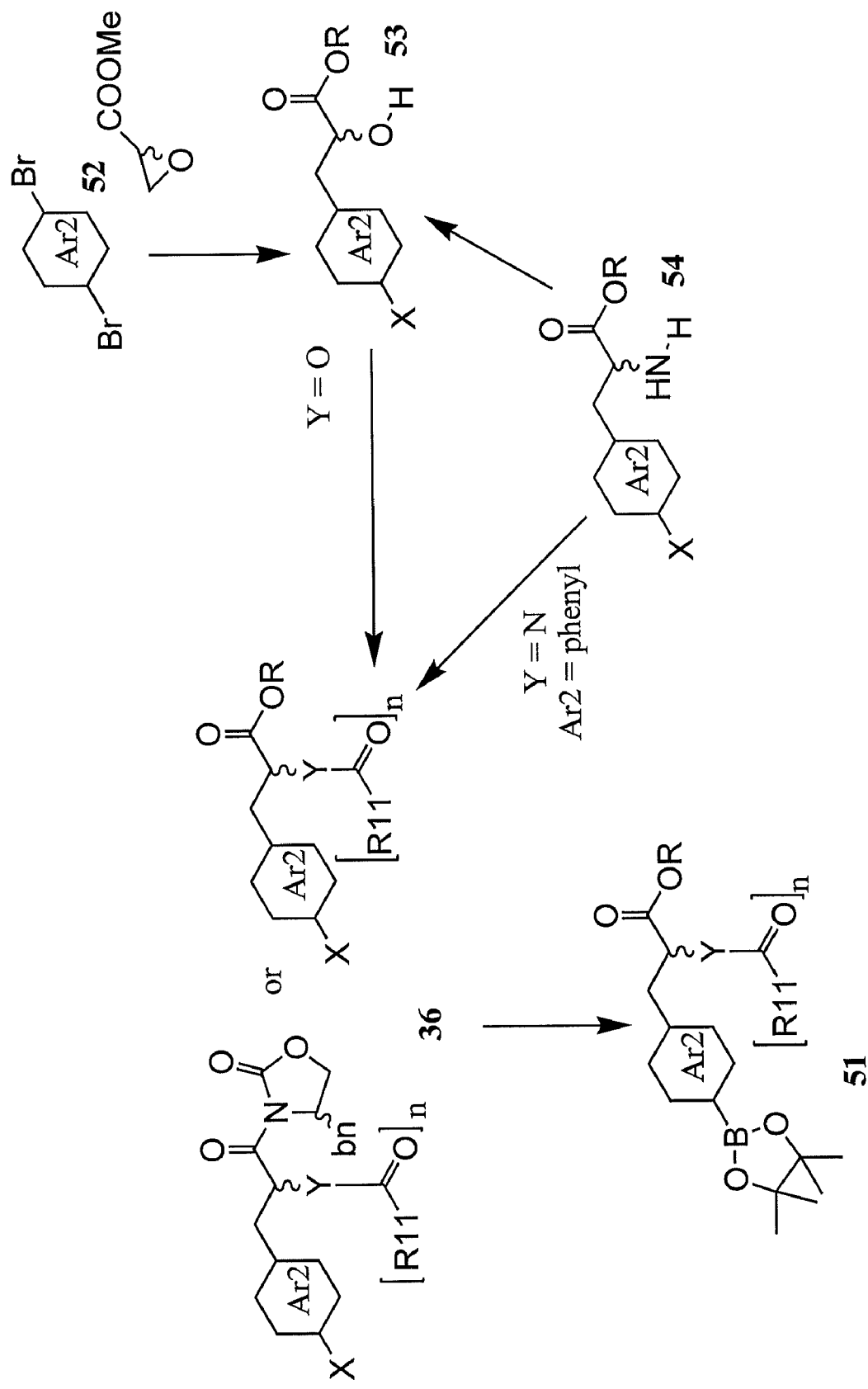

The derivative 19 is obtained according to the scheme described in FIGS. 5A and 5B: the preparation of compound 32 is performed by coupling an Evans chiral reagent, for example (S)-4-benzyloxazolidin-2-one, and an acid chloride, the function Y optionally being protected with a group G or alkylated, which is preferably commercially available, in the presence of a base, for example butyllithium. The condensation of the derivative 32 with the halogenated aldehyde 31 allows the production of compound 33. Via a Barton dehydroxylation reaction, compound 34, or 19 when the function Y is alkylated with a group R9, is obtained.

Derivative 34 is obtained by dehydroxylation of compound 33 using the Barton reaction, the chiral intermediate 33 having been obtained by enantioselective addition of compound 32 to the halogenated aromatic aldehyde 31, in the presence of a boron derivative. For the compounds with Y equal to N and Ar2 being a phenyl, the intermediate 36 may be obtained from the methyl ester of 4-bromophenylalanine (L or D) or the methyl ester of tyrosine (L or D) by addition to an acid halide (n=1) or alkylation using an alkyl halide (n=0).

Another synthetic route described in FIGS. 3A, 3B, 3C and 4A, 4B, 4C may be used.

Figure 3A:
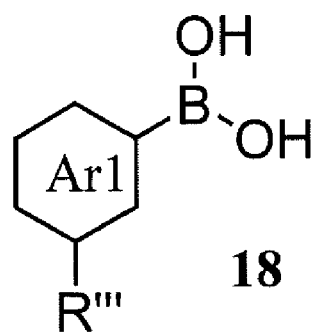
FIGS. 3A, 3B and 3C describe a reaction route to other compounds of formula (I) with R1 having formula (b) such as compounds of formulas 25 to 29.
Figure 3A:
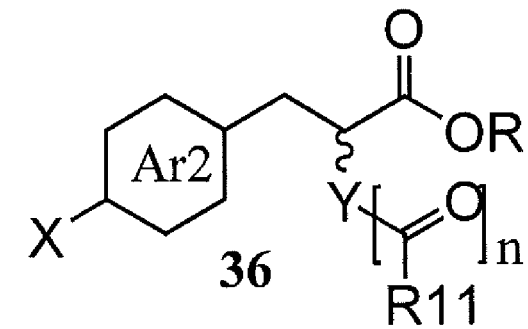
Figure 3A:
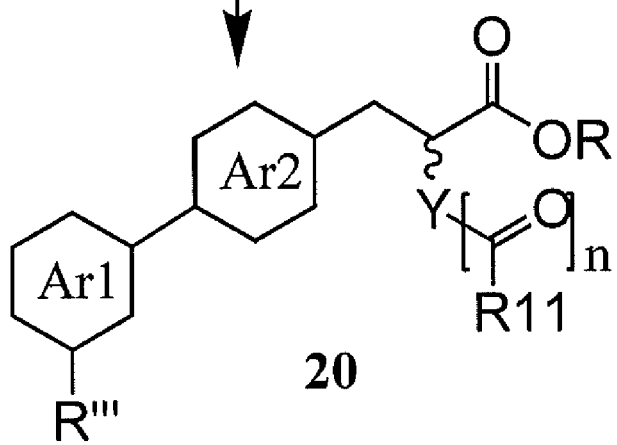
Figure 3B:
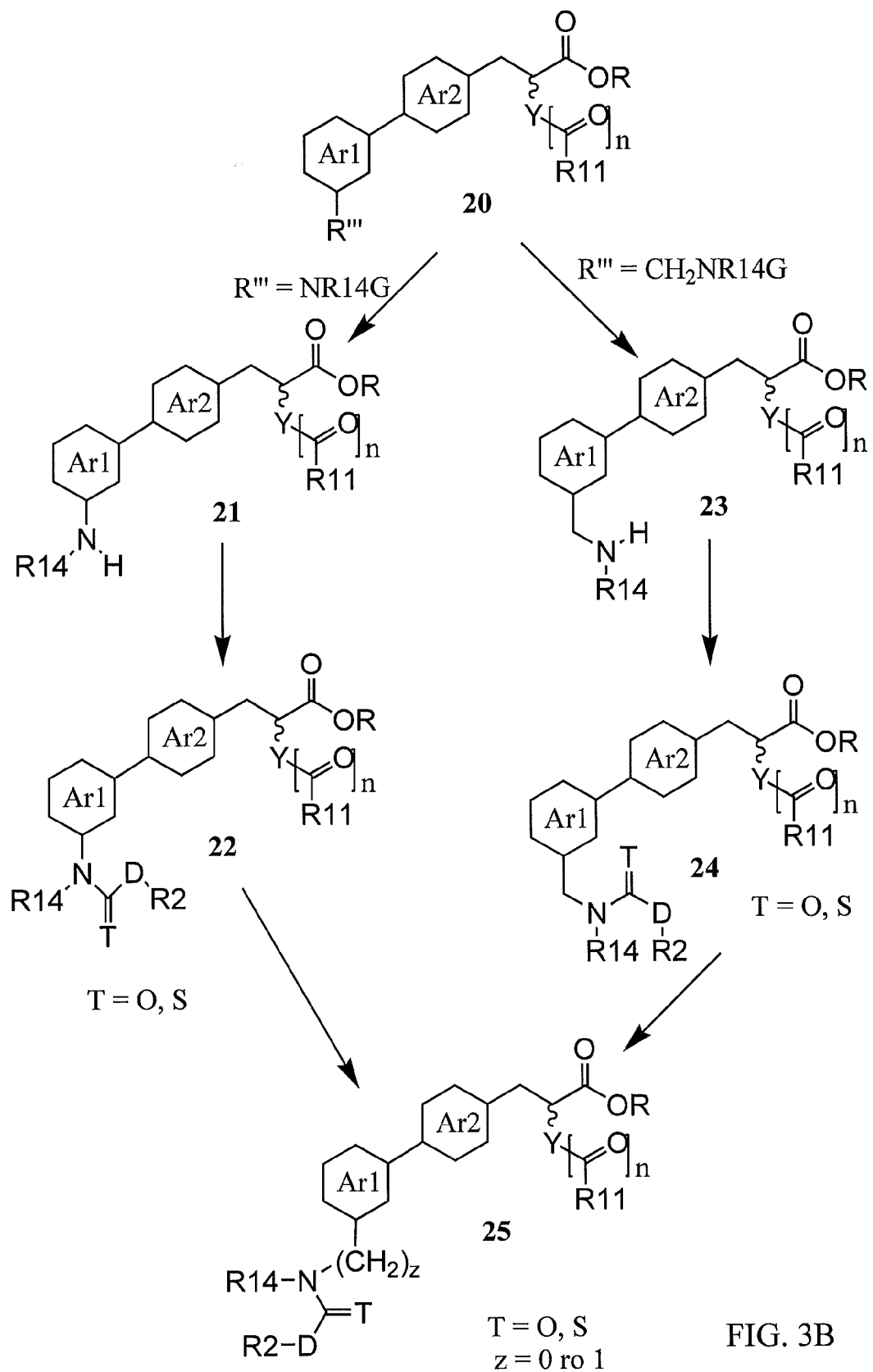
Figure 3C:
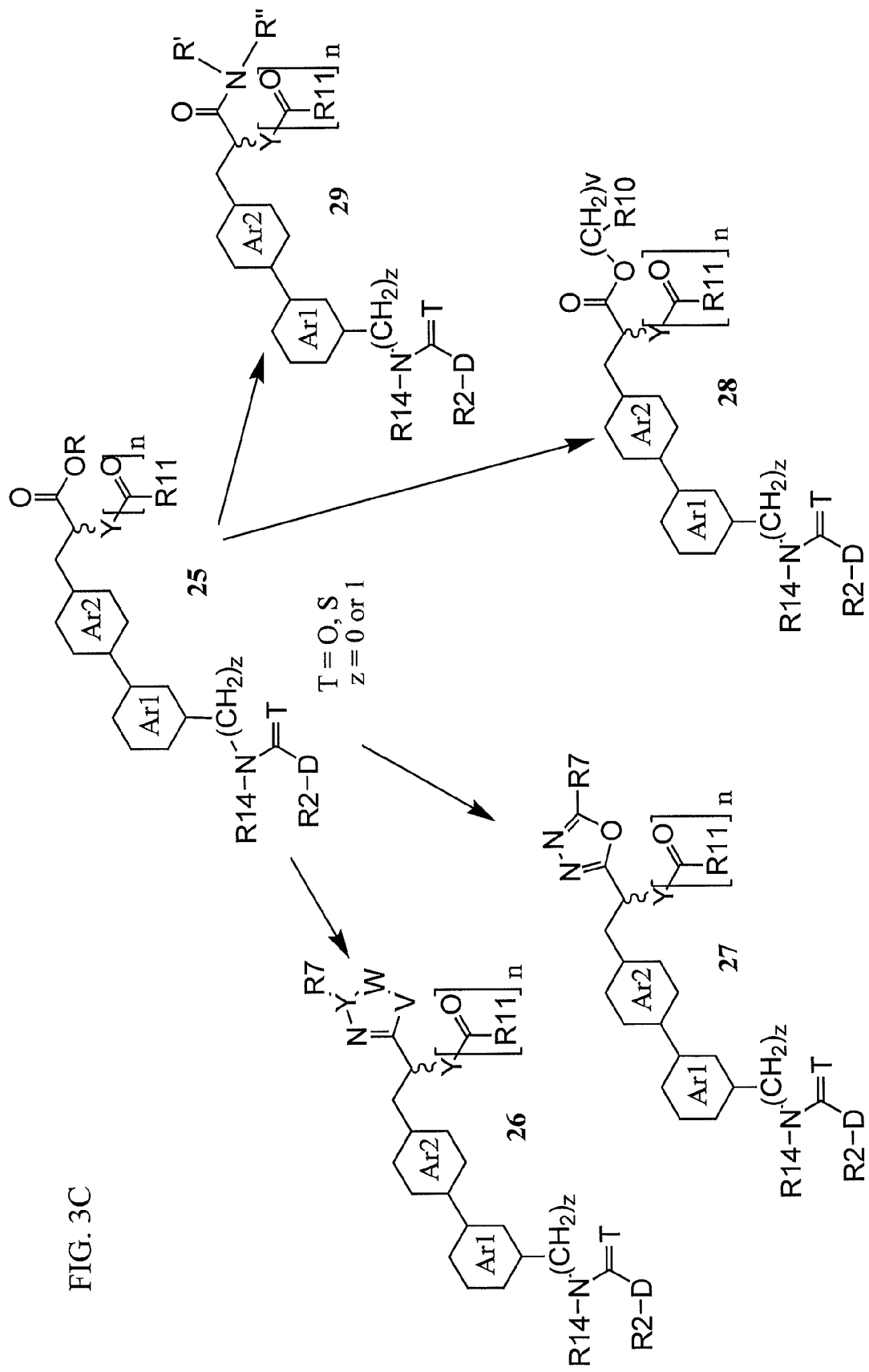
Figure 4A:
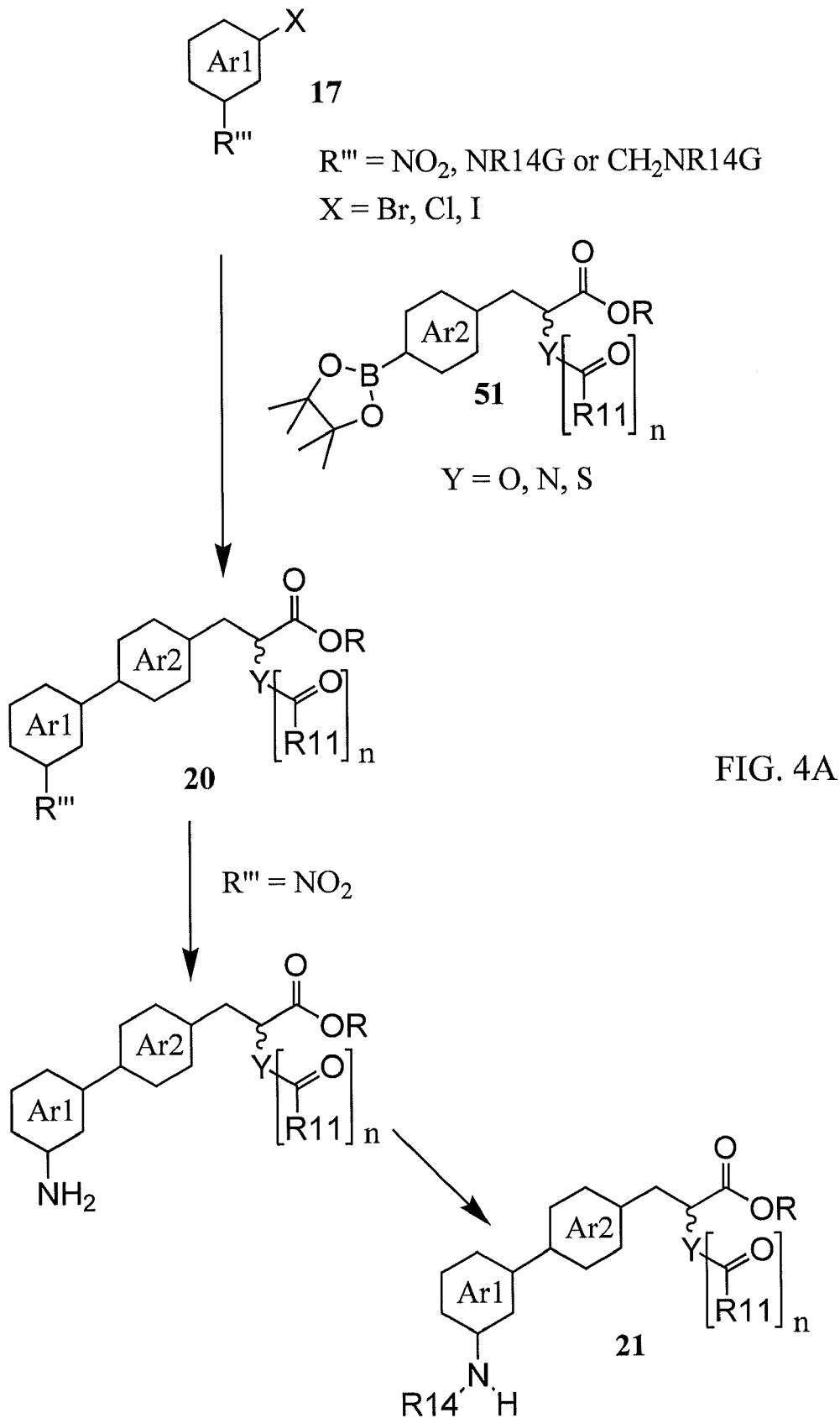
FIGS. 4A, 4B and 4C describe another reaction route to compounds of formulas 25 to 29.
Figure 4B:
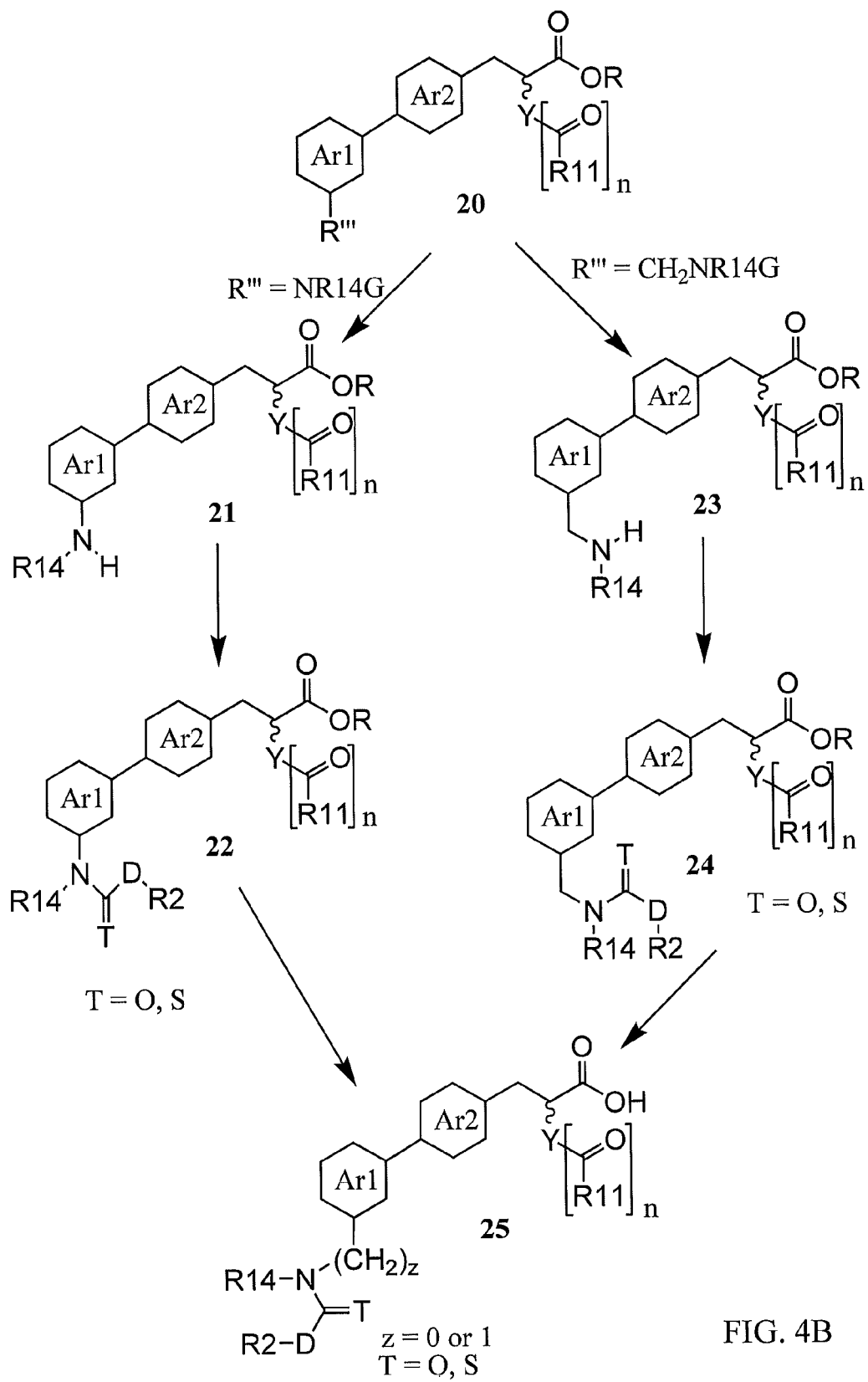
Figure 4C:
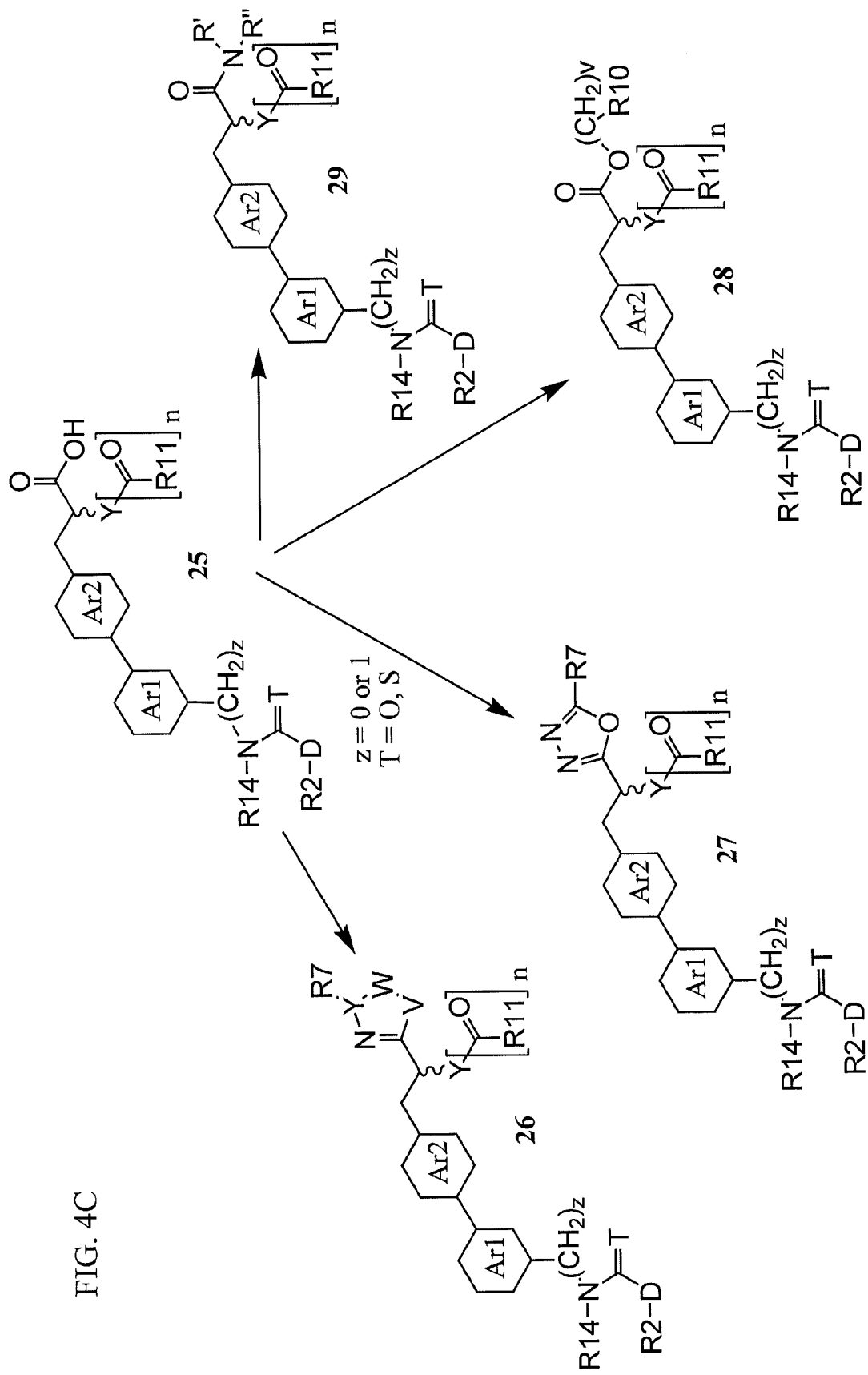

Intermediate 20 is obtained via a Suzuki coupling between the arylboronic acid 18, such as 3-formylbenzeneboronic acid, or the heteroarylboronic acid, which is commercially available or prepared beforehand from the corresponding halo derivative, and derivative 36 (FIGS. 3A, 3B, 3C). Compound 20 may also be obtained via a Suzuki reaction between a halogenated heteroaryl derivative and a boronic derivative 51 prepared beforehand. This route is often followed in the case of a group Ar2 such as a phenyl (FIGS. 4A, 4B, 4C).

Intermediate 36 may be prepared from compound 34 as shown in FIGS. 5A and 5B, after deprotection of the amine (-G) via addition to an acid halide (n=1) or alkylation with an alkyl halide (n=0).

Another route for preparing compound 36, in the case of Ar2 equal to a phenyl, consists in opening a chiral epoxide, for example 2(S)-methyl glycidate, with a monocuprate derivative formed from 1,4-dibromobenzene, followed by an enantioselective acylation or alkylation, for example in the presence of an alkyl halide and silver oxide. Compound 51 is then obtained by reacting compound 36 with bis(pinacolato) diborane in the presence of a palladium-based catalyst and potassium acetate in dimethylformamide.

Intermediates 22 and 24 may be prepared after deprotecting the amine (-G) (compounds 21 and 23) by addition to an isocyanate or a thioisocyanate if D=NR15 or to an acid halide if D=$CH_2$.

The hydrolysis of the benzyloxazolidin-2-one or alkyl ester part to give compound 25 is performed under conditions that allow the stereochemistry of the C—OR9 to be conserved, for example with 1.5 equivalents of aqueous 1M lithium hydroxide solution in tetrahydrofuran, at room temperature.

Compound 25 thus obtained is converted into compounds 26, 27, 28 and 29 according to the methods described successively for obtaining the derivatives 13, 14, 15 and 16.

A general description of the preparation of the compounds of general formula (I) with R1 of formula (a) (compound 44 of FIGS. 6A, 6B, 6C and FIGS. 7A, 7B attached hereto) is given below.

Figure 6A:
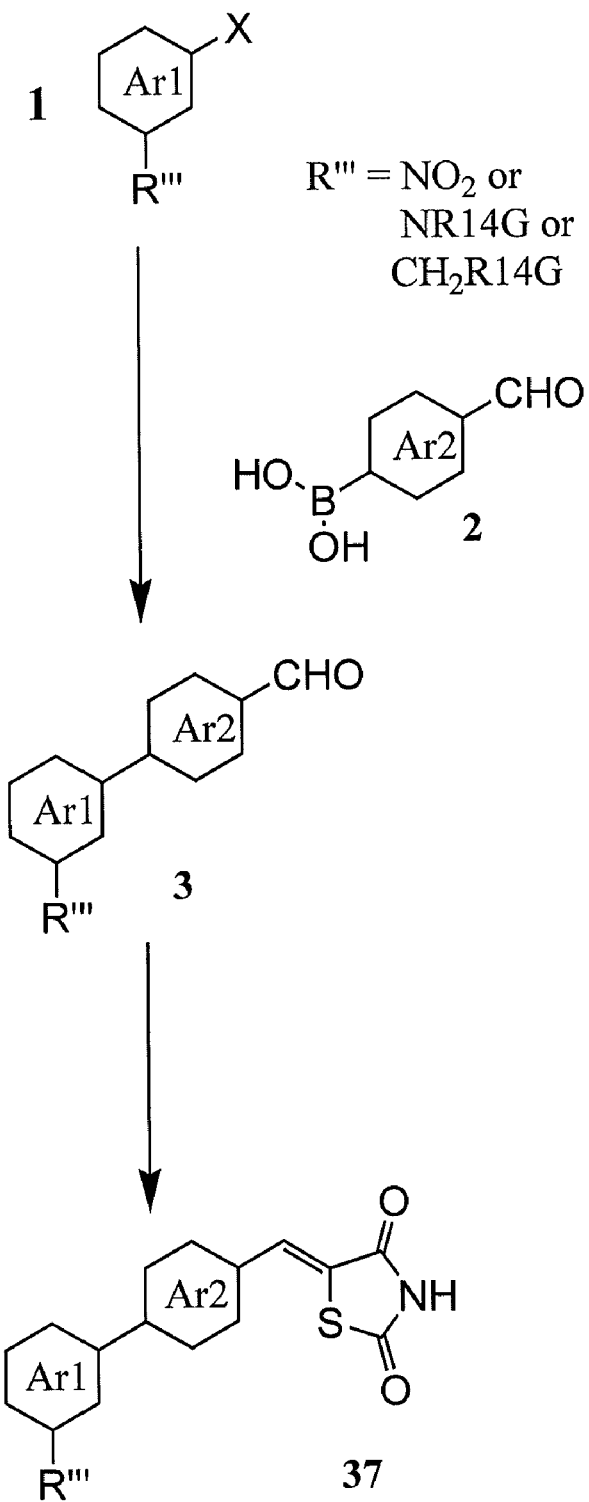
FIGS. 6A, 6B and 6C describe a reaction scheme for preparing compounds of formula (I) with R1 being formula (a).
Figure 6B:
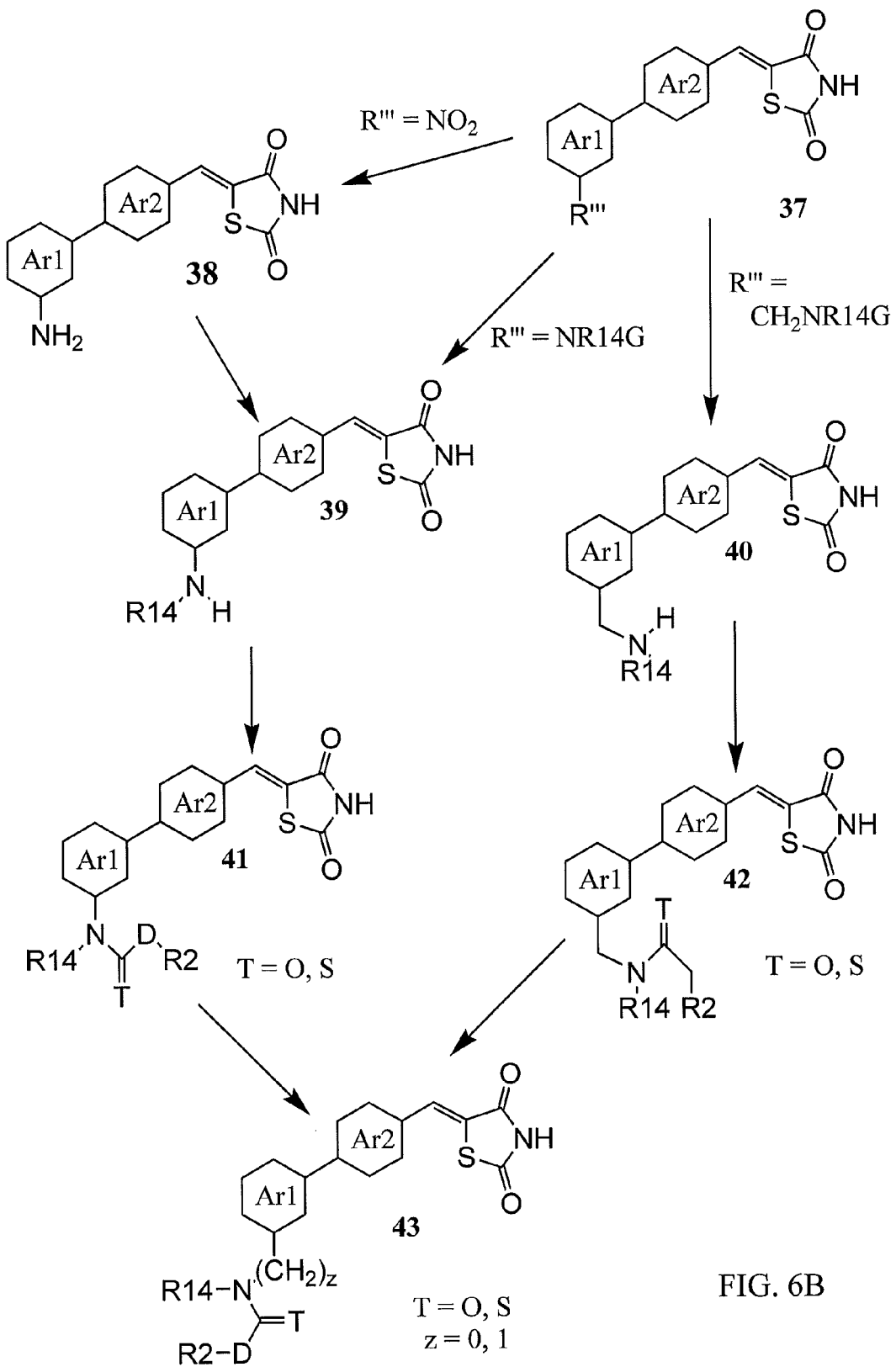
Figure 6C:
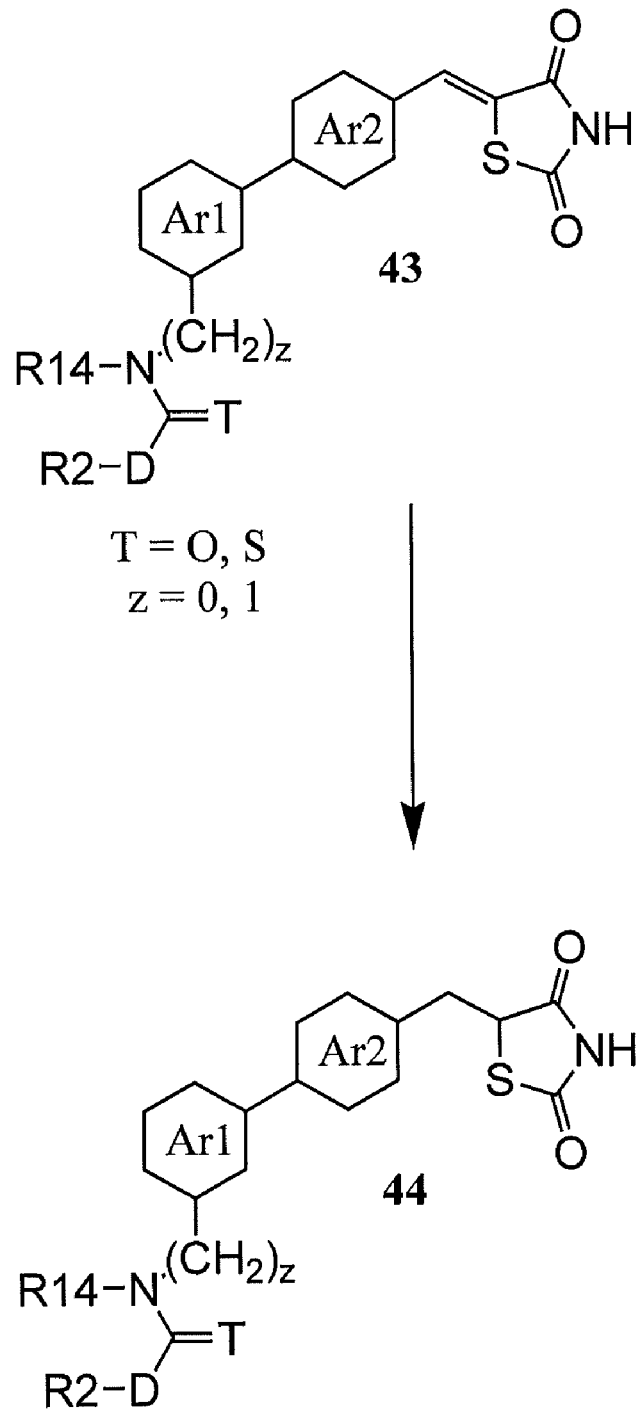

The reaction scheme described in FIGS. 6A, 6B, 6C is a general scheme for obtaining monoheterocyclic or diheterocyclic derivatives for which the variations of groups R2 are produced at the end of the synthesis.

The condensation of 2,4-thiazolidinedione with the aldehyde 3 (obtained as described above) in the presence of piperidinium acetate, for example, gives compound 37.

Intermediate 38 is obtained by reduction of the nitro function with tin chloride in the presence of hydrochloric acid. Intermediates 39 and 40 are obtained by deprotection of the amine (-G).

Compounds 41 and 42, which may be grouped together under compound 43 (z=0 or z=1, respectively) may be prepared by addition to an isocyanate or a thioisocyanate if D=NR15 or to an acid halide if D=$CH_2$.

Compound 44 is obtained, for example, by hydrogenation of compound 43 under a pressure of 3 atmospheres, in the presence of palladium-on-charcoal in a solvent, for instance dioxane.

Figure 7A:
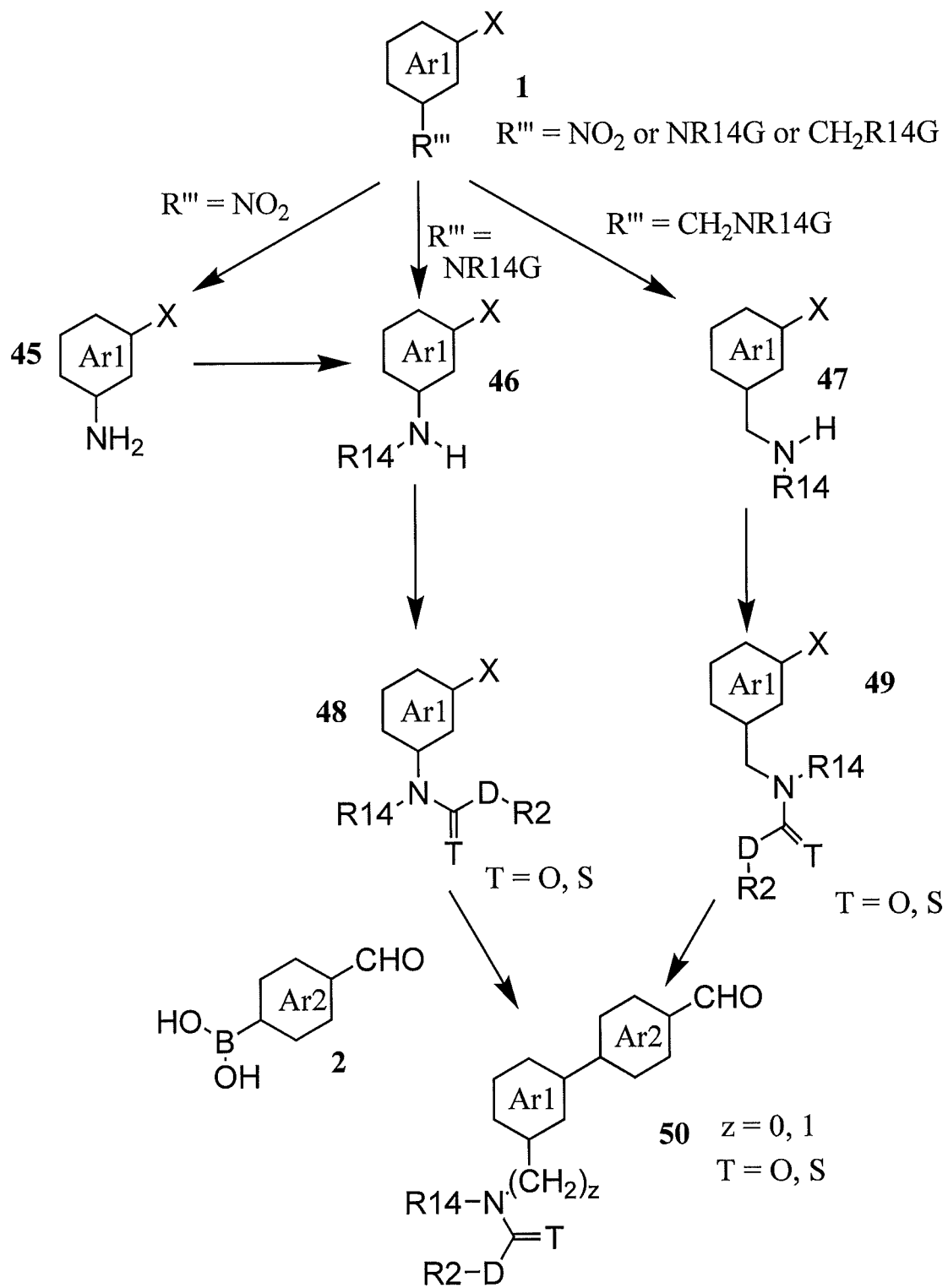
FIGS. 7A and 7B describe yet another synthetic route for compounds of formula (I) with R1 being formula (a).
Figure 7B:
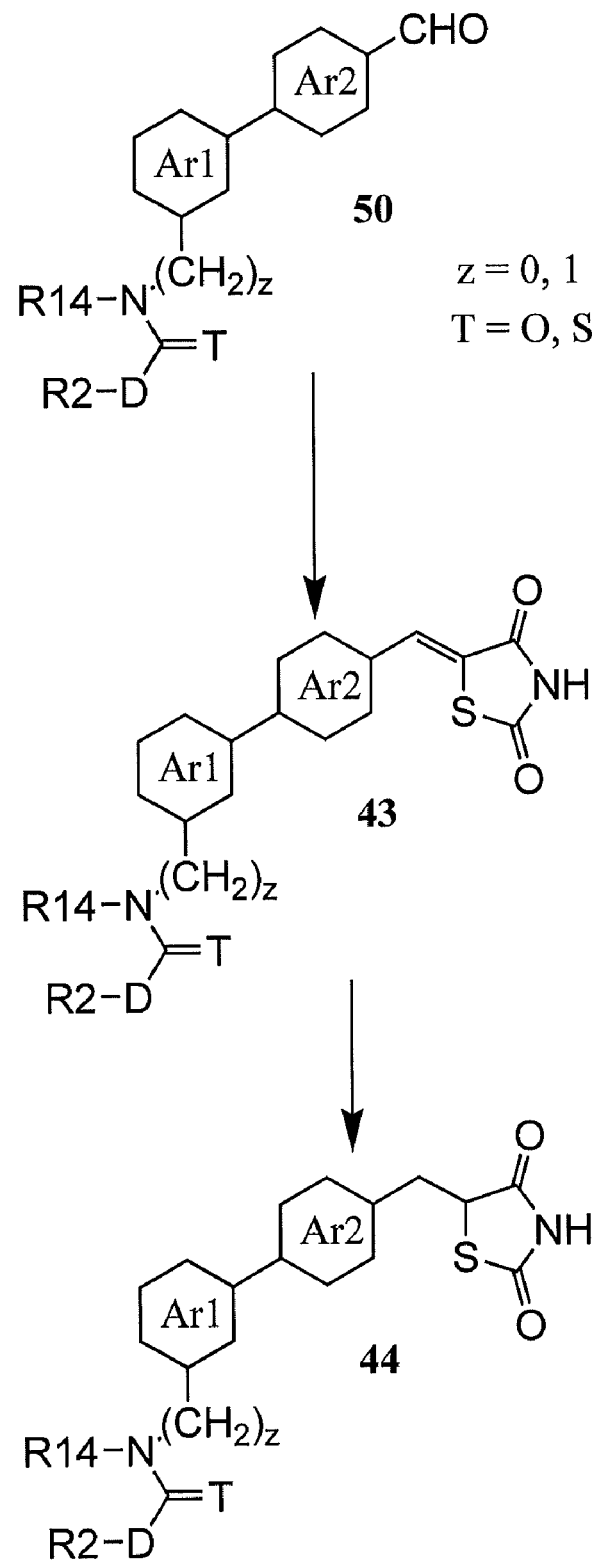

The reaction scheme described in FIGS. 7A, 7B is a scheme for which the various groups R2 are introduced at the start of the synthesis.

Compound 45 is obtained by reduction of the nitro function of compound 1. Intermediates 46 and 47 are obtained by deprotection of the amine function (-G).

Intermediates 48 and 49 are obtained by addition to an isocyanate or a thioisocyanate if D=NR15 or to an acid halide if D=$CH_2$.

Via a Suzuki reaction between compounds 48 or 49 and the boronic acid 2, compound 50 is obtained.

The condensation of 2,4-thiazolidinedione with the aldehyde 50, i.e, compound 41 if z=0 or compound 42 if z=1 (obtained as described above) in the presence of piperidinium acetate, for example, gives compound 43.

Compound 44 is obtained, for example, by hydrogenation of compound 43 under a pressure of 3 atmospheres, in the presence of palladium-on-charcoal, in a solvent, for instance dioxane.

The compounds according to the invention show modulatory properties on receptors of PPAR type. This activity on the PPARα, δ and γ receptors is measured in a transactivation test and quantified via the dissociation constant Kdapp (apparent), as described in Example 29.

The preferred compounds of the present invention have a dissociation constant of less than or equal to 5000 nM and advantageously less than or equal to 1000 nM.

Preferably, the compounds are modulators of receptors of specific PPARγ type, i.e, they have a ratio between the Kdapp for the PPARα and PPARδ receptors, and the Kdapp for the PPARγ receptors, of greater than or equal to 10. Preferably, this ratio PPARγ/PPARα or PPARγ/PPARδ is greater than or equal to 50 and more advantageously greater than or equal to 100.

The present invention also features, as medicinal products, the compounds of formula (I) as described above.

The present invention also features the use of the compounds of formula (I) to manufacture a composition for regulating and/or restoring the metabolism of skin lipids.

The compounds according to the invention are also particularly suitable in the following fields of treatment:

1) for treating dermatological complaints, conditions or afflictions associated with a keratinization disorder relating to differentiation and to proliferation, in particular for treating common acne, comedones, polymorphs, rosacea, nodulocystic acne, acne conglobata, senile acne and secondary acne such as solar, medicinal or occupational acne, 2) for treating other types of keratinization disorder, in particular ichthyosis, ichthyosiform conditions, Darier's disease, palmoplantar keratoderma, leukoplakia and leukoplakiform conditions, and cutaneous or mucous (oral) lichen, 3) for treating other dermatological complaints or afflictions with an inflammatory immuno-allergic component, with or without a cellular proliferation disorder, and in particular all forms of psoriasis, whether cutaneous, mucous or ungual psoriasis, and even psoriatic arthritis, or alternatively cutaneous atopy such as eczema, or respiratory atopy or gingival hypertrophy, 4) for treating all dermal or epidermal proliferations, whether benign or malignant, whether or not of viral origin, such as common warts, flat warts and epidermodysplasia verruciformis, oral or florid papillomatoses, T lymphoma and proliferations which may be induced by ultraviolet light, in particular in the case of basal cell and spinocellular epithelioma, and also any precancerous skin lesion such as keratoacanthomas, 5) for treating other dermatological disorders such as immune dermatitides, such as lupus erythematosus, bullous immune diseases and collagen diseases, such as scleroderma, 6) in the treatment of dermatological or systemic complaints or afflictions having an immunological component, 7) in the treatment of skin disorders due to exposure to UV radiation, and also for repairing or combating ageing of the skin, whether light-induced or chronological ageing, or for reducing actinic keratoses and pigmentations, or any pathology associated with chronological or actinic ageing, such as xerosis, 8) for combating sebaceous function disorders such as the hyperseborrhoea of acne, simple seborrhoea or seborrhoeic dermatitis, 9) for preventing or treating cicatrization disorders or for preventing or repairing stretch marks, 10) in the treatment of pigmentation disorders, such as hyperpigmentation, melasma, hypopigmentation or vitiligo, 11) in the treatment of lipid metabolism complaints or afflications, such as obesity, hyperlipidaemia, non-insulin-dependent diabetes or syndrome X, 12) in the treatment of inflammatory complaints or afflictions, such as arthritis, 13) in the treatment or prevention of cancerous or precancerous conditions, 14) in the prevention or treatment of alopecia of various origins, in particular alopecia caused by chemotherapy or radiation, 15) in the treatment of immune system disorders, such as asthma, type I sugar diabetes, multiple sclerosis or other selective dysfunctions of the immune system, or 16) in the treatment of complaints or afflictions of the cardiovascular system, such as arteriosclerosis or hypertension.

The present invention also features pharmaceutical or cosmetic compositions comprising, formulated into a physiologically acceptable medium, at least one compound of formula (I) as defined above.

The composition according to the invention may be administered enterally, parenterally, topically or ocularly. The pharmaceutical composition is preferably packaged in a form that is suitable for topical application.

Via the enteral route, the composition, more particularly the pharmaceutical composition, may be in the form of tablets, gel capsules, sugar-coated tablets, syrups, suspensions, solutions, powders, granules, emulsions or lipid or polymer vesicles or nanospheres or microspheres to allow controlled release. Via the parenteral route, the composition may be in the form of solutions or suspensions for infusion or for injection.

The compounds according to the invention are generally administered at a daily dose of about 0.001 mg/kg to 100 mg/kg of body weight in 1 to 3 dosage intakes.

The compounds are used systemically at a concentration generally of from 0.001% to 10% by weight and preferably from 0.01% to 1% by weight relative to the weight of the composition.

Via the topical route, the pharmaceutical composition according to the invention is more particularly intended for treating the skin and mucous membranes and may be in the form of ointments, creams, milks, salves, powders, impregnated pads, syndets, solutions, gels, sprays, foams, suspensions, stick lotions, shampoos or washing bases. It may also be in the form of suspensions of lipid or polymer vesicles or nanospheres or microspheres or polymer patches and hydrogels to allow controlled release. This topical-route composition may be in anhydrous form, in aqueous form or in the form of an emulsion.

The compounds are used topically at a concentration generally of from 0.001% to 10% by weight, preferably from 0.01% to 1% by weight relative to the total weight of the composition.

The compounds of formula (I) according to the invention also find an application in the cosmetic field, in particular in body and hair hygiene and more particularly for regulating and/or restoring skin lipid metabolism.

The invention therefore also features the cosmetic use of a composition comprising, in a physiologically acceptable support, at least one of the compounds of formula (I) for body or hair hygiene.

The cosmetic compositions according to the invention containing, in a cosmetically acceptable support, at least one compound of formula (I) or an optical or geometrical isomer thereof or a salt thereof, may usually be in the form of a cream, a milk, a lotion, a gel, suspensions of lipid or polymer vesicles or nanospheres or microspheres, impregnated pads, solutions, sprays, foams, sticks, soaps, shampoos or washing bases.

The concentration of compound of formula (I) in the cosmetic composition is from 0.0001% to 2% by weight relative to the total weight of the composition.

The pharmaceutical and cosmetic compositions as described above may also contain inert or even pharmacodynamically active additives as regards the pharmaceutical compositions, or combinations of these additives, and especially:

wetting agents;
flavor enhancers;
preservatives such as para-hydroxybenzoic acid esters;
stabilizers;
humidity regulators;
pH regulators;
osmotic pressure modifiers;
emulsifiers;
UV-A and UV-B screening agents;

antioxidants, such as α-tocopherol, butylhydroxyanisole or butylhydroxytoluene, superoxide dismutase, ubiquinol or certain metal-chelating agents;

depigmenting agents such as hydroquinone, azelaic acid, caffeic acid or kojic acid;

emollients;

moisturizers, for instance glycerol, PEG 400, thiamorpholinone and derivatives thereof, or urea;

anti-seborrhoeic or anti-acne agents, such as S-carboxymethylcysteine, S-benzylcysteamine, salts thereof or derivatives thereof, or benzoyl peroxide;

antibiotics, for instance erythromycin and its esters, neomycin, clindamycin and its esters, and tetracyclines;

anti-fungal agents such as ketoconazole or polymethylene-4,5-isothiazolidones-3;

agents for promoting regrowth of the hair, for instance Minoxidil (2,4-diamino-6-piperidinopyrimidine 3-oxide) and its derivatives, Diazoxide (7-chloro-3-methyl-1,2,4-benzothiadiazine 1,1-dioxide) and Phenyloin (5,4-diphenylimidazolidine-2,4-dione);

non-steroidal anti-inflammatory agents;

carotenoids, and especially β-carotene;

anti-psoriatic agents such as anthralin and its derivatives;

eicosa-5,8,11,14-tetraynoic acid and eicosa-5,8,11-triynoic acid, and esters and amides thereof;

retinoids, i.e, RAR or RXR receptor ligands, which may be natural or synthetic;

corticosteroids or oestrogens;

α-hydroxy acids and α-keto acids or derivatives thereof, such as lactic acid, malic acid, citric acid, glycolic acid, mandelic acid, tartaric acid, glyceric acid or ascorbic acid, and also the salts, amides or esters thereof, or β-hydroxy acids or derivatives thereof, such as salicylic acid and the salts, amides or esters thereof;

ion-channel blockers such as potassium-channel blockers;

or alternatively, more particularly for the pharmaceutical compositions, in combination with medicinal products known to interfere with the immune system (for example cyclosporin, FK 506, glucocorticoids, monoclonal antibodies, cytokines or growth factors, etc.).

Needless to say, one skilled in this art will take care to select the optional compound(s) to be added to these compositions such that the advantageous properties intrinsically associated with the present invention are not, or are not substantially, adversely affected by the envisaged addition.

The present invention also features a cosmetic regime or regimen for beautifying the skin, wherein a composition comprising at least one compound of formula (I) as defined above is topically applied onto the skin. Regulation and/or restoration of the metabolism of the skin lipids makes it possible to obtain skin whose surface appearance is embellished.

Several examples of the production of active compounds of formula (I) according to the invention, and also biological activity results for such compounds and various concrete formulations based on its compounds will now be given, by way of illustration and in nowise limitative.

EXAMPLE 1

Synthesis of N-{4-[4-(2,4-Dioxothiazolidin-5-ylmethyl)phenyl]thiophen-2-ylmethyl}-N-methylbenzamide (a) Preparation of (4-Bromothiophen-2-ylmethyl)methylamine 18 g (260 mmol) of methylamine hydrochloride and then 7.5 g (100 mmol) of sodium cyanoborohydride are successively added to a solution of 10 g (50 mmol) of 4-bromo-2-thiophenecarboxaldehyde in 150 ml of methanol. The reaction medium is stirred at room temperature for 24 hours and then filtered under vacuum. After evaporating the filtrate to dryness, the residue is taken up in dichloromethane. The organic phase obtained is washed with 1N hydrochloric acid solution. The aqueous phase thus obtained is treated with aqueous 1N sodium hydroxide solution and extracted with dichloromethane. The organic phase is dried over magnesium sulfate, filtered and evaporated under vacuum. 4.5 g (44%) of (4-bromothiophen-2-ylmethyl)methylamine are obtained.

(b) Preparation of N-(4-Bromothiophen-2-ylmethyl)-N-methylbenzamide 2.8 ml (24 mmol) of benzoyl chloride are added dropwise to a solution of 4.5 g (22 mmol) of (4-bromothiophen-2-ylmethyl)methylamine and 6 ml (44 mmol) of triethylamine in 75 ml of tetrahydrofuran. After stirring at room temperature for 1 hour, the precipitate is filtered off and the filtrate is concentrated under vacuum. The residue is taken up in dichloromethane and washed with water.

The organic phase obtained is dried over magnesium sulfate, filtered and concentrated under vacuum. The residue obtained is purified by chromatography on a column of silica eluted with an 8/2 heptane/ethyl acetate mixture. 4.8 g (71%) of N-(4-bromothiophen-2-ylmethyl)-N-methylbenzamide are obtained in the form of an oil.

(c) Preparation of N-[4-(4-Formylphenyl)thiophen-2-ylmethyl]-N-methyl-benzamide 3 g (20 mmol) of 4-formylbenzeneboronic acid are added to a solution of 4.75 g (15 mmol) of N-(4-bromothiophen-2-ylmethyl)-N-methylbenzamide in 60 ml of toluene, followed by dropwise addition of 5.5 g (40 mmol) of aqueous potassium carbonate solution. The reaction medium is degassed, 530 mg (0.5 mmol) of tetrakis (triphenylphosphine) palladium are then added and the medium is heated at 80° C. for 18 hours. After extraction with ethyl acetate and washing with water, the organic phase is dried over magnesium sulfate, filtered and concentrated under vacuum. The residue obtained is purified by chromatography on a column of silica eluted with a 1/1 heptane/ethyl acetate mixture. 4 g (78%) of N-[4-(4-formylphenyl)thiophen-2-ylmethyl]-N-methyl-benzamide are obtained.

(d) Preparation of N-{4-[4-(2,4-Dioxothiazolidin-5-ylidenemethyl)phenyl]thiophen-2-ylmethyl}-N-methylbenzamide A solution of 4 g (9 mmol) of N-[4-(4-formylphenyl)thiophen-2-ylmethyl]-N-methylbenzamide, 1.1 g (9 mmol) of 2,4-thiazolidinedione and 0.3 g (1.8 mmol) of piperidinium acetate in 40 ml of toluene is refluxed for 2 hours in a Dean-Stark system. The reaction medium is cooled and the precipitate is filtered off under vacuum. 3 g (78%) of N-{4-[4-(2,4-dioxothiazolidin-5-ylidenemethyl)phenyl]thiophen-2-ylmethyl}-N-methylbenzamide are obtained.

(e) Synthesis of N-{4-[4-(2,4-Dioxothiazolidin-5-ylmethyl)phenyl]thiophen-2-ylmethyl}-N-methyl-benzamide 2 g (1 mass equivalent) of palladium-on-charcoal are added to a solution of 2 g (4.6 mmol) of N-{4-[4-(2,4-dioxothiazolidin-5-ylidenemethyl)phenyl]thiophen-2-ylmethyl}-N-methylbenzamide in 20 ml of dioxane that has been degassed beforehand, and the reaction medium is placed under 3 atm of hydrogen, at 50° C. for 6 hours. After filtering off the palladium through Celite, the filtrate is concentrated under vacuum. The residue obtained is purified by chromatography on a column of silica eluted with a 9.5/0.5 dichloromethane/methanol mixture. 1.5 g (75%) of N-{4-[4-(2,4-dioxothiazolidin-5-ylmethyl)phenyl]thiophen-2-ylmethyl}-N-methylbenzamide are obtained in the form of a solid with a melting point of 134° C.

$^1$H NMR (δ, CDCl$_3$): 2.98-3.10 (m, 3H); 3.15 (dd, J=22 Hz, J=7 Hz, 1H); 3.52 (dd, J=6.1 Hz, J=22 Hz, 1H); 4.53 (dd, J=6.1 Hz, J=15 Hz, 1H); 4.63-4.89 (m, 2H); 7.15-7.54 (m, 11H); 8.94 (s, 1H).

EXAMPLE 2

Synthesis of N-{5-[4-(2,4-Dioxothiazolidin-5-ylmethyl)phenyl]thiophen-3-ylmethyl}-N-methylbenzamide (a) Preparation of Ethyl thiophene-3-carboxylate 13 ml (200 mmol) of thionyl chloride are added dropwise, at 0° C., to a solution of 9 g (70 mmol) of 3-thiophenecarboxylic acid and 86 mg (0.7 mmol) of 4-dimethylaminopyridine in 100 ml of ethanol. The reaction medium is stirred from 0° C. to room temperature over 48 hours and then evaporated to dryness. The residue obtained is purified by chromatography on a column of silica eluted with a 1/1 heptane/dichloromethane mixture. 10 g (91%) of ethyl thiophene-3-carboxylate are obtained.

(b) Preparation of Ethyl 5-bromothiophene-3-carboxylate 20 g (147 mmol) of aluminum chloride are added portionwise to a solution of 10 g (67 mmol) of ethyl thiophene-3-carboxylate in 160 ml of dichloromethane, cooled beforehand to 0° C. The reaction medium is warmed to room temperature and a solution of 4 ml (73 mmol) of bromine in 10 ml of dichloromethane is then added. After reaction for 50 minutes at room temperature, the reaction medium is poured into a water+ice mixture and extracted with dichloromethane. The organic phase is dried over magnesium sulfate, filtered and evaporated under vacuum. The residue obtained is purified by chromatography on a column of silica eluted with a 9/1 heptane/ethyl acetate mixture. 9 g (57%) of ethyl 5-bromothiophene-3-carboxylate are obtained.

(c) Preparation of 5-Bromothiophene-3-carboxylic acid 7.4 g (185 mmol) of sodium hydroxide pellets are added to a solution of 8.7 g (37 mmol) of ethyl 5-bromothiophene-3-carboxylate in 100 ml of tetrahydrofuran, 10 ml of methanol and a few drops of water. After stirring at room temperature for 18 hours, the reaction medium is taken up in ethyl acetate and washed with water. The aqueous phase obtained is acidified to pH 1 with aqueous hydrochloric acid solution and then extracted with dichloromethane. The organic phase obtained is dried over magnesium sulfate, filtered and concentrated under vacuum. 7 g (92%) of 5-bromothiophene-3-carboxylic acid are obtained.

(d) Preparation of 5-Bromothiophene-N-methyl-3-carboxylamide 4.7 g (35 mmol) of 1-hydroxybenzotriazole, 2.2 g (32 mmol) of methylamine hydrochloride and 4.5 ml (32 mmol) of triethylamine are successively added to a solution of 6.7 g (32 mmol) of 5-bromothiophene-3-carboxylic acid in 120 ml of dichloromethane. The reaction medium is cooled to 0° C. and a solution of 6.7 g (35 mmol) of 1-(3-dimethylaminopropyl)-3-ethylcarbodiimide hydrochloride is added dropwise. After 1 hour at 0° C., the reaction medium is stirred at room temperature for 2 days. The dichloromethane phase is washed with water, dried over sodium sulfate, filtered and evaporated under vacuum. The residue obtained is triturated from a heptane/ethyl acetate mixture, filtered and evaporated. 5.6 g (60%) of 5-bromothiophene-N-methyl-3-carboxylamide are obtained.

(e) Preparation of (5-Bromothiophen-3-ylmethyl)methylamine

A solution of 9 ml (18 mmol) of 2M dimethyl sulfide borohydride in toluene is added dropwise to a suspension of 3.7 g (17 mmol) of 5-bromothiophene-N-methyl-3-carboxylamide in 50 ml of toluene, cooled beforehand to −78° C. After addition, the reaction medium is stirred from −78° C. to room temperature over 16 hours and then refluxed for 5 hours. Aqueous 10% sodium carbonate solution is added to the reaction medium, and the medium is extracted with dichloromethane. After acid-base washing, the organic phase is dried over magnesium sulfate, filtered and concentrated under vacuum. 2.3 g (66%) of (5-bromothiophen-3-ylmethyl) methylamine are obtained.

(f) Preparation of N-(5-Bromothiophen-3-ylmethyl)-N-methylbenzamide 1.6 ml (13 mmol) of benzoyl chloride are added dropwise to a solution of 2.3 g (11 mmol) of (5-bromothiophen-3-ylmethyl)methylamine and 3 ml (22 mmol) of triethylamine in 30 ml of tetrahydrofuran. The reaction medium is stirred at room temperature for 1 hour, filtered, diluted with ethyl acetate and washed with water. The organic phase obtained is dried over sodium sulfate, filtered and evaporated to dryness. The residue obtained is purified by chromatography on a column of silica eluted with an 8/2 heptane/ethyl acetate mixture. 3.1 g (80%) of N-(5-bromothiophen-3-ylmethyl)-N-methylbenzamide are obtained.

(g) Preparation of N-[5-(4-formylphenyl)thiophen-3-ylmethyl]-N-methylbenzamide

In a manner similar to that of Example 1(c), starting with 3 g (10 mmol) of N-(5-bromothiophen-3-ylmethyl)-N-methylbenzamide and 1.9 g (13 mmol) of 4-formylbenzeneboronic acid, 2.6 g (80%) of N-[5-(4-formylphenyl)thiophen-3-ylmethyl]-N-methylbenzamide are obtained after purification by chromatography on a column of silica eluted with a 7/3 heptane/ethyl acetate mixture.

(h) Preparation of N-{5-[4-(2,4-Dioxothiazolidin-5-ylidenemethyl)phenyl]thiophen-3-ylmethyl}-N-methylbenzamide In a manner similar to that of Example 1(d), starting with 2.6 g (8 mmol) of N-[5-(4-formylphenyl)thiophen-3-ylmethyl]-N-methylbenzamide and 1 g (8.5 mmol) of 2,4-thiazolidinedione, 2.2 g (63%) of N-{5-[4-(2,4-dioxothiazolidin-5-ylidenemethyl)phenyl]thiophen-3-ylmethyl}-N-methylbenzamide are obtained.

(i) Synthesis of N-{5-[4-(2,4-Dioxothiazolidin-5-ylmethyl)phenyl]thiophen-3-ylmethyl}-N-methylbenzamide In a manner similar to that of Example 1(e), by hydrogenation of 1.8 g (4.2 mmol) of N-{5-[4-(2,4-dioxothiazolidin-5-ylidenemethyl)phenyl]thiophen-3-ylmethyl}-N-methylbenzamide, 800 mg (45%) of N-{5-[4-(2,4-dioxothiazolidin-5-ylmethyl)phenyl]thiophen-3-ylmethyl}-N-methylbenzamide are obtained in the form of a solid with a melting point of 153° C.

$^1$H NMR (δ, CDCl$_3$): 2.93-3.10 (m, 3H); 3.15 (dd, J=22 Hz, J=7 Hz, 1H); 3.51 (dd, J=6.1 Hz, J=22 Hz, 1H); 4.49 (dd, J=6.1 Hz, J=15 Hz, 1H); 4.63-4.89 (m, 2H); 7.02-7.69 (m, 11H); 9.36 (s, 1H).

EXAMPLE 3

Synthesis of N-{5-[4-(2,4-Dioxothiazolidin-5-ylmethyl)phenyl]pyrid-3-ylmethyl}-N-methylbenzamide

(a) Preparation of Ethyl 5-bromonicotinate 20 ml (27 mmol) of thionyl chloride are added dropwise, at room temperature, to a solution of 10 g (49 mmol) of 5-bromonicotinic acid in 250 ml of ethanol. The reaction medium is stirred at room temperature for 4 days and then evaporated under vacuum. The residue is taken up in dichloromethane and washed with aqueous sodium carbonate solution. The organic phase is dried over sodium sulfate, filtered and evaporated under vacuum. The residue obtained is purified by chromatography on a column of silica eluted with a 7/3 heptane/ethyl acetate mixture. 9 g (82%) of ethyl 5-bromonicotinate are obtained.

(b) Preparation of (5-Bromopyrid-3-yl)methanol

A solution of 9 g (40 mmol) of ethyl 5-bromonicotinate in 25 ml of methanol is added dropwise, at room temperature, to a suspension of 14.8 g (400 mmol) of sodium borohydride in 75 ml of methanol. After addition, the reaction medium is refluxed for 2 hours. The reaction medium is evaporated to dryness, taken up in aqueous sodium hydroxide solution to pH 9, and extracted with ethyl acetate. The organic phase is dried over magnesium sulfate, filtered and evaporated under vacuum. 3.7 g (50%) of (5-bromopyrid-3-yl)methanol are obtained.

(c) Preparation of 5-Bromopyridine-3-carbaldehyde 4.5 g (21 mmol) of pyridinium chlorochromate are added at room temperature to a solution of 3 g (16 mmol) of (5-bromopyrid-3-yl)methanol in 70 ml of dichloromethane. After stirring for 1 hour, 70 ml of diethyl ether are added and the reaction medium is again stirred for 1 hour. The precipitate is filtered off through sodium sulfate and the filtrate is evaporated to dryness. The residue obtained is purified by chromatography on a column of silica eluted with a 7/3 heptane/ethyl acetate mixture. 1 g (35%) of 5-bromopyridine-3-carbaldehyde is obtained.

(d) Preparation of (5-Bromopyrid-3-ylmethyl)methylamine 1.8 g (27 mmol) of methylamine hydrochloride and then 0.4 g (6 mmol) of sodium cyanoborohydride are successively added to a solution of 1 g (5.4 mmol) of 5-bromopyridine-3-carbaldehyde in 20 ml of methanol. The reaction medium is stirred at room temperature for 2 days. The precipitate is filtered off and the filtrate is evaporated to dryness. The residue is taken up in dichloromethane and washed with water. After extraction, the organic phase obtained is washed with aqueous hydrochloric acid solution. The aqueous phase thus obtained is brought to pH 9 with aqueous sodium hydroxide solution and then extracted with dichloromethane. The organic phase thus obtained is dried over magnesium sulfate, filtered and concentrated under vacuum. The residue obtained is purified by chromatography on a column of silica eluted with a 9.5/0.5 dichloromethane/methanol mixture. 0.5 g (50%) of (5-bromopyrid-3-ylmethyl)methylamine is obtained.

(e) Preparation of N-(5-Bromopyrid-3-ylmethyl)-N-methylbenzamide

In a manner similar to that of Example 2(f), starting with 0.5 g (3 mmol) of (5-bromopyrid-3-ylmethyl)methylamine and 0.4 ml (3.6 mmol) of benzoyl chloride, 0.8 g (90%) of N-(5-bromopyrid-3-ylmethyl)-N-methylbenzamide is obtained.

(f) Preparation of N-[5-(4-Formylphenyl)pyrid-3-ylmethyl]-N-methylbenzamide

In a manner similar to that of Example 1(c), starting with 0.8 g (2.6 mmol) of N45-(4-formylphenyl)pyrid-3-ylmethyl)-N-methylbenzamide and 0.5 g (3.15 mmol) of 4-formylbenzeneboronic acid, 0.8 g (93%) of N-[5-(4-formylphenyl)pyrid-3-ylmethyl]-N-methylbenzamide is obtained after purification on a column of silica eluted with a 7/3 heptane/ethyl acetate mixture.

(g) Preparation of N-{5-[4-(2,4-Dioxothiazolidin-5-ylidenemethyl)phenyl]pyrid-3-ylmethyl}-N-methylbenzamide In a manner similar to that of Example 1(d), starting with 0.8 g (2.4 mmol) of N-[5-(4-formylphenyl)pyrid-3-ylmethyl]-N-methylbenzamide and 0.35 g (2.9 mmol) of 2,4-thiazolidinedione, 0.6 g (60%) of N-{5-[4-(2,4-Dioxothiazolidin-5-ylidenemethyl)phenyl]pyrid-3-ylmethyl}-N-methylbenzamide is obtained.

(h) Synthesis of N-{5-[4-(2,4-Dioxothiazolidin-5-ylmethyl)phenyl]pyrid-3-ylmethyl}-N-methylbenzamide In a manner similar to that of Example 1(e), by hydrogenation of 0.6 g (1.4 mmol) of N-{5-[4-(2,4-Dioxothiazolidin-5-ylidenemethyl)phenyl]pyrid-3-ylmethyl}-N-methylbenzamide, 0.2 g (33%) of N-{5-[4-(2,4-dioxothiazolidin-5-ylmethyl)phenyl]pyrid-3-ylmethyl}-N-methylbenzamide is obtained in the form of a solid with a melting point of 92° C.

$^1$H NMR (δ, CDCl$_3$): 2.96-3.10 (m, 3H); 3.20 (dd, J=22 Hz, J=7 Hz, 1H); 3.58 (dd, J=6.1 Hz, J=22 Hz, 1H); 4.55 (dd, J=6.1 Hz, J=15 Hz, 1H); 4.573-4.84 (m, 2H); 7.30-8.60 (m, 12H); 8.79 (s, 1H).

EXAMPLE 4

Synthesis of N-{3-[5-(2,4-dioxothiazolidin-5-ylmethyl)pyrid-2-yl]benzyl}-N-methyloctanoylamide

(a) Preparation of Ethyl 6-(3-formylphenyl)nicotinate

In a manner similar to that of Example 1(c), starting with 26.3 g (95 mmol) of ethyl 6-iodonicotinate and 18.5 g (123 mmol) of 4-formylbenzeneboronic acid, 6 g (27%) of ethyl 6-(3-formylphenyl)nicotinate are obtained after chromatography on a column of silica eluted with a 7/3 heptane/ethyl acetate mixture.

(b) Preparation of Ethyl 6-(3-methylaminomethylphenyl)nicotinate

In a manner similar to that of Example 3(d), starting with 6.2 g (25.5 mmol) of ethyl 6-(3-formylphenyl)nicotinate and 8.6 g (127.5 mmol) of methylamine hydrochloride, 2.7 g (40%) of ethyl 6-(3-methylaminomethylphenyl)nicotinate are obtained after purification by chromatography on a column of silica eluted with a 95/5/0.5 dichloromethane/methanol/isopropylamine mixture.

(c) Preparation of Ethyl 6-{3-[(methyloctanoylamino)methyl]phenyl}nicotinate

In a manner similar to that of Example 1(b), starting with 2.1 g (7.8 mmol) of ethyl 6-(3-methylaminomethylphenyl)nicotinate and 1.3 g (8 mmol) of octanoyl chloride, 2.9 g (100%) of ethyl 6-{3-[(methyloctanoylamino)methyl]phenyl}nicotinate are obtained after purification by chromatography on a column of silica eluted with a 6/4 heptane/ethyl acetate mixture.

(d) Preparation of N-[3-(5-Hydroxymethylpyrid-2-yl)benzyl]-N-methyloctanoylamide 0.8 g (35 mmol) of lithium borohydride is added slowly to a solution of 3.3 g (9 mmol) of ethyl 6-{3-[(methyloctanoylamino)methyl]phenyl}nicotinate in 35 ml of tetrahydrofuran, cooled beforehand to 0° C. The reaction medium is stirred from 0° C. to room temperature over 24 hours and then poured into a water+ice mixture and extracted with ethyl acetate.

The organic phase is dried over sodium sulfate, filtered and concentrated under vacuum. The residue obtained is purified by chromatography on a column of silica eluted with an 8/2 heptane/ethyl acetate mixture. 1.9 g (61%) of N-[3-(5-hydroxymethylpyrid-2-yl)benzyl]-N-methyloctanoylamide are obtained.

(e) Preparation of N-[3-(5-Formyl pyrid-2-yl)benzyl]-N-methyloctanoylamide 5.5 g (63 mmol) of manganese dioxide are placed in a solution of 2.25 g (6.3 mmol) of N-[3-(5-hydroxymethylpyrid-2-yl)benzyl]-N-methyloctanoylamide in 50 ml of dichloromethane. After stirring at room temperature for 18 hours, the reaction medium is filtered through Celite, the precipitate is washed thoroughly with dichloromethane and the filtrate is concentrated under vacuum. 1.7 g (78%) of N-[3-(5-formylpyrid-2-yl)benzyl]-N-methyloctanoylamide are obtained.

(f) Preparation of N-{3-[5-(2,4-Dioxothiazolidin-5-ylidenemethyl)pyrid-2-yl]benzyl}-N-methyloctanoylamide In a manner similar to that of Example 1(d), starting with 1.7 g (4.8 mmol) of N-[3-(5-formylpyrid-2-yl)benzyl]-N-methyloctanoylamide and 0.6 g (4.8 mmol) of 2,4-thiazolidinedione, 1.4 g (62%) of N-{3-[5-(2,4-dioxothiazolidin-5-ylidenemethyl)pyrid-2-yl]benzyl}-N-methyloctanoylamide are obtained after purification on a column of silica eluted with a 4/6 heptane/ethyl acetate mixture.

(g) Synthesis of N-{3-[5-(2,4-dioxothiazolidin-5-ylmethyl)pyrid-2-yl]benzyl}-N-methyloctanoylamide In a manner similar to that of Example 1(e), by hydrogenation of 400 mg (0.9 mmol) of N-{3-[5-(2,4-dioxothiazolidin-5-ylidenemethyl)pyrid-2-yl]benzyl}-N-methyloctanoylamide, 210 mg (53%) of N-{3-[5-(2,4-dioxothiazolidin-5-ylmethyl)pyrid-2-yl]benzyl}-N-methyloctanoylamide are obtained after purification on a column of silica eluted with a 3/7 heptane/ethyl acetate mixture.

$^1$H NMR (δ, CDCl$_3$): 0.84 (t, J=7 Hz, 3H); 1.21-1.35 (m, 8H); 1.69 (m, 2H); 2.40 (t, J=7.7 Hz, 2H); 2.97 (s, 3H); 3.30 (dd, J=22 Hz, J=7 Hz, 1H); 3.48 (dd, J=6.1 Hz, J=22 Hz, 1H); 4.57 (dd, J=6.1 Hz, J=15 Hz, 1H); 4.57 3-4.68 (m, 2H); 7.20-7.86 (m, 7H); 8.57 (s, 1H).

EXAMPLE 5

Synthesis of 2(S)-Ethoxy-3-(4-{5-[(methyloctanoylamino)methyl]thiophen-3-yl}phenyl)propanoic acid (a) Preparation of (4-Bromothiophen-2-ylmethyl)methylamine In a manner similar to that of Example 3(d), starting with 4.7 g (24.6 mmol) of 4-bromothiophene-2-carbaldehyde and 8.3 g (123 mmol) of methylamine hydrochloride, 1.7 g (33%) of (4-bromothiophen-2-ylmethyl)methylamine are obtained after purification by chromatography on a column of silica eluted with an 8/2 heptane/ethyl acetate mixture.

(b) Preparation of N-(4-Bromothiophen-2-ylmethyl)-N-methyloctanoylamide

In a manner similar to that of Example 1(b), starting with 1.7 g (8.25 mmol) of (4-bromothiophen-2-ylmethyl)methylamine and 1.6 ml (9 mmol) of octanoyl chloride, 2.1 g (80%) of N-(4-bromothiophen-2-ylmethyl)-N-methyloctanoylamide are obtained after purification on a column of silica eluted with an 8/2 heptane/ethyl acetate mixture.

(c) Preparation of N-[4-(4-formylphenyl)thiophen-2-ylmethyl]-N-methyloctanoylamide In a manner similar to that of Example 1(c), starting with 2.1 g (6.3 mmol) of N-(4-bromothiophen-2-ylmethyl)-N-methyloctanoylamide and 1.1 g (7.6 mmol) of 4-formylbenzeneboronic acid, 1.4 g (61%) of N-[4-(4-formylphenyl)thiophen-2-ylmethyl]-N-methyloctanoylamide are obtained after purification by chromatography on a column of silica eluted with a 7/3 heptane/ethyl acetate mixture.

(d) Preparation of N-(4-{4-[3-(4-benzyl-2-oxooxazolidin-3-yl)-2(S)-ethoxy-1(S)-hydroxy-3-oxopropyl]phenyl}thiophen-2-ylmethyl)-N-methyloctanoylamide Preparation of 4(S)-benzyl-3-(2-ethoxyacetyl)oxazolidin-2-one 93 ml (232 mmol) of butyllithium are added dropwise to a solution of 41 g (232 mmol) of S-(−)-4-benzyloxazolidin-2-one in 600 ml of tetrahydrofuran cooled beforehand to −78°

C. After stirring for 30 minutes, 35 g (279 mmol) of ethoxyacetyl chloride are added dropwise. After stirring for 1 hour at −78° C., the reaction medium is stirred at room temperature for 18 hours. The reaction medium is evaporated to dryness, taken up in ethyl acetate and washed with water. The organic phase is dried over sodium sulfate, filtered and evaporated. The residue obtained is purified by chromatography on a column of silica eluted with an 8/2 heptane/ethyl acetate mixture. 54 g (90%) of 4(S)-benzyl-3-(2-ethoxyacetyl)oxazolidin-2-one are obtained.

Preparation of N-(4-{4-[3-(4-benzyl-2-oxooxazolidin-3-yl)-2(S)-ethoxy-1(S)-hydroxy-3-oxopropyl]phenyl}thiophen-2-ylmethyl)-N-methyloctanoylamide 5.9 ml (5.9 mmol) of dibutylboron triflate are added dropwise to a solution of 1.2 g (4.7 mmol) of 4(S)-benzyl-3-(2-ethoxyacetyl)oxazolidin-2-one in 20 ml of dichloromethane, cooled beforehand to 0° C., followed by addition of 1 ml (5.9 mmol) of diisopropylethylamine. The reaction medium is stirred at 0° C. for 30 minutes and then cooled to −78° C. and 1.4 g (3.9 mmol) of N-[4-(4-formylphenyl)thiophen-2-ylmethyl]-N-methyloctanoylamide in 15 ml of dichloromethane are added dropwise. Stirring is continued at −78° C. for 1 hour and then at room temperature for 2 hours 30 minutes. The reaction medium is cooled to 0° C. and 11 ml of a pH 7 buffer solution in 11 ml of methanol are added, followed by addition of 11 ml of 30% aqueous hydrogen peroxide solution in 11 ml of methanol. After stirring at 0° C. for 1 hour 30 minutes, water is added and the reaction medium is extracted with dichloromethane. The organic phase is dried over magnesium sulfate, filtered and evaporated. The residue obtained is purified by chromatography through a column of silica eluted with a 6/4 heptane/ethyl acetate mixture. 1.8 g (75%) of N-(4-{4-[3-(4-benzyl-2-oxooxazolidin-3-yl)-2-ethoxy-1-hydroxy-3-oxopropyl]phenyl}thiophen-2-ylmethyl)-N-methyloctanoylamide are obtained.

(e) Preparation of (4-{4-[3-(4-Benzyl-2-oxooxazolidin-3-yl)-2(S)-ethoxy-3-oxopropyl]phenyl}thiophen-2-ylmethyl)methyloctanoylamide 0.9 ml (1.8 mmol) of sodium bis(trimethylsilyl)amide is added to a solution of 1 g (1.6 mmol) of N-(4-{4-[3-(4-benzyl-2-oxooxazolidin-3-yl)-2-ethoxy-1-hydroxy-3-oxopropyl]phenyl}thiophen-2-ylmethyl)-N-methyloctanoylamide in 20 ml of dichloromethane, cooled beforehand to −78° C. After stirring at −78° C. for 1 hour, 0.25 ml (1.8 mmol) of phenyl chlorothionoformate is added and the reaction medium is stirred at −78° C. for 1 hour and then at room temperature for 2 hours. After adding water, the reaction medium is extracted with dichloromethane. The organic phase is evaporated under vacuum. The residue obtained is placed in 30 ml of toluene, and 13 mg (0.1 mmol) of 2,2'-azobis(2-methylpropionitrile) and 0.65 ml (2.4 mmol) of tributyltin hydride are then added. The reaction medium is heated at 110° C. for 30 minutes. The reaction medium is cooled, diluted with ethyl acetate and washed with water. The organic phase is dried over magnesium sulfate, filtered and evaporated. The residue obtained is purified by chromatography on a column of silica eluted with a 6/4 heptane/ethyl acetate mixture. 0.65 g (65%) of (4-{4-[3-(4-benzyl-2-oxooxazolidin-3-yl)-2-ethoxy-3-oxopropyl]phenyl}thiophen-2-ylmethyl)methyloctanoylamide is obtained.

(f) Synthesis of 2(S)-Ethoxy-3-(4-{5-[(methyloctanoylamino)methyl]thiophen-3-yl}phenyl)propanoic acid 1.3 ml (1.6 mmol) of aqueous 0.5 N lithium hydroxide solution are added to a solution of 0.6 g (1 mmol) of (4-{4-[3-(4-benzyl-2-oxooxazolidin-3-yl)-2-ethoxy-3-oxopropyl]phenyl}thiophen-2-ylmethyl)methyloctanoylamide in 10 ml of tetrahydrofuran, cooled to 0° C. After stirring at 0° C. for 30 minutes, the reaction medium is stirred at room temperature for 1 hour 30 minutes. Water and ethyl acetate are added to the reaction medium, and an aqueous sodium hydroxide solution is then added until pH 8-9 is obtained. After extraction and separation of the phases, repeated twice, the product is in the aqueous phase. This aqueous phase is acidified to pH 3-4 with aqueous 1N hydrochloric acid solution, extracted with ethyl acetate, dried over magnesium sulfate, filtered and evaporated. The residue obtained is purified by chromatography on a column of silica eluted with a 98/2 dichloromethane/methanol mixture. 0.35 g (76%) of 2(S)-ethoxy-3-(4-{5-[(methyloctanoylamino)methyl]thiophen-3-yl}phenyl)propanoic acid is obtained.

$^1$H NMR (δ, CDCl$_3$): 0.89 (m, 3H); 1.19 (t, J=6.8 Hz, 3H); 1.30-1.34 (m, 8H); 1.69 (m, 2H); 2.36-2.50 (m, 2H); 3.03 (s, 3H); 3.06 (m, 1H); 3.15 (dd, J=4.0 Hz, J=14.0 Hz, 1H); 3.41-3.45 (m, 1H); 4.09-4.12 (m, 1H); 4.10 (dd, J=4.0 Hz, J=7.0 Hz, 1H); 4.69-4.74 (m, 2H); 7.19-7.35 (m, 4H); 7.49 (d, J=7.9 Hz, 2H).

EXAMPLE 6

Synthesis of 2(S)-Ethoxy-3-(4-{5-[(methyloctanoylamino)methyl]thiophen-2-yl}phenyl)propanoic acid (a) Preparation of (5-Bromothiophen-2-ylmethyl)-N-methylamine 14 g (209 mmol) of methylamine hydrochloride are added to a solution of 5 g (42 mmol) of 5-bromothiophene-2-carboxaldehyde in 80 ml of ethanol and 40 ml of methanol. The reaction medium is cooled to 0° C. and 5.8 g (83.8 mmol) of sodium cyanoborohydride are added. The reaction medium is stirred at 0° C. for 5 hours, hydrolysed and diluted with ethyl acetate. The organic phase is washed with water, dried over magnesium sulfate, filtered and evaporated. The residue obtained is taken up in a 70/30 heptane/dichloromethane mixture and then filtered. 6.7 g of crude residue are obtained.

(b) Preparation of (5-Bromothiophen-2-ylmethyl)-N-methyloctanoylamide 6.2 ml (35.7 mmol) of octanoyl chloride are added dropwise to a solution of 6.7 g (32.5 mmol) of crude residual (5-bromothiophen-2-ylmethyl)-N-methylamine obtained in 6a, in 120 ml of tetrahydrofuran and 5 ml (35.7 mmol) of triethylamine, cooled beforehand to 0° C. The reaction medium is stirred for 30 minutes at 0° C. and then for 4 hours at room temperature. After addition of water, the reaction medium is extracted with ethyl acetate. The organic phase is washed with aqueous sodium chloride solution, isolated and then evaporated. The residue obtained is purified by chromatography on a column of silica eluted with an 8/2 and then 7/3 heptane/ethyl acetate mixture. 1.2 g (11%) of (5-bromothiophen-2-ylmethyl)-N-methyloctanoylamide are obtained.

(c) Preparation of [5-(4-Formylphenyl)thiophen-2-ylmethyl]-N-methyloctanoylamide 5.4 ml (10.8 mmol) of aqueous potassium carbonate solution are added to a solution of 1.2 g (3.6 mmol) of (5-bromothiophen-2-ylmethyl)-N-methyloctanoylamide and 0.65 g (4.3 mmol) of 4-formylbenzeneboronic acid in 20 ml of toluene. The reaction medium is degassed and 0.12 g (0.1 mmol) of tetrakis(triphenylphosphine)palladium is then added. The reaction medium is stirred at 90° C. for 5 hours. After addition of water, the reaction medium is extracted with ethyl acetate. The organic phase is dried over magnesium sulfate, filtered and evaporated. The residue obtained is purified by chromatography on a column of silica eluted with an 8/2 and then 7/3 heptane/ethyl acetate mixture. 0.25 g (19%) of [5-(4-formylphenyl)thiophen-2-ylmethyl]-N-methyloctanoylamide is obtained.

(d) Preparation of N-(5-{4-[3-(4(S)-benzyl-2-oxooxazolidin-3-yl)-2(S)-ethoxy-1(S)-hydroxy-3-oxopropyl]phenyl}thiophen-2-ylmethyl)-N-methyloctanoylamide 2.26 ml (2.26 mmol) of a solution of dibutylborane triflate are added dropwise to a solution of 0.48 g (1.8 mmol) of [5-(4-formylphenyl)thiophen-2-ylmethyl]-N-methyloctanoylamide in 12 ml of dichloromethane, cooled to 0° C., followed by addition of 0.39 ml (2.26 mmol) of diisopropylethylamine. The reaction medium is stirred at 0° C. for 30 minutes and then cooled to −78° C. A solution of 0.54 g (1.5 mmol) of 4(S)-benzyl-3-(2-ethoxyacetyl)oxazolidin-2-one (prepared as described in Example 5d) in 5 ml of dichloromethane is added dropwise. The reaction medium is stirred at −78° C. for 1 hour and then at room temperature for 2 hours 30 minutes. After cooling to 0° C., a mixture of 4 ml of a pH 7 buffer solution and 4 ml of methanol is added dropwise, followed by dropwise addition of a mixture of 4 ml of aqueous 30% hydrogen peroxide solution and 4 ml of methanol. The reaction medium is stirred for 1 hour at room temperature, water is added and the medium is extracted with dichloromethane. The dichloromethane phase is dried over magnesium sulfate, filtered and evaporated. The residue obtained is purified by chromatography on a column of silica eluted with a 7/3 and then 6/4 heptane/ethyl acetate mixture. 0.62 g (66%) of N-(5-{4-[3-(4(S)-benzyl-2-oxooxazolidin-3-yl)-2(S)-ethoxy-1(S)-hydroxy-3-oxopropyl]phenyl}thiophen-2-ylmethyl)-N-methyloctanoylamide is obtained.

(e) Preparation of O-[3-(4(S)-Benzyl-2-oxooxazolidin-3-yl)-2(S)-ethoxy-1-(4-{5-[(methyloctanoylamino)methyl]thiophen-2-yl}phenyl)-3-oxopropyl] O-phenyl thiocarbonate 0.55 ml (1.1 mmol) of sodium trimethylsilylamide is added to a solution of 0.62 g (1 mmol) of N-(5-{4-[3-(4(S)-benzyl-2-oxooxazolidin-3-yl)-2(S)-ethoxy-1(S)-hydroxy-3-oxopropyl]phenyl}thiophen-2-ylmethyl)-N-methyloctanoylamide in 15 ml of tetrahydrofuran, cooled beforehand to −78° C., and the reaction medium is stirred for 1 hour at −78° C., followed by addition of 0.15 ml (1.1 mmol) of phenyl chlorothionoformate. The reaction medium is again stirred at −78° C. for 1 hour and then at room temperature for 1 hour. After addition of water, the reaction medium is extracted with dichloromethane. The organic phase is dried over magnesium sulfate, filtered and evaporated. The crude product is used in step f.

(f) Preparation of (5-{4-[3-(4(S)-benzyl-2-oxooxazolidin-3-yl)-2(S)-ethoxy-3-oxopropyl]phenyl}thiophen-2-ylmethyl)-N-methyloctanoylamide The crude product obtained from step e is placed in 15 ml of toluene with 0.01 g (0.05 mmol) of AiBN and 0.4 ml (1.5 mmol) of tributyltin hydride. After heating at 110° C. for 45 minutes, the reaction has not changed. 0.56 ml (2.1 mmol) of tributyltin hydride is added and the reaction medium is stirred at 110° C. for 2 hours. Water is added and the reaction medium is extracted with ethyl acetate. The organic phase is washed with saturated sodium chloride solution, dried over magnesium sulfate, filtered and evaporated. The residue obtained is purified by chromatography on a column of silica eluted with an 8/2 and then 7/3 heptane/ethyl acetate mixture. 0.27 g (45%) of (5-{4-[3-(4(S)-benzyl-2-oxooxazolidin-3-yl)-2(S)-ethoxy-3-oxopropyl]phenyl}thiophen-2-ylmethyl)-N-methyloctanoylamide is obtained.

(g) Synthesis of 2(S)-Ethoxy-3-(4-{5-[(methyloctanoylamino)methyl]thiophen-2-yl}phenyl)propanoic acid A solution of 0.27 g (0.45 mmol) of (5-{4-[3-(4(S)-benzyl-2-oxooxazolidin-3-yl)-2(S)-ethoxy-3-oxopropyl]phenyl}thiophen-2-ylmethyl)-N-methyloctanoylamide in 10 ml of tetrahydrofuran and 1.3 ml (0.67 mmol) of aqueous 0.5M sodium hydroxide solution is stirred from 0° C. to room temperature over 18 hours. After addition of water, a first extraction is performed with ethyl acetate. The aqueous phase obtained is acidified to pH 6 with aqueous hydrochloric acid solution and then extracted with ethyl acetate. The organic phase is washed with saturated sodium chloride solution, filtered and evaporated. The residue obtained is purified by chromatography on a column of silica eluted with a 5/5 heptane/ethyl acetate mixture. 0.06 g (30%) of 2(S)-ethoxy-3-(4-{5-[(methyloctanoylamino)methyl]thiophen-2-yl}phenyl)propanoic acid is obtained.

$^1$H NMR (δ CDCl$_3$): 0.88 (t, J=6.7 Hz, 3H); 1.18 (t, J=7.0 Hz, 3H); 1.28-1.35 (m, 8H); 1.67-1.70 (m, 2H); 2.34-2.48 (m, 2H); 3.00 (m, 1H); 3.01 (s, 3H); 3.14 (m, 1H); 3.47 (m, 1H); 3.63 (m, 1H); 4.11 (m, 1H); 4.69 (m, 2H); 6.90 (dd, J=17 Hz, J=3.6 Hz, 1H); 7.14 (dd, J=3.6 Hz, J=13 Hz, 1H); 7.27 (d, J=8.1 Hz, 2H); 7.50 (d, J=8.1 Hz, 2H).

EXAMPLE 7

Synthesis of 2(S)-Ethoxy-3-{4-[2-(3-heptyl-1-methylureido)thiazol-5-yl]phenyl}propanoic acid

(a) Preparation of N-(5-Bromothiazol-2-yl)acetamide 5.9 ml (42.3 mmol) of acetic anhydride are added to a solution of 10 g (38.5 mmol) of 2-amino-5-bromothiazole hydrobromide in 100 ml of dichloromethane and 11 ml (77 mmol) of triethylamine, cooled to 0° C. The reaction medium is stirred for 30 minutes at 0° C. and then for 18 hours at room temperature. After addition of water, the pH is adjusted to pH 8 with aqueous 1M sodium hydroxide solution and the reaction medium is extracted with dichloromethane. The dichloromethane phase is dried over magnesium sulfate, filtered and evaporated. The residue obtained is used in step b without purification.

(b) Preparation of
N-(5-Bromothiazol-2-yl)-N-methylacetamide 1.9 g (14 mmol) of potassium carbonate and 3.94 ml (63.3 mmol) of methyl iodide are added to a solution of 2.8 g (12.7 mmol) of N-(5-bromothiazol-2-yl)acetamide in 50 ml of acetone. The reaction medium is refluxed for 3 hours. After addition of water, the reaction medium is extracted with ethyl acetate. The organic phase is washed with saturated aqueous sodium chloride solution, dried over magnesium sulfate, filtered and evaporated. The residue obtained is purified by chromatography on a column of silica eluted with a 7/3 heptane/ethyl acetate mixture. 1.1 g (36%) of N-(5-Bromothiazol-2-yl)-N-methylacetamide are obtained.

(c) Preparation of Methyl
3-(4-bromophenyl)-2(S)-hydroxypropanoate 100 ml (170 mmol) of a 1.7 M solution of tert-butyllithium in pentane are added dropwise to a solution of 48 g (204 mmol) of 1,4-dibromobenzene in 160 ml of tert-butyl dimethyl ether, cooled to −30° C., followed by addition of 7.3 g (82 mmol) of copper cyanide. The reaction medium is stirred for 15 minutes and a solution of 6 ml (68 mmol) of (S)-methyl glycidate in 10 ml of tert-butyl dimethyl ether is then added. After stirring for 20 minutes at −30° C., the reaction medium is hydrolysed with 150 ml of saturated aqueous ammonium chloride solution and extracted with ethyl acetate. The organic phase is washed with saturated aqueous sodium chloride solution, dried over magnesium sulfate, filtered and evaporated. The residue obtained is purified by chromatography on a column of silica eluted with heptane, and the polarity is then increased up to a 6/4 heptane/ethyl acetate mixture. 23.5 g (44%) of methyl 3-(4-bromophenyl)-2(S)-hydroxypropanoate are obtained.

(d) Preparation of Methyl
3-(4-bromophenyl)-2(S)-ethoxypropanoate 11 ml of ethyl iodide are added dropwise to a solution of 23.5 g (91 mmol) of methyl 3-(4-bromophenyl)-2(S)-hydroxypropanoate and 35.6 g (155 mmol) of silver(I) oxide in 120 ml of isopropyl ether. The reaction medium is heated at 70° C. overnight. 10 g (45 mmol) of silver oxide and 3.7 ml (45 mmol) of ethyl iodide are added and the reaction medium is heated for a further 4 hours and then filtered through Celite, the precipitate is rinsed with ethyl acetate and the filtrate is concentrated under vacuum. The residue obtained is purified by chromatography on a column of silica eluted with a 95/5 and then 90/10 heptane/ethyl acetate mixture. 20 g (79%) of methyl 3-(4-bromophenyl)-2(S)-ethoxypropanoate are obtained.

(e) Preparation of Methyl 2(S)-ethoxy-3-[4-(4,4,5,5-tetramethyl-[1,3,2]dioxaborolan-2-yl)phenyl]propanoate A solution of 8.3 g (28.9 mmol) of methyl 3-(4-bromophenyl)-2(S)-ethoxypropanoate, 11 g (43.3 mmol) of bis-pinacoldiborane and 8.5 g (86.7 mmol) of potassium acetate in 250 ml of dimethylformamide is degassed for 15 minutes, and 0.94 g (1.2 mmol) of diphenylphosphinoferrocenepalladium chloride ($PdCl_2dppf$) is then added. The reaction medium is heated at 60° C. for 20 hours. After cooling, water is added and the reaction medium is extracted with ethyl acetate. The ethyl acetate phase is washed with saturated sodium chloride solution, dried over magnesium sulfate, filtered and evaporated. The residue obtained is purified by chromatography on a column of silica eluted with a 95/5 and then 90/10 heptane/ethyl acetate mixture. 7 g (73%) of methyl 2(S)-ethoxy-3-[4-(4,4,5,5-tetramethyl[1,3,2]dioxaborolan-2-yl)phenyl]propanoate are obtained.

(f) Preparation of Methyl 3-{4-[2-(acetylmethylamino)thiazol-5-yl]phenyl}-2(S)-ethoxypropanoate 0.2 g (0.3 mmol) of diphenylphosphinoferrocenepalladium chloride ($PdCl_2dppf$) is added to a solution of 1 g (4.5 mmol) of N-(5-bromothiazol-2-yl)-N-methylacetamide, 1.8 g (6.8 mmol) of methyl 2(S)-ethoxy-3-[4-(4,4,5,5-tetramethyl[1,3,2]dioxaborolan-2-yl)phenyl]propanoate and 1 g (6.8 mmol) of caesium fluoride in 50 ml of ethylene glycol dimethyl ether, degassed beforehand. The reaction medium is heated at 80° C. for 18 hours. After cooling, water is added and the reaction medium is extracted with ethyl acetate. The ethyl acetate phase is washed with saturated sodium chloride solution, dried over magnesium sulfate, filtered and evaporated. The residue obtained is purified by chromatography on a column of silica eluted with a 70/30 and then 60/40 heptane/ethyl acetate mixture. 0.6 g (37%) of methyl 3-{4-[2-(acetylmethylamino)thiazol-5-yl]phenyl}-2(S)-ethoxypropanoate is obtained in the form of a beige-colored solid with a melting point of 123° C.

(g) Preparation of 2(S)-Ethoxy-3-[4-(2-methylaminothiazol-5-yl)phenyl]propanoic acid 0.6 g (1.6 mmol) of methyl 3-{4-[2-(acetylmethylamino)thiazol-5-yl]phenyl}-2(S)-ethoxypropanoate in 25 ml of methanol and 2.4 ml (2.4 mmol) of aqueous 1M sodium hydroxide solution are heated at 60° C. for 18 hours. The reaction medium is cooled, diluted with water, acidified to pH 4-5 and then extracted with ethyl acetate and n-butanol. The organic phase is washed with saturated sodium chloride solution, dried over magnesium sulfate, filtered and evaporated. The residue obtained is used in step h without purification.

(h) Preparation of Methyl 2(S)-ethoxy-3-[4-(2-methylaminothiazol-5-yl)phenyl]propanoate 0.5 g (1.6 mmol) of 2(S)-ethoxy-3-[4-(2-methylaminothiazol-5-yl)phenyl]propanoic acid in 10 ml of methanol and a few drops of sulfuric acid is heated at 60° C. for 2 hours. The reaction medium is cooled, diluted with water, neutralized to pH 7 with aqueous 1M sodium hydroxide solution and then extracted with ethyl acetate. The organic phase is washed with saturated sodium chloride solution, dried over magnesium sulfate, filtered and evaporated. The residue obtained is purified by chromatography on a column of silica eluted with a 50/50 heptane/ethyl acetate mixture. 0.34 g (67%) of methyl 2(S)-ethoxy-3-[4-(2-methylaminothiazol-5-yl)phenyl]propanoate is obtained in the form of a yellow solid.

(i) Preparation of Methyl 2(S)-ethoxy-3-{4-[2-(3-heptyl-1-methylureido)thiazol-5-yl]phenyl}propanoate 0.17 ml (1 mmol) of heptyl isocyanate is added to a solution of 0.17 g (0.5 mmol) of 2(S)-ethoxy-3-[4-(2-methylaminothiazol-5-yl)phenyl]propanoate in 10 ml of dichloromethane. The reaction medium is stirred at room temperature for 20 hours. The reaction medium is diluted with water and then extracted with dichloromethane. The organic phase is dried over magnesium sulfate, filtered and evaporated. The residue obtained is purified by thin-layer chromatography on silica eluted with a 50/50 heptane/ethyl acetate mixture. 0.07 g (30%) of methyl 2(S)-ethoxy-3-{4-[2-(3-heptyl-1-methylureido)thiazol-5-yl]phenyl}propanoate is obtained.

(j) Synthesis of 2(S)-Ethoxy-3-{4-[2-(3-heptyl-1-methylureido)thiazol-5-yl]phenyl}propanoic acid 0.07 g (0.15 mmol) of methyl 2(S)-ethoxy-3-{4-[2-(3-heptyl-1-methylureido)thiazol-5-yl]phenyl}propanoate is placed in 3 ml of tetrahydrofuran and 0.2 ml (0.2 mmol) of aqueous 1M lithium hydroxide solution. The reaction medium is stirred at room temperature for 18 hours. 0.07 ml of aqueous 1M lithium hydroxide solution is added and the medium is heated for a further 5 hours. The reaction medium is diluted with water, acidified to pH 4-5 and then extracted with ethyl acetate. The organic phase is washed with saturated sodium chloride solution, dried over magnesium sulfate, filtered and evaporated. 55 mg (82%) of 2(S)-ethoxy-3-{4-[2-(3-heptyl-1-methylureido)thiazol-5-yl]phenyl}propanoic acid are obtained in the form of a white solid with a melting point of 97° C.

$^1$H NMR (δ CDCl$_3$): 0.90 (t, J=6.7 Hz, 3H); 1.22 (t, J=7.0 Hz, 3H); 1.28-1.38 (m, 8H); 1.60 (m, 2H); 3.08 (dd, J=7.5 Hz, J=4.1 Hz, 1H); 3.15 (dd, J=4.1 Hz, J=14 Hz, 1H); 3.37 (m, 2H); 3.47 (s, 3H); 3.49 (m, 1H); 3.66 (m, 1H); 4.12 (m, 1H); 7.29 (d, J=8.2 Hz, 2H); 7.43 (d, J=8.2 Hz, 2H); 7.52 (s, 1H); 9.24 (s, 1H).

EXAMPLE 8

Synthesis of 2(S)-Ethoxy-3-{4-[2-(1-methyl-3-pentylureido)thiazol-5-yl]phenyl}propanoic acid (a) Preparation of Methyl 2(S)-ethoxy-3-{4-[2-(1-methyl-3-pentylureido)thiazol-5-yl]phenyl}propanoate In a manner similar to that of Example 7i, starting with 0.17 g (0.53 mmol) of methyl 2(S)-ethoxy-3-[4-(2-methylaminothiazol-5-yl)phenyl]propionate and 0.14 ml (1.1 mmol) of pentyl isocyanate, 0.06 g (26%) of methyl 2(S)-ethoxy-3-{4-[2-(1-methyl-3-pentylureido)thiazol-5-yl]phenyl}propanoate is obtained.

(b) Synthesis of 2(S)-Ethoxy-3-{4-[2-(1-methyl-3-pentylureido)thiazol-5-yl]phenyl}propanoic acid In a manner similar to that of Example 7j, starting with 0.06 g (0.14 mmol) of methyl 2(S)-ethoxy-3-{4-[2-(1-methyl-3-pentylureido)thiazol-5-yl]phenyl}propanoate and 0.2 ml (0.2 mmol) of aqueous 1M lithium hydroxide solution, 0.05 g (86%) of 2(S)-ethoxy-3-{4-[2-(1-methyl-3-pentylureido)thiazol-5-yl]phenyl}propanoic acid is obtained in the form of a white solid with a melting point of 114° C.

$^1$H NMR (δ CDCl$_3$): 0.93 (t, J=6.7 Hz, 3H); 1.22 (t, J=7.0 Hz, 3H); 1.36-1.40 (m, 4H); 1.63 (m, 2H); 3.06 (dd, J=7.5 Hz, J=4.1 Hz, 1H); 3.15 (dd, J=4.1 Hz, J=14 Hz, 1H); 3.37 (m, 2H); 3.47 (s, 3H); 3.50 (m, 1H); 3.66 (m, 1H); 4.12 (m, 1H); 7.29 (d, J=8.4 Hz, 2H); 7.43 (d, J=8.4 Hz, 2H); 7.53 (s, 1H); 9.25 (s, 1H).

EXAMPLE 9

Synthesis of 2(S)-Ethoxy-3-{4-[6-(3-heptyl-1-methylureido)pyrid-2-yl]phenyl}propanoic acid (a) Preparation of tert-butyl (6-Bromopyrid-2-yl)carbamate 62 g (284 mmol) of di-tert-butyl dicarbonate diluted in 200 ml of dichloromethane are added dropwise to a solution of 49.2 g (284 mmol) of 2-amino-6-bromopyridine, 43.4 ml (312 mmol) of triethylamine and 3.5 g (28.4 mmol) of 4-dimethylaminopyridine in 400 ml of dichloromethane. The reaction medium is stirred at room temperature for 18 hours. After addition of water and extraction with dichloromethane, the organic phase is dried over magnesium sulfate, filtered and evaporated. The residue obtained is purified by thin-layer chromatography on silica eluted with a 95/5 heptane/ethyl acetate mixture. 39 g (50%) of tert-butyl (6-bromopyrid-2-yl)carbamate are obtained in the form of a white solid.

(b) Preparation of tert-butyl 6-Bromopyrid-2-yl-N-methylcarbamate 6.9 g (17.2 mmol) of 60% sodium hydride in oil are added portionwise to a solution of 39 g (14.3 mmol) of tert-butyl (6-bromopyrid-2-yl)carbamate in 400 ml of dimethylformamide. After stirring for 20 minutes at room temperature, 17.8 ml (28.6 mmol) of methyl iodide are added dropwise. The reaction medium is stirred at room temperature for 18 hours, taken up in water and extracted with ethyl acetate. The organic phase is dried over magnesium sulfate, filtered and evaporated.

(c) Preparation of (6-Bromopyrid-2-yl)-N-methylamine 2.1 g (7.3 mmol) of tert-butyl 6-bromopyrid-2-yl-N-methylcarbamate, 1.6 ml (21.9 mmol) of trifluoroacetic acid and 25 ml of dichloromethane are stirred at room temperature for 20 hours.

After addition of water, the reaction medium is extracted with dichloromethane. The organic phase is washed with aqueous sodium hydroxide solution and then washed with water, dried over magnesium sulfate, filtered and evaporated. 1.4 g (100%) of (6-bromopyrid-2-yl)-N-methylamine are obtained.

(d) Preparation of 1-(6-Bromopyrid-2-yl)-3-heptyl-1-methylurea 1 g (5.35 mmol) of (6-bromopyrid-2-yl)-N-methylamine, 1 ml of diisopropylethylamine and 1.6 g (8 mmol) of 4-nitrophenyl chloroformate are heated at 130° C. for 15 minutes by microwave. 1.2 ml (8 mmol) of heptylamine and 7 ml of dimethylformamide are added and the reaction medium is heated at 130° C. for a further 5 minutes. The residue obtained is purified by thin-layer chromatography on silica eluted with a 70/30 heptane/ethyl acetate mixture. 1.4 g (80%) of 1-(6-bromopyrid-2-yl)-3-heptyl-1-methylurea are obtained in the form of a yellow solid.

(e) Preparation of Methyl 2(S)-ethoxy-3-{4-[6-(3-heptyl-1-methylureido)pyrid-2-yl]phenyl}propanoate 3.2 g (9.7 mmol) of 1-(6-bromopyrid-2-yl)-3-heptyl-1-methylurea, 4.2 g (12.6 mmol) of methyl 2(S)-ethoxy-3-[4-(4,4,5,5-tetramethyl[1,3,2]dioxaborolan-2-yl)phenyl]propanoate (prepared as in Example 7e) and 4.4 g (29.1 mmol) of caesium fluoride are placed in 200 ml of dimethoxyethylene glycol. The reaction medium is degassed, 0.23 g (0.3 mmol) of dichlorodiphenylphosphinoferrocenepalladium is then added and the reaction medium is stirred at 80° C. for 18 hours. After addition of water, the reaction medium is extracted with ethyl acetate. The organic phase is washed with water, with saturated sodium chloride solution, dried over magnesium sulfate, filtered and evaporated. The residue obtained is purified by thin-layer chromatography on silica eluted with an 80/20 heptane/ethyl acetate mixture. 2 g (45%) of methyl 2(S)-ethoxy-3-{4-[6-(3-heptyl-1-methylureido)pyrid-2-yl]phenyl}propanoate are obtained.

(f) Synthesis of 2(S)-Ethoxy-3-{4-[6-(3-heptyl-1-methylureido)pyrid-2-yl]phenyl}propanoic acid 1.1 g (2.4 mmol) of methyl 2(S)-ethoxy-3-{4-[6-(3-heptyl-1-methylureido)pyrid-2-yl]phenyl}propanoate, 20 ml of tetrahydrofuran and 3.6 ml (3.6 mmol) of aqueous 1M lithium hydroxide solution are stirred at room temperature for 5 hours. After addition of water and ethyl acetate, the reaction medium is acidified to pH 5.5 with aqueous 1N acetic acid solution. The organic phase is washed with water, dried over magnesium sulfate, filtered and evaporated. 1 g (95%) of 2(S)-ethoxy-3-{4-[6-(3-heptyl-1-methylureido)pyrid-2-yl]phenyl}propanoic acid is obtained in the form of a viscous syrup.

$^1$H NMR (δ CDCl$_3$): 0.87 (t, J=6.7 Hz, 3H); 1.21 (t, J=7.0 Hz, 3H); 1.26-1.37 (m, 8H); 1.61 (m, 2H); 3.10 (dd, J=7.5 Hz, J=4.1 Hz, 1H); 3.21 (dd, J=4.1 Hz, J=14 Hz, 1H); 3.39 (m, 2H); 3.47 (s, 3H); 3.49 (m, 1H); 3.66 (m, 1H); 4.16 (m, 1H); 6.94 (d, J=8.4 Hz, 1H); 7.28-7.40 (m, 3H); 7.75-7.82 (m, 3H).

EXAMPLE 10

Synthesis of 2(S)-Ethoxy-3-{4-[6-(3-heptyl-1-methylureido)pyrid-2-yl]phenyl}propanoic acid hydrochloride 2.5 ml (2.5 mmol) of ethanolic 1M hydrochloric acid solution are added dropwise to a solution of 1.1 g (2.5 mmol) of 2(S)-ethoxy-3-{4-[6-(3-heptyl-1-methylureido)pyrid-2-yl]phenyl}propanoic acid in 2 ml of ethanol, cooled to 0° C. The reaction medium precipitates. After filtration, the precipitate is washed with acetone and with ethyl ether and then dried. After hot recrystallization from a 9/1 acetone/water mixture, 0.6 g (60%) of 2(S)-ethoxy-3-{4-[6-(3-heptyl-1-methylureido)pyrid-2-yl]phenyl}propanoic acid hydrochloride is obtained in the form of a white solid with a melting point of 166° C.

$^1$H NMR (δ CDCl$_3$): 0.77 (t, J=6.7 Hz, 3H); 1.07 (t, J=7.0 Hz, 3H); 1.10-1.25 (m, 8H); 1.58 (m, 2H); 3.00 (dd, J=7.5 Hz, J=4.1 Hz, 1H); 3.08 (dd, J=4.1 Hz, J=14 Hz, 1H); 3.26 (m, 2H); 3.27 (m, 1H); 3.60 (s, 3H); 3.61 (m, 1H); 3.96 (dd, J=4.1 Hz, J=8.4 Hz, 1H); 7.20 (m, 1H); 7.41 (d, J=8.1 Hz, 2H); 7.44 (m, 1H); 7.66 (d, J=8.1 Hz, 2H); 8.03 (m, 1H); 9.00 (m, 2H).

EXAMPLE 11

Synthesis of 2(S)-Ethoxy-3-{4-[5-(3-heptyl-1-methylureido)-2-methyl-2H-[1,2,4]triazol-3-yl]phenyl}propanoic acid (a) Preparation of 5-Bromo-1-methyl-3-nitro-1H-[1,2,4]triazole 1.1 g (28.5 mmol) of 60% sodium hydride are added to a solution of 5 g (25.9 mmol) of 5-bromo-3-nitro-1H-[1,2,4]triazole in 80 ml of dimethylformamide, cooled beforehand to 0° C. The reaction medium is stirred for 20 minutes and 8 ml (129.5 mmol) of methyl iodide are then added. After stirring at room temperature for 18 hours, water is added and the reaction medium is extracted with ethyl acetate. The organic phase is washed thoroughly with water, with saturated sodium chloride solution, dried over magnesium sulfate, filtered and evaporated. The residue obtained is purified by thin-layer chromatography on silica eluted with a 75/25 heptane/ethyl acetate mixture. 3.2 g (60%) of 5-bromo-1-methyl-3-nitro-1H-[1,2,4]triazole are obtained.

(b) Preparation of Methyl 2(S)-ethoxy-3-[4-(2-methyl-5-nitro-2H-[1,2,4]triazol-3-yl)phenyl]propanoate In a manner similar to that of Example 9(e), starting with 0.9 g (4.35 mmol) of 5-bromo-1-methyl-3-nitro-1H-[1,2,4]triazole and 1.9 g (6.5 mmol) of methyl 2(S)-ethoxy-3-[4-(4,4,5,5-tetramethyl[1,3,2]dioxaborolan-2-yl)phenyl]propanoate, 0.9 g (62%) of methyl 2(S)-ethoxy-3-[4-(2-methyl-5-nitro-2H[1,2,4]triazol-3-yl)phenyl]propanoate is obtained in the form of a white solid with a melting point of 119° C.

(c) Preparation of Methyl 3-[4-(5-amino-2-methyl-2H-[1,2,4]triazol-3-yl)phenyl]-2(S)-ethoxypropanoate 0.4 g (0.4 mass equivalent) of 10% palladium-on-charcoal is added to a solution of 0.9 g (2.7 mmol) of methyl 2(S)-ethoxy-3-[4-(2-methyl-5-nitro-2H-[1,2,4]triazol-3-yl)phenyl]propanoate in 40 ml of ethanol and 10 ml of methanol, degassed beforehand, and the reaction medium is placed under an atmospheric pressure of hydrogen for 3 hours. After filtration through Celite and washing with ethyl acetate, the filtrate is evaporated under vacuum. 0.82 g (100%) of methyl 3-[4-(5-amino-2-methyl-2H-[1,2,4]triazol-3-yl)phenyl]-2(S)-ethoxypropanoate is obtained.

(d) Preparation of Methyl 2(S)-ethoxy-3-[4-(2-methyl-5-methylamino-2H-[1,2,4]triazol-3-yl)phenyl]propanoate 0.2 ml (2.2 mmol) of dimethyl sulfate is added to a mixture of 0.6 g (2 mmol) of methyl 3-[4-(5-amino-2-methyl-2H-[1,2,4]triazol-3-yl)phenyl]-2(S)-ethoxypropanoate, 0.3 ml (2.2 mmol) of triethylamine and 40 ml of ethyl ether. The reaction medium is heated at 35° C. for 4 hours. The reaction changed very little, 20 ml of tetrahydrofuran, 0.3 ml of triethylamine and 0.2 ml (2.2 mmol) of dimethyl sulfate are added and the reaction medium is heated at 40° C. for a further 24 hours. The reaction medium is evaporated to dryness. The residue obtained is purified by thin-layer chromatography on silica eluted with a 97/3 and then 95/5 dichloromethane/methanol mixture. 0.1 g (16%) of methyl 2(S)-ethoxy-3-[4-(2-methyl-5-methylamino-2H-[1,2,4]triazol-3-yl)phenyl]propanoate and 0.4 g (60%) of 2(S)-ethoxy-3-[4-(2-methyl-5-methylamino-2H-[1,2,4]triazol-3-yl)phenyl]propionic acid are obtained.

(e) Preparation of Methyl 2(S)-ethoxy-3-{4-[5-(3-heptyl-1-methylureido)-2-methyl-2H-[1,2,4]triazol-3-yl]phenyl}propanoate In a manner similar to that of Example 7(i), starting with 80 mg (0.25 mmol) of methyl 2(S)-ethoxy-3-[4-(2-methyl-5-methylamino-2H-[1,2,4]triazol-3-yl)phenyl]propanoate and 60 μl (0.4 mmol) of heptyl isocyanate, 37 mg (34%) of methyl 2(S)-ethoxy-3-{4-[5-(3-heptyl-1-methylureido)-2-methyl-2H-[1,2,4]triazol-3-yl]phenyl}propanoate are obtained.

(f) Synthesis of 2(S)-Ethoxy-3-{4-[5-(3-heptyl-1-methylureido)-2-methyl-2H-[1,2,4]triazol-3-yl]phenyl}propanoic acid 37 mg (80 μmol) of methyl 2(S)-ethoxy-3-{4-[5-(3-heptyl-1-methylureido)-2-methyl-2H-[1,2,4]triazol-3-yl]phenyl}propanoate placed in 2 ml of tetrahydrofuran and 0.1 ml (0.1 mmol) of aqueous 1M lithium hydroxide solution are stirred at room temperature overnight. The reaction medium is acidified to pH 4 and extracted with ethyl acetate. The organic phase is washed with water, with saturated sodium chloride solution, dried over magnesium sulfate, filtered and evaporated. 30 mg (83%) of 2(S)-ethoxy-3-{4-[5-(3-heptyl-1-methylureido)-2-methyl-2H-[1,2,4]triazol-3-yl]phenyl}propanoic acid are obtained in the form of a white solid.

$^1$H NMR ($\delta$ CDCl$_3$): 0.88 (t, J=6.7 Hz, 3H); 1.24 (t, J=7.0 Hz, 3H); 1.26-1.39 (m, 8H); 1.60 (m, 2H); 3.13 (dd, J=7.5 Hz, J=4.1 Hz, 1H); 3.30 (dd, J=4.1 Hz, J=14 Hz, 1H); 3.38 (m, 2H); 3.47 (m, 3H); 3.54 (m, 1H); 3.68 (m, 1H); 3.93 (s, 3H); 4.18 (dd, J=7.3 Hz, J=4.2 Hz, 1H); 7.43 (d, J=8.1 Hz, 2H); 7.61 (d, J=8.1 Hz, 2H); 9.0 (s, 1H).

EXAMPLE 12

Synthesis of {3-[5-(2,4-dioxothiazolidin-5-ylmethyl)thiophen-2-yl]benzyl}methyloctanoylamide (a) Preparation of tert-butyl[3-(5-Formylthiophen-2-yl)benzyl]methylcarbamate In a manner similar to that of Example 7(f), starting with 3 g of 2-bromo-5-formylthiophene and 4 g of tert-butyl methyl [3-(4,4,5,5-tetramethyl[1,3,2]dioxaborolan-2-yl)benzyl]carbamate, 3 g of tert-butyl[3-(5-formylthiophen-2-yl)benzyl]methylcarbamate are obtained.

(b) Preparation of tert-butyl {3-[5-(2,4-Dioxothiazolidin-5-ylidenemethyl)thiophen-2-yl]benzyl}methylcarbamate A solution of 2.4 g (7.2 mmol) of tert-butyl[3-(5-formylthiophen-2-yl)benzyl]methylcarbamate, 0.85 g (7.2 mmol) of 2,4-thiazolidinedione and 0.2 g (1.4 mmol) of piperidinium acetate in 50 ml of toluene is refluxed for 4 hours in Dean-Stark apparatus. After cooling, the product precipitates. The precipitate is filtered off and washed with ethyl ether. 2.3 g (76%) of tert-butyl {3-[5-(2,4-dioxothiazolidin-5-ylidenemethyl)thiophen-2-yl]benzyl}methylcarbamate are obtained.

(c) Preparation of tert-butyl {3-[5-(2,4-Dioxothiazolidin-5-ylmethyl)thiophen-2-yl]benzyl}methylcarbamate 1 g (2.5 mmol) of tert-butyl {3-[5-(2,4-dioxothiazolidin-5-ylidenemethyl)thiophen-2-yl]benzyl}methylcarbamate is placed in 20 ml of dioxane and 0.2 ml of acetic acid. The reaction medium is degassed and placed under 3 atm of hydrogen for 3 days. After filtration through Celite, 0.2 g (20%) of tert-butyl {3-[5-(2,4-dioxothiazolidin-5-ylmethyl)thiophen-2-yl]benzyl}methylcarbamate is obtained.

(d) Preparation of 5-[5-(3-Methylaminomethylphenyl)thiophen-2-ylmethyl]thiazolidine-2,4-dione 0.2 g (0.5 mmol) of tert-butyl 3-[5-(2,4-dioxothiazolidin-5-ylmethyl)thiophen-2-yl]benzyl}methylcarbamate is placed in 10 ml of dichloromethane and 0.2 ml of trifluoroacetic acid for 12 hours. The reaction medium is evaporated to dryness and 200 mg (100%) of 5-[5-(3-methylaminomethylphenyl)thiophen-2-ylmethyl]thiazolidine-2,4-dione are obtained.

(e) Synthesis of -{3-[5-(2,4-dioxothiazolidin-5-ylmethyl)thiophen-2-yl]benzyl}methyloctanoylamide In a manner similar to that of Example 1(b), starting with 90 mg (0.3 mmol) of 5-[5-(3-methylaminomethylphenyl)thiophen-2-ylmethyl]thiazolidine-2,4-dione and 32 μl (0.3 mmol) of octanoyl chloride, 67 mg (92%) of {3-[5-(2,4-dioxothiazolidin-5-ylmethyl)thiophen-2-yl]benzyl}methyloctanoylamide are obtained.

$^1$H NMR ($\delta$ CDCl$_3$): 0.92 (t, J=6.7 Hz, 3H); 1.30-1.37 (m, 8H); 1.54 (m, 2H); 2.9 (s, 3H); 3.23 (m, 1H); 3.50 (m, 1H); 3.74 (m, 1H); 4.75 (m, 1H); 4.79 (m, 2H); 6.93-7.50 (m, 6H).

EXAMPLE 13

Synthesis of {3-[5-(2,4-dioxothiazolidin-5-ylmethyl)thiophen-2-yl]benzyl}methylhexanoylamide In a manner similar to that of Example 12(e), starting with 90 mg (0.3 mmol) of 5-[5-(3-methylaminomethylphenyl)thiophen-2-ylmethyl]thiazolidine-2,4-dione and 26 μl (0.3 mmol) of hexanoyl chloride, 22 mg (20%) of {3-[5-(2,4-dioxothiazolidin-5-ylmethyl)thiophen-2-yl]benzyl}methylhexanoylamide are obtained.

$^1$H NMR ($\delta$ CDCl$_3$): 0.92 (t, J=6.7 Hz, 3H); 1.30-1.37 (m, 4H); 1.54 (m, 2H); 2.9 (s, 3H); 3.23 (m, 2H); 3.50 (m, 1H); 3.74 (m, 1H); 4.75 (m, 1H); 4.79 (m, 2H); 6.93-7.50 (m, 6H).

EXAMPLE 14

Synthesis of 2(S)-(2-Benzoylphenylamino)-3-(4-{5-[(octanoylmethylamino)methyl]thiophen-3-yl}phenyl)propanoic acid (a) Preparation of Methyl 2(S)-(2-benzoylphenylamino)-3-(4-hydroxyphenyl)propanoate A solution of 56 g (0.29 mmol) of L-tyrosine methyl ester, 64 g (0.32 mmol) of benzoylcyclohexanone and 12 g of 10% palladium-on-charcoal in 700 ml of anisole is heated at 158° C. for 17 hours. The reaction medium is cooled to 50° C., filtered through Celite and evaporated under vacuum. The crude product obtained is taken up in a dichloromethane/pentane mixture and precipitated. After filtration, 18 g (20%) of methyl 2(S)-(2-benzoylphenylamino)-3-(4-hydroxyphenyl)propanoate are obtained.

(b) Preparation of Methyl 2(S)-(2-benzoylphenylamino)-3-(4-trifluoromethanesulfonyloxyphenyl)propanoate 1.2 g (10 mmol) of 4-dimethylaminopyridine are added to a mixture of 24.5 g (65 mmol) of methyl 2(S)-(2-benzoylphenylamino)-3-(4-hydroxyphenyl)propionate and 11 ml (78 mmol) of triethylamine in 220 ml of dichloromethane. The reaction medium is cooled to −78° C. and 13.2 ml (78 mmol) of triflic anhydride are added dropwise. The reaction medium is stirred from −78° C. to room temperature over 4 hours. After addition of saturated ammonium chloride solution, the reaction medium is extracted with dichloromethane. The organic phase is dried over magnesium sulfate, filtered and evaporated. 33 g (100%) of methyl 2(S)-(2-benzoylphenylamino)-3-(4-trifluoromethanesulfonyloxyphenyl)propanoate are obtained.

(c) Preparation of Methyl 2(S)-(2-benzoylphenylamino)-3-[4-(4,4,5,5-tetramethyl[1,3,2]dioxaborolan-2-yl)phenyl]propanoate In a manner similar to that of Example 7(e), starting with 28 g (55 mmol) of methyl 2(S)-(2-benzoylphenylamino)-3-(4-trifluoromethanesulfonyloxyphenyl)propanoate, 24.2 g (90%) of methyl 2(S)-(2-benzoylphenylamino)-3-[4-(4,4,5,5-tetramethyl[1,3,2]dioxaborolan-2-yl)phenyl]propanoate are obtained.

(d) Preparation of Methyl 2(S)-(2-benzoylphenylamino)-3-(4-{5-[(tert-butoxycarbonylmethylamino)methyl]thiophen-3-yl}phenyl)propanoate In a manner similar to that of Example 7(f), starting with 6 g (17 mmol) of methyl 2-(2-benzoylphenylamino)-3-[4-(4,4,5,5-tetramethyl[1,3,2]dioxaborolan-2-yl)phenyl]propanoate and 3.6 g (12 mmol) of tert-butyl (4-bromothiophen-2-ylmethyl)methylcarbamate (prepared as described in 16b), 2.9 g (42%) of methyl 2(S)-(2-benzoylphenylamino)-3-(4-{5-[(tert-butoxycarbonylmethylamino)methyl]thiophen-3-yl}phenyl)propanoate are obtained.

(e) Preparation of Methyl 2(S)-(2-benzoylphenylamino)-3-[4-(5-methylaminomethylthiophen-3-yl)phenyl]propanoate 2.9 g (5 mmol) of methyl 2(S)-(2-benzoylphenylamino)-3-(4-{5-[(tert-butoxycarbonylmethylamino)methyl]thiophen-3-yl}phenyl)propanoate are placed in 30 ml of dichloromethane and 2.5 ml (32 mmol) of trifluoroacetic acid. After stirring at room temperature for 18 hours, the reaction medium is evaporated to dryness. 2.4 g (100%) of methyl 2(S)-(2-benzoylphenylamino)-3-[4-(5-methylaminomethylthiophen-3-yl)phenyl]propanoate are obtained.

(f) Preparation of Methyl 2(S)-(2-benzoylphenylamino)-3-(4-{5-[(methyloctanoylamino)methyl]thiophen-3-yl}phenyl)propanoate In a manner similar to that of Example 1(b), starting with 0.8 g (1.65 mmol) of methyl 2(S)-(2-benzoylphenylamino)-3-[4-(5-methylaminomethylthiophen-3-yl)phenyl]propanoate and 0.3 ml (1.8 mmol) of octanoyl chloride, 0.8 g (78%) of methyl 2(S)-(2-benzoylphenylamino)-3-(4-{5-[(methyloctanoylamino)methyl]thiophen-3-yl}phenyl)propanoate are obtained.

(g) Synthesis of 2(S)-(2-Benzoylphenylamino)-3-(4-{5-[(methyloctanoylamino)methyl]thiophen-3-yl}phenyl)propanoic acid In a manner similar to that of Example 7(j), starting with 0.8 g (1 mmol) of methyl 2(S)-(2-benzoylphenylamino)-3-(4-{5-[(methyloctanoylamino)methyl]thiophen-3-yl}phenyl)propanoate, 0.5 g (63%) of 2(S)-(2-benzoylphenylamino)-3-(4-{5-[(methyloctanoylamino)methyl]thiophen-3-yl}phenyl)propanoic acid is obtained.

$^1$H NMR ($\delta$ CDCl$_3$): 0.89 (t, J=6.7 Hz, 3H); 1.29-1.32 (m, 16H); 1.68 (m, 2H); 2.35-2.48 (m, 2H); 2.99 (s, 3H); 3.23 (m, 1H); 3.37 (m, 1H); 4.48 (m, 1H); 4.66 (s, 2H); 6.60 (t, J=7.3 Hz, 1H); 6.72 (dd, J=2.5 Hz, J=8.4 Hz, 1H); 7.15-7.61 (12H); 9.0 (s, 1H); 10.5 (m, 1H).

EXAMPLE 15

Synthesis of 2(S)-(2-Benzoylphenylamino)-3-(4-{5-[(hexanoylmethylamino)methyl]thiophen-3-yl}phenyl)propanoic acid

(a) Preparation of Methyl 2(S)-(2-benzoylphenylamino)-3-(4-{5-[(hexanoylmethylamino)methyl]thiophen-3-yl}phenyl)propanoate In a manner similar to that of Example 1(b), starting with 0.8 g (1.65 mmol) of methyl 2(S)-(2-benzoylphenylamino)-3-[4-(5-methylaminomethylthiophen-3-yl)phenyl]propanoate and 0.25 ml (1.8 mmol) of hexanoyl chloride, 0.8 g (78%) of methyl 2(S)-(2-benzoylphenylamino)-3-(4-{5-[(methylhexanoylamino)methyl]thiophen-3-yl}phenyl)propanoate is obtained.

(b) Synthesis of 2(S)-(2-Benzoylphenylamino)-3-(4-{5-[(hexanoylmethylamino)methyl]thiophen-3-yl}phenyl)propanoic acid In a manner similar to that of Example 7(j), starting with 0.6 g (1 mmol) of methyl 2(S)-(2-benzoylphenylamino)-3-(4-{5-[(methylhexanoylamino)methyl]thiophen-3-yl}phenyl)propanoate, 0.57 g (100%) of 2(S)-(2-benzoylphenylamino)-3-(4-{5-[(methylhexanoylamino)methyl]thiophen-3-yl}phenyl)propanoic acid is obtained.

$^1$H NMR ($\delta$ CDCl$_3$): 0.92 (t, J=6.7 Hz, 3H); 1.30-1.36 (m, 4H); 1.70 (m, 2H°; 2.33-2.47 (m, 2H); 3.00 (s, 3H); 3.23 (dd, J=5.4 Hz, J=13.9 Hz, 1H); 3.38 (dd, J=5.4 Hz, J=8.5 Hz, 1H); 4.45 (m, 1H); 4.66-4.70 (m, 2H); 6.67 (t, J=7.5 Hz, 1H); 6.71 (d, J=8.4 Hz, 1H); 7.19-7.62 (m, 13H); 9.0 (s, 1H).

EXAMPLE 16

Synthesis of 2(S)-Ethoxy-3-(4-{5-[(hexanoylmethylamino)methyl]thiophen-3-yl}phenyl)propanoic acid

(a) Preparation of (4-Bromothiophen-2-ylmethyl)methylamine 25.2 g (360 mmol) of sodium cyanoborohydride are added to a solution of 35 g (180 mmol) of 4-bromothiophene-2-carbaldehyde, 62 g (640 mmol) of methylamine hydrochloride and 119 ml (846 mmol) of triethylamine. The reaction medium is stirred at room temperature for 3.5 hours. After addition of water and ethyl acetate and washing with aqueous 1M sodium hydroxide solution, the organic phase is extracted. The ethyl acetate phase is dried over magnesium sulfate, filtered and evaporated. The residue obtained is purified by thin-layer chromatography on silica eluted with a 90/10 to 70/30 heptane/ethyl acetate mixture. 19.7 g (52%) of (4-bromothiophen-2-ylmethyl)methylamine are obtained.

(b) Preparation of tert-butyl (4-Bromothiophen-2-ylmethyl)methylcarbamate 20.8 g (95 mmol) of di-tert-butyl dicarbonate are added portionwise to a solution of 19.7 g (95 mmol) of (4-bromothiophen-2-ylmethyl)methylamine and 11.9 ml (85 mmol) of triethylamine in 200 ml of dichloromethane. After stirring at room temperature for 16 hours, the reaction medium is washed with water and the dichloromethane phase is extracted. The organic phase is dried over magnesium sulfate, filtered and evaporated. 19 g (44%) of tert-butyl (4-bromothiophen-2-ylmethyl)methylcarbamate are obtained.

(c) Preparation of Methyl 3-(4-{5-[(tert-butoxycarbonylmethylamino)methyl]thiophen-3-yl}phenyl)-2(S)-ethoxypropanoate In a manner similar to that of Example 9(e), starting with 4 g (13 mmol) of tert-butyl (4-bromothiophen-2-ylmethyl)methylcarbamate and 5.6 g (20 mmol) of methyl 2(S)-ethoxy-3-[4-(4,4,5,5-tetramethyl-[1,3,2]dioxaborolan-2-yl)phenyl] propanoate, 5 g (88%) of methyl 3-(4-{5-[(tert-butoxycarbonylmethylamino)methyl]thiophen-3-yl}phenyl)-2(S)-ethoxypropanoate are obtained in the form of a yellow oil.

(d) Preparation of Methyl 2(S)-ethoxy-3-[4-(5-methylaminomethylthiophen-3-yl)phenyl]propanoate 5 g (11.5 mmol) of methyl 3-(4-{5-[(tert-butoxycarbonylmethylamino)methyl]thiophen-3-yl}phenyl)-2(S)-ethoxypropanoate are placed in 80 ml of dichloromethane and 4.4 ml of trifluoroacetic acid. After stirring at room temperature for 24 hours, water is added and the reaction medium is extracted with dichloromethane. The dichloromethane phase is washed with aqueous 30% sodium hydroxide solution, dried over magnesium sulfate, filtered and evaporated. The residue obtained is purified by thin-layer chromatography on silica eluted with a 50/50 heptane/ethyl acetate mixture. 3.2 g (84%) of methyl 2(S)-ethoxy-3-[4-(5-methylaminomethylthiophen-3-yl)phenyl]propanoate are obtained.

(e) Preparation of Methyl 2(S)-ethoxy-3-(4-{5-[(hexanoylmethylamino)methyl]thiophen-3-yl}phenyl) propanoate 0.18 ml (1.3 mmol) of hexanoyl chloride is added to a solution, cooled beforehand to 0° C., of 0.4 g (1.2 mmol) of methyl 2(S)-ethoxy-3-[4-(5-methylaminomethylthiophen-3-yl)phenyl]propanoate and 0.18 ml (1.3 mmol) of triethylamine in 20 ml of tetrahydrofuran. The reaction medium is stirred at room temperature for 2 hours, washed with water and extracted with ethyl acetate. The ethyl acetate phase is dried over magnesium sulfate, filtered and evaporated. The residue obtained is purified by thin-layer chromatography on silica eluted with a 70/30 heptane/ethyl acetate mixture. 0.4 g (83%) of methyl 2(S)-ethoxy-3-(4-{5-[(hexanoylmethylamino)methyl]thiophen-3-yl}phenyl)propanoate is obtained.

(f) Synthesis of 2(S)-Ethoxy-3-(4-{5-[(hexanoylmethylamino)methyl]thiophen-3-yl}phenyl)propanoic acid In a manner similar to that of Example 11(f), starting with 0.4 g (1 mmol) of 2(S)-ethoxy-3-(4-{5-[(hexanoylmethylamino)methyl]thiophen-3-yl}phenyl)propanoate, 0.4 g of crude residue is obtained. This residue is hot-recrystallized from isopropyl ether. 0.2 g (50%) of 2(S)-ethoxy-3-(4-{5-[(hexanoylmethylamino)methyl]thiophen-3-yl}pro-panoic acid is obtained in the form of a white solid with a melting point of 65° C.
$^1$H NMR ($\delta$ CDCl$_3$): 0.90 (t, J=6.7 Hz, 3H); 1.19 (t, J=7.0 Hz, 3H); 1.35-1.37 (m, 4H); 1.70 (m, 2H); 2.36-2.48 (m, 2H); 3.02 (m, 1H); 3.03 (s, 3H); 3.15 (m, 1H); 3.45 (m, 1H); 3.65 (m, 1H); 4.10 (m, 1H); 4.69-4.74 (m, 2H); 7.19-7.35 (m, 4H); 7.50 (d, J=8.2 Hz, 2H).

EXAMPLE 17

Synthesis of 3-(4-{5-[(Butyrylmethylamino)methyl] thiophen-3-yl}phenyl)-2(S)-ethoxypropanoic acid

(a) Preparation of Methyl 3-(4-{5-[(butyrylmethylamino)methyl]thiophen-3-yl}phenyl-2(S)-ethoxypropanoate In a manner similar to that of Example 16(e), starting with 0.1 g (0.3 mmol) of methyl 2(S)-ethoxy-3-[4-(5-methylaminomethylthiophen-3-yl)phenyl]propanoate and 40 μl (0.33 mmol) of butanoyl chloride, 0.12 g (75%) of methyl 3-(4-{5-[(butyrylmethylamino)methyl]thiophen-3-yl}phenyl)-2(S)-ethoxypropanoate is obtained.

(b) Synthesis of -3-(4-{5-[(Butyrylmethylamino) methyl]thiophen-3-yl}phenyl)-2(S)-ethoxypropanoic acid In a manner similar to that of Example 11(f), starting with 90 mg (0.22 mmol) of methyl 3-(4-{5-[(butyrylmethylamino) methyl]thiophen-3-yl}phenyl-2(S)-ethoxypropanoate, 45 mg (52%) of 3-(4-{5-[(butyrylmethylamino)methyl] thiophen-3-yl}phenyl)-2(S)-ethoxypropanoic acid are obtained in the form of a solid with a melting point of 56-57° C.
$^1$H NMR ($\delta$ CDCl$_3$): 1.00 (t, J=6.7 Hz, 3H); 1.19 (t, J=7.0 Hz, 3H); 1.74 (m, 2H); 2.36-2.48 (m, 2H); 3.02 (m, 1H); 3.03 (s, 3H); 3.15 (m, 1H); 3.48 (m, 1H); 3.65 (m, 1H); 4.11 (m, 1H); 4.69-4.74 (m, 2H); 7.19-7.35 (m, 4H); 7.50 (d, J=8.2 Hz, 2H).

EXAMPLE 18

Synthesis of 3-[4-(5-{[(3-Cyclohexylpropionyl)methylamino]methyl}thiophen-3-yl)phenyl]-2(S)-ethoxypropanoic acid

(a) Preparation of Methyl 3-[4-(5-{[(2-cyclopentylacetyl)methylamino]methyl}thiophen-3-yl)phenyl]-2(S)-ethoxypropanoate In a manner similar to that of Example 16(e), starting with 0.35 g (1 mmol) of methyl 2(S)-ethoxy-3-[4-(5-methylaminomethylthiophen-3-yl)phenyl]propanoate and 170 μl (1.15 mmol) of 2-cyclopentylacetyl chloride, 0.39 g (85%) of methyl 3-[4-(5-{[(2-cyclopentylacetyl)methylamino] methyl}thiophen-3-yl)phenyl]-2(S)-ethoxypropanoate is obtained.

(b) Synthesis of 3-[4-(5-{[(2-Cyclopentylacetyl)methylamino]methyl}thiophen-3-yl)phenyl]-2(S)-ethoxypropanoic acid In a manner similar to that of Example 11(f), starting with 0.39 g (0.88 mmol) of methyl 3-[4-(5-{[(2-cyclopentylacetyl)methylamino]methyl}thiophen-3-yl)phenyl]-2(S)-ethoxypropanoate, 0.24 g (63%) of 3-[4-(5-{[(2-cyclopentylacetyl)methylamino]methyl}thiophen-3-yl)phenyl]-2(S)-ethoxypropanoic acid is obtained in the form of a solid with a melting point of 112-113° C.

¹H NMR (δ CDCl₃): 1.19 (t, J=7.0 Hz, 3H); 1.60-1.65 (m, 4H); 1.90 (m, 2H); 2.30 (m, 1H); 2.37-2.52 (m, 2H); 3.02 (m, 1H); 3.04 (s, 3H); 3.17 (m, 1H); 3.48 (m, 1H); 3.65 (m, 1H); 4.12 (m, 1H); 4.70-4.75 (m, 2H); 7.19-7.36 (m, 4H); 7.50 (d, J=8.2 Hz, 2H).

EXAMPLE 19

Synthesis of 3-[4-(5-{[(3-Cyclohexylpropionyl)methylamino]methyl}thiophen-3-yl)phenyl]-2(S)-ethoxypropanoic acid (a) Preparation of Methyl 3-[4-(5-{[(3-cyclohexylpropionyl)methylamino]methyl}thiophen-3-yl)phenyl]-2(S)-ethoxypropanoate In a manner similar to that of Example 16(e), starting with 0.35 g (1 mmol) of methyl 2(S)-ethoxy-3-[4-(5-methylaminomethylthiophen-3-yl)phenyl]propanoate and 170 μl (1.15 mmol) of 2-cyclopentylacetyl chloride, 0.41 g (84%) of methyl 3-[4-(5-{[(3-cyclohexylpropionyl)methylamino]methyl}thiophen-3-yl)phenyl]-2(S)-ethoxypropanoate is obtained.

(b) Synthesis of 3-[4-(5-{[(3-Cyclohexylpropionyl)methylamino]methyl}thiophen-3-yl)phenyl]-2(S)-ethoxypropanoic acid In a manner similar to that of Example 11(f), starting with 0.41 g (0.87 mmol) of methyl 3-[4-(5-{[(3-cyclohexylpropionyl)methylamino]methyl}thiophen-3-yl)phenyl]-2(S)-ethoxypropanoate, 0.23 g (57%) of 3-[4-(5-{[(3-cyclohexylpropionyl)methylamino]methyl}thiophen-3-yl)phenyl]-2(S)-ethoxypropanoic acid is obtained in the form of a solid with a melting point of 69-70° C.

¹H NMR (δ CDCl₃): 0.95 (m, 2H), 1.19 (t, J=7.0 Hz, 3H); 1.20-1.28 (m, 4H); 1.57 (m, 1H); 1.58-1.72 (m, 6H); 2.37-2.49 (m, 2H); 3.02 (m, 1H); 3.04 (s, 3H); 3.15 (m, 1H); 3.47 (m, 1H); 3.63 (m, 1H); 4.12 (m, 1H); 4.69-4.74 (m, 2H); 7.19-7.36 (m, 4H); 7.50 (d, J=8.2 Hz, 2H).

EXAMPLE 20

Synthesis of 2-Ethoxy-3-{6-[3-(3-heptyl-1-methylureido)phenyl]pyrid-3-yl}propanoic acid (a) Preparation of (6-Iodopyrid-3-yl)methanol 30 g (108 mmol) of ethyl 6-iodonicotinate dissolved in 300 ml of ethanol are added dropwise to a solution of 20.5 g (542 mmol) of sodium borohydride in 200 ml of ethanol, cooled beforehand to 0° C. The reaction medium is allowed to warm to room temperature and is then stirred for 1 hour 30 minutes at room temperature. The reaction medium is hydrolysed and extracted with ethyl acetate. The boron salts precipitate out, and the medium is filtered and then evaporated to dryness. The reaction medium is taken up in dichloromethane, the product precipitates out, isopropyl ether is added and the medium is filtered. The precipitate is washed with isopropyl ether. 17 g (67%) of (6-iodopyrid-3-yl)methanol are obtained in the form of a pale yellow solid with a melting point of 102° C.

(b) Preparation of 6-Iodopyridine-3-carbaldehyde 63 g (723 mmol) of manganese dioxide are added to a solution of 17 g (72 mmol) of (6-iodopyrid-3-yl)methanol in 600 ml of dichloromethane. The reaction medium is stirred at room temperature for 20 hours and then filtered through Celite. The precipitate is washed thoroughly with water and the filtrate is evaporated under vacuum. The residue obtained is taken up in dichloromethane and the insoluble material is again filtered off. After evaporation of the filtrate, 13.2 g (78%) of 6-iodopyridine-3-carbaldehyde are obtained in the form of a pale yellow solid with a melting point of 141° C.

(c) Preparation of tert-butyl[3-(5-Formylpyrid-2-yl) phenyl]methylcarbamate c.1: tert-butyl (3-Bromophenyl)methylcarbamate 8.4 g (209.4 mmol) of 60% sodium hydride are added portionwise to a solution of 19 ml (174 mmol) of 3-bromoaniline in 300 ml of tetrahydrofuran. The reaction medium is stirred at room temperature until the evolution of gas has ceased, and 38 g (174 mmol) of di-tert-butyl dicarbonate dissolved in 40 ml of tetrahydrofuran are then added dropwise. The reaction medium is stirred at reflux for 8 hours and then at room temperature for 18 hours. Water is added and the reaction medium is extracted with ethyl acetate. The ethyl acetate phase is washed with saturated sodium chloride solution, dried over magnesium sulfate, filtered and evaporated. The residue obtained is purified by thin-layer chromatography on silica eluted with a 90/10, then 80/20 and 70/30 heptane/ethyl acetate mixture. 47 g (92%) of tert-butyl (3-bromophenyl)methylcarbamate are obtained.

c.2: tert-butyl (3-Bromophenyl)methylcarbamate 7.6 g (190 mmol) of 60% sodium hydride are added portionwise to a solution of 47 g (173 mmol) of tert-butyl (3-bromophenyl)methylcarbamate in 500 ml of dimethylformamide. After the evolution of gas has ceased, 54 ml (865 mmol) of methyl iodide are added and the reaction medium is stirred at room temperature for 5 hours. After addition of water, the medium is extracted with ethyl acetate. The ethyl acetate phase is washed thoroughly with water, dried over magnesium sulfate, filtered and evaporated. 49 g (100%) of tert-butyl (3-bromophenyl)methylcarbamate are obtained.

c.3: tert-butyl Methyl-[3-(4,4,5,5-tetramethyl[1,3,2] dioxaborolan-2-yl)phenyl]carbamate In a manner similar to that of Example 7(e), starting with 5 g (17.5 mmol) of tert-butyl (3-bromophenyl)methylcarbamate, 3.4 g (60%) of tert-butyl methyl[3-(4,4,5,5-tetramethyl [1,3,2]dioxaborolan-2-yl)phenyl]carbamate are obtained.

c.4: tert-butyl[3-(5-Formylpyrid-2-yl)phenyl]methylcarbamate

In a manner similar to that of Example 7(f), starting with 1.6 g (6.8 mmol) of 6-iodopyridine-3-carbaldehyde and 3.4 g (16.2 mmol) of tert-butyl methyl[3-(4,4,5,5-tetramethyl[1,3, 2]dioxaborolan-2-yl)phenyl]carbamate, 1.2 g (58%) of tert-butyl[3-(5-formylpyrid-2-yl)phenyl]methylcarbamate are obtained.

(d) Preparation of Ethyl 3-{6-[3-(tert-butoxycarbonylmethylamino)phenyl]pyrid-3-yl}-2-ethoxyacrylate d.1: Ethyl chloroethoxyacetate A solution of 40 ml (224 mmol) of ethyl diethoxyacetate, 19 ml (268 mmol) of acetyl chloride and 0.1 g (0.45 mmol) of iodine is heated at 50° C. for 4 hours. Only 60% of the desired product is formed. The reaction medium is cooled to room temperature, 19 ml (268 mmol) of acetyl chloride are added and the medium is heated at 50° C. for a further 18 hours. The reaction medium is evaporated to dryness under vacuum. 36.3 g (100%) of crude ethyl chloroethoxyacetate are obtained.

d.2: Ethyl (diethoxyphosphoryl)ethoxyacetate 36.3 g (218 mmol) of ethyl chloroethoxyacetate and 37.4 ml (218 mmol) of triethyl phosphite are heated at 50° C. for 3 hours. The reaction medium is evaporated to dryness under vacuum. 57 g (100%) of crude ethyl (diethoxyphosphoryl)ethoxyacetate are obtained.

d.3: Ethyl 3-{6-[3-(tert-butoxycarbonylmethylamino)phenyl]pyrid-3-yl}-2-ethoxyacrylate 0.3 g (8 mmol) of 60% sodium hydride is added portionwise to a solution of 2.1 g (8 mmol) of ethyl (diethoxyphosphoryl)ethoxyacetate in 8 ml of tetrahydrofuran. After stirring at room temperature for 30 minutes and after the evolution of gas has ceased, 1.2 g (4 mmol) of tert-butyl[3-(5-formylpyrid-2-yl)phenyl]methylcarbamate dissolved in 6 ml of tetrahydrofuran are added. The reaction medium is stirred at room temperature for 18 hours. The reaction medium is diluted with water and extracted with ethyl acetate. The organic phase is washed with water, dried over magnesium sulfate, filtered and evaporated. The residue obtained is purified by thin-layer chromatography on silica eluted with a 90/10, then 80/20 and 70/30 heptane/ethyl acetate mixture. 0.2 g (12%) of ethyl 3-{6-[3-(tert-butoxycarbonylmethylamino)phenyl]pyrid-3-yl}-2-ethoxyacrylate is obtained.

(f) Preparation of Ethyl 3-{6-[3-(tert-butoxycarbonylmethylamino)phenyl]pyrid-3-yl}-2-ethoxypropanoate A solution of 0.2 g (0.5 mmol) of ethyl 3-{6-[3-(tert-butoxycarbonylmethylamino)phenyl]pyrid-3-yl}-2-ethoxyacrylate in 10 ml of tetrahydrofuran is degassed and 0.02 g (10% by mass) of 10% Pd/C is added. After reaction for 5 hours under an atmospheric pressure of hydrogen, the reaction medium is stirred under 3 atm of hydrogen for 24 hours. After filtration through Celite and evaporation of the filtrate, 0.11 g (55%) of ethyl 3-{6-[3-(tert-butoxycarbonylmethylamino)phenyl]pyrid-3-yl}-2-ethoxypropanoate is obtained.

(g) Preparation of Ethyl 2-ethoxy-3-[6-(3-methylaminophenyl)pyrid-3-yl]propanoate 0.11 g (0.3 mmol) of ethyl 3-{6-[3-(tert-butoxycarbonylmethylamino)phenyl]pyrid-3-yl}-2-ethoxypropanoate, 5 ml of dichloromethane and 0.15 ml (1.9 mmol) of trifluoroacetic acid are stirred at room temperature for 24 hours. After addition of water, the reaction medium is extracted with dichloromethane. The organic phase is dried over magnesium sulfate, filtered and evaporated. 80 mg (94%) of ethyl 2-ethoxy-3-[6-(3-methylaminophenyl)pyrid-3-yl]propanoate are obtained.

(h) Preparation of Ethyl 2-ethoxy-3-{6-[3-(3-heptyl-1-methylureido)phenyl]pyrid-3-yl}propanoate 80 μl (0.5 mmol) of heptyl isocyanate are added to 80 mg (0.24 mmol) of ethyl 2-ethoxy-3-[6-(3-methylaminophenyl)pyrid-3-yl]propanoate in 5 ml of dichloromethane. After stirring at room temperature for 24 hours, water is added and the reaction medium is extracted with dichloromethane. The organic phase is dried over magnesium sulfate, filtered and evaporated. The residue obtained is purified by thin-layer chromatography on silica eluted with a 60/40 heptane/ethyl acetate mixture. 60 mg (54%) of ethyl 2-ethoxy-3-{6-[3-(3-heptyl-1-methylureido)phenyl]pyrid-3-yl}propanoate are obtained.

(i) Synthesis of 2-Ethoxy-3-{6-[3-(3-heptyl-1-methylureido)phenyl]pyrid-3-yl}propanoic acid 60 mg (0.13 mmol) of ethyl 2-ethoxy-3-{6-[3-(3-heptyl-1-methylureido)phenyl]pyrid-3-yl}propanoate are placed in 4 ml of tetrahydrofuran, 0.2 ml (0.2 mmol) of aqueous 1M lithium hydroxide solution is added and the mixture is stirred at room temperature for 24 hours. After acidic hydrolysis to pH 4.5-5, the reaction medium is extracted with ethyl acetate. The organic phase is dried over magnesium sulfate, filtered and evaporated. The residue obtained is purified by thin-layer chromatography on silica eluted with a 50/50 heptane/ethyl acetate mixture and then a 90/10 dichloromethane/methanol mixture. 40 mg (70%) of 2-ethoxy-3-{6-[3-(3-heptyl-1-methylureido)phenyl]pyrid-3-yl}propanoic acid are obtained in the form of a white solid with a melting point of 142-143° C.

$^1$H NMR (δ CDCl$_3$): 0.86 (t, J=6.7 Hz, 3H), 1.19 (t, J=7.0 Hz, 3H); 1.20-1.25 (m, 8H); 1.42 (m, 2H); 3.15 (m, 1H); 3.18 (m, 2H); 3.19 (m, 1H); 3.34 (s, 3H); 3.53 (m, 1H); 3.72 (m, 1H); 4.41 (m, 1H); 7.30 (m, 1H); 7.50-7.85 (m, 5H); 8.60 (m, 1H).

EXAMPLE 21

Synthesis of 2(S)-(2-Benzoylphenylamino)-3-{4-[6-(1-methyl-3-pentylureido)pyrid-2-yl]phenyl}propanoic acid

(a) Preparation of Methyl 2(S)-(2-benzoylphenylamino)-3-{4-[6-(tert-butoxycarbonylmethylamino)pyrid-2-yl]phenyl}propanoate In a manner similar to that of Example 14(d), starting with 12.7 g (26 mmol) of methyl 2-(2-benzoylphenylamino)-3-[4-(4,4,5,5-tetramethyl[1,3,2]dioxaborolan-2-yl)phenyl]propanoate and 5 g (17 mmol) of tert-butyl (3-bromophenyl)methylcarbamate (prepared as described in 9b), 8.3 g (84%) of methyl 2(S)-(2-benzoylphenylamino)-3-{4-[6-(tert-butoxycarbonylmethylamino)pyrid-2-yl]phenyl}propanoate are obtained.

(b) Preparation of Methyl 2(S)-(2-benzoylphenylamino)-3-[4-(6-methylaminopyrid-2-yl)phenyl]propanoate In a manner similar to that of Example 14(e), starting with 8.3 g (15 mmol) of methyl 2(S)-(2-benzoylphenylamino)-3-{4-[6-(tert-butoxycarbonylmethylamino)pyrid-2-yl]phenyl}propanoate, 7.1 g (100%) of methyl 2(S)-(2-benzoylphenylamino)-3-[4-(6-methylaminopyrid-2-yl)phenyl]propanoate are obtained.

(c) Preparation of Methyl 2(S)-(2-benzoylphenylamino)-3-{4-[6-(1-methyl-3-pentylureido)pyrid-2-yl]phenyl}propanoate In a manner similar to that of Example 7(i), starting with 0.9 g (1.9 mmol) of methyl 2(S)-(2-benzoylphenylamino)-3-

[4-(6-methylaminopyrid-2-yl)phenyl]propanoate and 0.35 ml (2.1 mmol) of pentyl isocyanate, 0.7 g (63%) of methyl 2(S)-(2-benzoylphenylamino)-3-{4-[6-(1-methyl-3-pentylureido)pyrid-2-yl]phenyl}propanoate is obtained.

(d) Synthesis of 2(S)-(2-Benzoylphenylamino)-3-{4-[6-(1-methyl-3-pentylureido)pyrid-2-yl]phenyl}propanoic acid In a manner similar to that of Example 7(j), starting with 0.22 g (0.4 mmol) of methyl 2(S)-(2-benzoylphenylamino)-3-{4-[6-(1-methyl-3-pentylureido)pyrid-2-yl]phenyl}propanoate, 0.2 g (95%) of 2(S)-(2-benzoylphenylamino)-3-{4-[6-(1-methyl-3-pentylureido)pyrid-2-yl]phenyl}propanoic acid is obtained.
$^1$H NMR ($\delta$ CDCl$_3$): 0.77 (t, J=6.7 Hz, 3H); 1.23-1.25 (m, 4H); 1.53 (m, 2H); 3.20-3.46 (m, 4H); 3.41 (s, 3H); 4.47 (m, 1H); 6.59 (t, J=7.4 Hz, 1H); 6.68 (d, J=8.5 Hz, 1H); 6.86 (d, J=8.5 Hz, 1H); 7.22-7.73 (m, 13H); 9.0 (s, 1H); 10.5 (s, 1H).

EXAMPLE 22

Synthesis of 2(S)-(2-Benzoylphenylamino)-3-{4-[6-(1-methyl-3-heptylureido)pyrid-2-yl]phenyl}propanoic acid (a) Preparation of Methyl 2(S)-(2-benzoylphenylamino)-3-{4-[6-(1-methyl-3-heptylureido)pyrid-2-yl]phenyl}propanoate In a manner similar to that of Example 7(i), starting with 0.35 g (0.7 mmol) of methyl 2(S)-(2-benzoylphenylamino)-3-[4-(6-methylaminopyrid-2-yl)phenyl]propanoate and 0.3 ml (2.1 mmol) of heptyl isocyanate, 0.4 g (94%) of methyl 2(S)-(2-benzoylphenylamino)-3-{4-[6-(1-methyl-3-heptylureido)pyrid-2-yl]phenyl}propanoate is obtained.

(b) Synthesis of 2(S)-(2-Benzoylphenylamino)-3-{4-[6-(1-methyl-3-heptylureido)pyrid-2-yl]phenyl}propanoic acid In a manner similar to that of Example 7(j), starting with 0.7 g (0.4 mmol) of methyl 2(S)-(2-benzoylphenylamino)-3-{4-[6-(1-methyl-3-heptylureido)pyrid-2-yl]phenyl}propanoate, 0.65 g (90%) of 2(S)-(2-benzoylphenylamino)-3-{4-[6-(1-methyl-3-heptylureido)pyrid-2-yl]phenyl}propanoic acid is obtained.
$^1$H NMR ($\delta$ CDCl$_3$): 0.83 (t, 3H, J=6.7 Hz); 1.15-1.28 (m, 4H); 1.51-1.58 (m, 2H); 3.27 (dd, 1H, J=13.8 Hz, J=7.9 Hz); 3.31 (m, 2H); 3.42 (s, 3H); 3.44 (dd, 1H, J=1.4 Hz, J=13.8 Hz); 4.50 (m, 1H); 6.62 (t, J=7.4 Hz, 1H); 6.73 (d, J=8.5 Hz, 1H); 6.89 (d, J=8.5 Hz, 1H); 7.29-7.77 (m, 13H); 9.0 (m, 1H); 10.5 (m, 1H).

EXAMPLE 23

Synthesis of 2(S)-Ethoxy-3-{6-[3-(3-heptyl-1-methylureido)phenyl]pyrid-3-yl}propanoic acid (a) Preparation of 2(S)-Ethoxy-3-[6-(3-methylaminophenyl)pyrid-3-yl]propanoic acid 0.9 g (2.7 mmol) of ethyl 2-ethoxy-3-[6-(3-methylaminophenyl)pyrid-3-yl]propanoate, prepared as described in Example 20 g, is placed in 60 ml of a pH 7 buffer solution, with 0.75 g of the enzyme Proteinase 2A. After 10 days at room temperature, the reaction has not progressed. The reaction medium is heated at 37° C. for 1 day: the reaction is complete.
Water is added, the pH is brought to 8 by addition of 1M sodium hydroxide solution and the reaction medium is extracted with ethyl acetate. The ethyl acetate phase is washed with saturated sodium chloride solution, dried over magnesium sulfate, filtered and evaporated. The aqueous phase is acidified with aqueous 1N acetic acid solution to pH 4 and extracted with ethyl acetate. The ethyl acetate phase is washed with saturated sodium chloride solution, dried over magnesium sulfate, filtered and evaporated. The residue obtained is purified by thin-layer chromatography on silica eluted with a 95/5, 90/10 and then 80/20 dichloromethane/methanol mixture. 0.1 g (24%) of 2(S)-ethoxy-3-[6-(3-methylaminophenyl)pyrid-3-yl]propanoic acid is obtained.

(b) Preparation of Methyl 2(S)-ethoxy-3-[6-(3-methylaminophenyl)pyrid-3-yl]propanoate 0.1 g (0.3 mmol) of 2(S)-ethoxy-3-[6-(3-methylaminophenyl)pyrid-3-yl]propanoic acid is placed in 5 ml of methanol and 2 drops of concentrated sulfuric acid are added. The reaction medium is heated at 65° C. for 18 hours. The methanol is evaporated off and the residue is taken up in an ethyl acetate/water mixture. The pH is brought to 7 by addition of 1N sodium hydroxide solution and the reaction medium is extracted with ethyl acetate. The ethyl acetate phase is dried over sodium sulfate, filtered and evaporated. 70 mg (70%) of methyl 2(S)-ethoxy-3-[6-(3-methylaminophenyl)pyrid-3-yl]propanoate are obtained.

(c) Preparation of Methyl 2(S)-ethoxy-3-(6-{3-[methyl(4-nitrophenoxycarbonyl)amino]phenyl}pyrid-3-yl)propanoate 70 mg (0.3 mmol) of 4-nitrophenyl chloroformate and then 60 µl (0.3 mmol) of diisopropylethylamine are added to a solution of 70 mg (0.25 mmol) of methyl 2(S)-ethoxy-3-[6-(3-methylaminophenyl)pyrid-3-yl]propanoate in 3 ml of dichloromethane. The reaction medium is stirred at room temperature for 2 hours. After addition of water, the reaction medium is extracted with dichloromethane. The organic phase is dried over magnesium sulfate, filtered and evaporated. 110 mg (100%) of methyl 2(S)-ethoxy-3-(6-{3-[methyl(4-nitrophenoxycarbonyl)amino]phenyl}pyrid-3-yl)propanoate are obtained.

(d) Preparation of Methyl 2(S)-ethoxy-3-{6-[3-(3-heptyl-1-methylureido)phenyl]pyrid-3-yl}propanoate 70 µl (0.45 mmol) of heptylamine are added to a solution of 110 mg (0.25 mmol) of methyl 2(S)-ethoxy-3-(6-{3-[methyl (4-nitrophenoxycarbonyl)amino]phenyl}pyrid-3-yl)propanoate in 3 ml of dimethylformamide. The reaction medium is heated at 80° C. for 3 hours. After addition of water, the reaction medium is extracted with ethyl acetate. The organic phase is dried over magnesium sulfate, filtered and evaporated. The residue obtained is purified by thin-layer chromatography on silica eluted with a 6/4 and then 5/5 heptane/ethyl acetate mixture. 50 mg (50%) of methyl 2(S)-ethoxy-3-{6-[3-(3-heptyl-1-methylureido)phenyl]pyrid-3-yl}propanoate are obtained.

(e) Synthesis of 2(S)-Ethoxy-3-{6-[3-(3-heptyl-1-methylureido)phenyl]pyrid-3-yl}propanoic acid In a manner similar to that of Example 20(i), starting with 50 mg (0.1 mmol) of methyl 2(S)-ethoxy-3-{6-[3-(3-heptyl- 1-methylureido)phenyl]pyrid-3-yl}propanoate, 25 mg (50%) of 2(S)-ethoxy-3-{6-[3-(3-heptyl-1-methylureido)phenyl] pyrid-3-yl}propanoic acid are obtained in the form of a white solid with a melting point of 140-141° C.

$^1$H NMR (d, CDCl$_3$): 0.87 (t, J=6.7 Hz, 3H); 1.24-1.33 (m, 11H); 1.40-1.45 (m, 2H); 3.16-3.21 (m, 4H); 3.34 (s, 3H); 3.56-3.60 (m, 1H); 3.69-3.73 (m, 1H); 4.17-4.20 (m, 1H); 4.40 (t, J=5.2 Hz, 1H); 7.30-7.33 (m, 1H); 7.51-7.55 (m, 1H); 7.67-7.75 (m, 2H); 7.88-7.90 (m, 2H); 8.60 (d, J=1.2 Hz, 1H).

EXAMPLE 24

Synthesis of 2(S)-Ethoxy-3-{4-[6-(1-methyl-3-pentylureido)pyrid-2-yl]phenyl}propanoic acid hydrochloride (a) Preparation of Methyl 2(S)-ethoxy-3-{4-[6-(1-methyl-3-pentylureido)pyrid-2-yl]phenyl}propanoate a.1-Methyl 2(S)-ethoxy-3-(4-{6-[methyl(4-nitrophenoxycarbonyl)amino]pyrid-2-yl}phenyl)propanoate 0.96 g (4.8 mmol) of 4-nitrophenyl chloroformate and then 0.85 ml (4.8 mmol) of diisopropylethylamine are added to a solution of 1 g (3.2 mmol) of methyl 2(S)-ethoxy-3-[4-(6-methylaminopyrid-2-yl)phenyl]propanoate in 25 ml of dichloromethane. The reaction medium is stirred at room temperature for 1 hour 30 minutes. After addition of water and extraction with dichloromethane, the organic phase is dried over magnesium sulfate, filtered and evaporated. 1.9 g (100%) of methyl 2(S)-ethoxy-3-(4-{6-[methyl-(4-nitrophenoxycarbonyl)amino]pyrid-2-yl}phenyl)propanoate are obtained.

a.2-Methyl 2(S)-ethoxy-3-{4-[6-(1-methyl-3-pentylureido)pyrid-2-yl]phenyl}propanoate 0.65 g (1.1 mmol) of methyl 2(S)-ethoxy-3-(4-{6-[methyl-(4-nitrophenoxycarbonyl)amino]pyrid-2-yl}phenyl)propanoate, 12 ml of dimethylformamide and 1 ml (8.8 mmol) of pentylamine are heated at 80° C. for 18 hours. After addition of water, the reaction medium is extracted with ethyl acetate. The ethyl acetate phase is dried over magnesium sulfate, filtered and evaporated. The residue obtained is purified by thin-layer chromatography on silica eluted with a 7/3 and then 6/4 heptane/ethyl acetate mixture. 0.35 g (76%) of methyl 2(S)-ethoxy-3-{4-[6-(1-methyl-3-pentylureido)pyrid-2-yl]phenyl}propanoate is obtained.

(b) Preparation of 2(S)-Ethoxy-3-{4-[6-(1-methyl-3-pentylureido)pyrid-2-yl]phenyl}propanoic acid In a manner similar to that of Example 20(i), starting with 0.35 g (0.8 mmol) of methyl 2(S)-ethoxy-3-{4-[6-(1-methyl-3-pentylureido)pyrid-2-yl]phenyl}propanoate, 300 mg (100%) of 2(S)-ethoxy-3-{4-[6-(1-methyl-3-pentylureido) pyrid-2-yl]phenyl}propanoic acid are obtained.

(c) Synthesis of 2(S)-ethoxy-3-{4-[6-(1-methyl-3-pentylureido)pyrid-2-yl]phenyl}propanoic acid hydrochloride In a manner similar to that of Example 10, starting with 300 mg of 2(S)-ethoxy-3-{4-[6-(1-methyl-3-pentylureido)pyrid-2-yl]phenyl}propanoic acid, 200 mg of 2(S)-ethoxy-3-{4-[6-(1-methyl-3-pentylureido)pyrid-2-yl]phenyl}propanoic acid hydrochloride are obtained in the form of a white solid $^1$H NMR (d CDCl$_3$): 0.84 (t, J=6.9 Hz, 3H); 1.12 (t, J=7.0 Hz, 3H); 1.29-1.34 (m, 4H); 1.63-1.66 (m, 2H); 3.04 (dd, J=8.4 Hz, J=14.0 Hz, 1H); 3.14 (dd, J=4.0 Hz, J=14.0 Hz, 1H); 3.31-3.37 (m, 3H); 3.64-3.70 (m, 4H); 4.01 (dd, J=4.0 Hz, J=8.4 Hz, 1H); 7.23 (d, J=8.2 Hz, 1H); 7.45-7.47 (m, 3H); 7.70-7.71 (d, J=8.2 Hz, 2H); 8.06 (t, J=7.70 Hz, 1H).

EXAMPLE 25

Synthesis of 2(S)-Ethoxy-3-{4-[6-(1-methyl-3-butylureido)pyrid-2-yl]phenyl}propanoic acid (a) Preparation of Methyl 2(S)-ethoxy-3-{4-[6-(1-methyl-3-butylureido)pyrid-2-yl]phenyl}propanoate In a manner similar to that of Example 24(a), starting with 0.2 g (0.64 mmol) of methyl 2(S)-ethoxy-3-[4-(6-methylaminopyrid-2-yl)phenyl]propanoate, 0.2 g (80%) of methyl 2(S)-ethoxy-3-{4-[6-(1-methyl-3-butylureido)pyrid-2-yl] phenyl}propanoate is obtained.

(b) Synthesis of 2(S)-Ethoxy-3-{4-[6-(1-methyl-3-butylureido)pyrid-2-yl]phenyl}propanoic acid In a manner similar to that of Example 20(i), starting with 0.2 g (0.5 mmol) of methyl 2(S)-ethoxy-3-{4-[6-(1-methyl-3-butylureido)pyrid-2-yl]phenyl}propanoate, 130 mg (90%) of 2(S)-ethoxy-3-{4-[6-(1-methyl-3-butylureido)pyrid-2-yl] phenyl}propanoic acid are obtained in the form of a white solid.

$^1$H NMR (d CDCl$_3$): 0.92 (t, J=7.3 Hz, 3H); 1.21 (t, J=7.0 Hz, 3H); 1.35-1.45 (m, 2H); 1.57-1.64 (m, 2H); 3.11 (dd, J=8.0 Hz, J=14.1 Hz, 1H); 3.22 (dd, J=4.0 Hz, J=14.1 Hz, 1H); 3.41 (q, J=6.9 Hz, 2H); 3.47 (s, 3H); 3.48-3.50 (m, 1H): 3.67-3.71 (m, 1H); 4.15 (dd, J=4.1 Hz; J=8.0 Hz, 1H); 6.94 (d, J=8.4 Hz, 1H); 7.36-7.41 (m, 3H); 7.75-7.82 (m, 3H); 10.5 (s, 1H).

EXAMPLE 26

Synthesis of 2(S)-Ethoxy-3-{4-[6-(1-methyl-3-phenethylureido)pyrid-2-yl]phenyl}propanoic acid hydrochloride (a) Preparation of Methyl 2(S)-ethoxy-3-{4-[6-(1-methyl-3-phenethylureido)pyrid-2-yl] phenyl}propanoate In a manner similar to that of Example 24(a), starting with 0.63 g (1.1 mmol) of methyl 2(S)-ethoxy-3-[4-(6-methylaminopyrid-2-yl)phenyl]propanoate, 0.4 g (83%) of methyl 2(S)-ethoxy-3-{4-[6-(1-methyl-3-phenethylureido)pyrid-2-yl] phenyl}propanoate is obtained.

(b) Preparation of 2(S)-Ethoxy-3-{4-[6-(1-methyl-3-phenethylureido)pyrid-2-yl]phenyl}propanoic acid In a manner similar to that of Example 20(i), starting with 0.4 g (0.8 mmol) of methyl 2(S)-ethoxy-3-{4-[6-(1-methyl-3-phenethylureido)pyrid-2-yl]phenyl}propanoate, 300 mg (85%) of 2(S)-ethoxy-3-{4-[6-(1-methyl-3-phenethylureido) pyrid-2-yl]phenyl}propanoic acid are obtained.

(c) Synthesis of 2(S)-Ethoxy-3-{4-[6-(1-methyl-3-phenethylureido)pyrid-2-yl]phenyl}propanoic acid hydrochloride In a manner similar to that of Example 10, starting with 300 mg of 2(S)-ethoxy-3-{4-[6-(1-methyl-3-phenethylureido) pyrid-2-yl]phenyl}propanoic acid, 200 mg of 2(S)-ethoxy-3-{4-[6-(1-methyl-3-phenethylureido)pyrid-2-yl] phenyl}propanoic acid hydrochloride are obtained in the form of a white solid.

$^1$H NMR (δ CDCl$_3$): 1.10 (t, J=6.7 Hz, 3H); 2.85 (m, 2H); 2.94-3.04 (m, 1H); 3.10-3.13 (m, 1H); 3.31 (m, 1H); 3.60 (s, 3H); 3.62 (m, 2H); 3.66 (m, 1H); 3.98 (m, 1H); 7.09 (m, 1H); 7.19 (m, 5H); 7.38 (m, 3H); 7.59 (m, 2H); 7.97 (m, 1H).

EXAMPLE 27

Synthesis of 2(S)-Ethoxy-3-{4-[6-(1-methyl-3-phenylureido)pyrid-2-yl]phenyl}propanoic acid

(a) Preparation of Methyl 2(S)-ethoxy-3-{4-[6-(1-methyl-3-phenylureido)pyrid-2-yl]phenyl}propanoate In a manner similar to that of Example 24(a), starting with 0.63 g (1.1 mmol) of methyl 2(S)-ethoxy-3-[4-(6-methylaminopyrid-2-yl)phenyl]propanoate, 0.16 g (37%) of methyl 2(S)-ethoxy-3-{4-[6-(1-methyl-3-phenylureido)pyrid-2-yl]phenyl}propanoate is obtained.

(b) Synthesis of 2(S)-Ethoxy-3-{4-[6-(1-methyl-3-phenylureido)pyrid-2-yl]phenyl}propanoic acid In a manner similar to that of Example 20(i), starting with 0.16 g (0.8 mmol) of methyl 2(S)-ethoxy-3-{4-[6-(1-methyl-3-phenylureido)pyrid-2-yl]phenyl}propanoate, 120 mg (92%) of 2(S)-ethoxy-3-{4-[6-(1-methyl-3-phenylureido)pyrid-2-yl]phenyl}propanoic acid are obtained.

$^1$H NMR (d CDCl$_3$): 1.08 (t, J=7.0 Hz, 3H); 2.97 (dd, J=8.6 Hz, J=14 Hz, 1H); 3.09 (dd, J=4.1 Hz, J=14.0 Hz, 1H); 3.28-3.32 (m, 1H); 3.44 (s, 3H); 3.59-3.64 (m, 1H); 3.97 (dd, J=4.6 Hz, J=8.5 Hz, 1H); 6.94 (t, J=7.4 Hz, 1H); 7.00 (d, J=8.4 Hz, 1H); 7.18-7.22 (m, 2H); 7.37-7.39 (m, 3H); 7.43-7.45 (m, 2H); 7.78-7.82 (m, 3H); 13.00 (s, 1H).

EXAMPLE 28

Synthesis of 2(S)-Ethoxy-3-{4-[6-(1-methyl-3-naphthalen-2-ylureido)pyrid-2-yl]phenyl}propanoic acid

(a) Preparation of Methyl 2(S)-ethoxy-3-{4-[6-(1-methyl-3-naphthalen-2-ylureido)pyrid-2-yl]phenyl}propanoate In a manner similar to that of Example 7(i), starting with 0.4 g (0.8 mmol) of methyl 2(S)-ethoxy-3-[4-(6-methylaminopyrid-2-yl)phenyl]propanoate and 2-naphthyl isocyanate, 0.2 g (62%) of methyl 2(S)-ethoxy-3-{4-[6-(1-methyl-3-naphthalen-2-ylureido)pyrid-2-yl]phenyl}propionate is obtained.

(b) Synthesis of 2(S)-Ethoxy-3-{4-[6-(1-methyl-3-naphthalen-2-ylureido)pyrid-2-yl]phenyl}propanoic acid In a manner similar to that of Example 20(i), starting with 0.2 g (0.5 mmol) of methyl 2(S)-ethoxy-3-{4-[6-(1-methyl-3-naphthalen-2-ylureido)pyrid-2-yl]phenyl}propanoate, 0.15 g (95%) of 2(S)-ethoxy-3-{4-[6-(1-methyl-3-naphthalen-2-ylureido)pyrid-2-yl]phenyl}propanoic acid is obtained.

$^1$H NMR (d CDCl$_3$): 1.23 (t, J=7.0 Hz, 3H); 3.16 (dd, J=7.6 Hz, J=14.1 Hz, 1H); 3.28 (dd, J=4.3 Hz, J=14.1 Hz, 1H); 3.52-3.56 (m, 1H); 3.58 (s, 3H); 3.68-3.72 (m, 1H); 4.21 (dd, J=4.3 Hz, J=7.6 Hz, 1H); 7.04 (d, J=8.4 Hz, 1H); 7.28 (m, 1H); 7.37-7.51 (m, 5H); 7.75-7.84 (m, 4H); 7.92 (d, J=8.2 Hz, 2H); 8.25 (d, J=1.7 Hz, 1H); 13.30 (s, 1H).

EXAMPLE 29

Crossover-Curve PPAR Transactivation Test

The activation of PPAR receptors with an agonist (activator) in HeLN cells leads to the expression of a reporter gene, luciferase, which, in the presence of a substrate, generates light. The modulation of the PPAR receptors is measured by quantifying the luminescence produced after incubating the cells in the presence of a reference agonist. The ligands displace the agonist from its site. The measurement of the activity is performed by quantifying the light produced. This measurement makes it possible to determine the modulatory activity of the compounds according to the invention by determining the constant that represents the affinity of the molecule for the PPAR receptor. Since this value can fluctuate depending on the basal activity and the expression of the receptor, it is referred to as Kd apparent (KdApp in nM).

To determine this constant, "crossover curves" of the test product against a reference agonist are performed in a 96-well plate: 10 concentrations of the test product plus a concentration 0 are arranged in a line, and 7 concentrations of the agonist plus a concentration 0 are arranged in a column. This represents 88 measurement points for 1 product and 1 receptor. The remaining 8 wells are used for repeatability controls.

In each well, the cells are in contact with a concentration of the test product and a concentration of the reference agonist, 2-(4-{2-[3-(2,4-difluorophenyl)-1-heptylureido]ethyl}phenylsulfanyl)-2-methylpropionic acid for PPARα, {2-methyl-4-[4-methyl-2-(4-trifluoromethylphenyl)thiazol-5-ylmethylsulfanyl]phenoxy}acetic acid for PPARδ and 5-{4-[2-(methylpyrid-2-ylamino)ethoxy]benzyl}thiazolidine-2,4-dione for PPARγ. Measurements are also taken for total agonist controls with the same products.

The HeLN cell lines used are stable transfectants containing the plasmids ERE-βGlob-Luc-SV-Neo (reporter gene) and PPAR (α, δ, γ) Gal-hPPAR. These cells are inoculated into 96-well plates at a rate of 10 000 cells per well in 100 μl of DMEM medium without phenol red and supplemented with 10% of defatted calf serum. The plates are then incubated at 37° C. and 7% CO$_2$ for 16 hours.

The various dilutions of the test products and of the reference ligand are added at a rate of 5 μl per well. The plates are then incubated for 18 hours at 37° C. and 7% CO$_2$. The culture medium is removed by turning over and 100 μl of a 1:1 PBS/luciferine mixture are added to each well. After 5 minutes, the plates are read by the luminescence detector.

These crossed curves make it possible to determine the AC50 values (concentration at which 50% activation is observed) of the reference ligand at various concentrations of test product. These AC50 values are used to calculate the Schild regression by plotting a straight line corresponding to the Schild equation ("quantitation in receptor pharmacology" Terry P. Kenakin, *Receptors and Channels,* 2001, 7, 371-385) which allows the Kd app values (in nM) to be obtained.

Transactivation Results:

| Compounds | PPARα Kd app (nM) | PPARδ Kd app (in nM) | PPARγ Kd app (in nM) |
|---|---|---|---|
| Reference 1: 2-(4-{2-[3-(2,4-difluorophenyl)-1-heptylureido]ethyl}phenyl sulfanyl)-2-methylpropionic acid | 200 | n.a. | n.a. |
| Reference 2: {2-methyl-4-[4-methyl-2-(4-trifluoromethylphenyl)thiazol-5-ylmethylsulfanyl]phenoxy}acetic acid | n.a. | 10 | n.a. |
| Reference 3: 5-{4-[2-(methylpyrid-2-ylamino)ethoxyl]benzyl}thiazolidine-2,4-dione | n.a. | n.a. | 30 |
| Example 1 | n.a. | n.a. | 4000 |
| Example 2 | n.a. | n.a. | 4000 |
| Example 3 | n.a. | n.a. | 4000 |
| Example 4 | n.a. | n.a. | 500 |
| Example 5 | 4000 | n.a. | 0.06 |
| Example 6 | 1000 | n.a. | 2 |
| Example 7 | 2000 | n.a. | 60 |
| Example 8 | n.a. | n.a. | 30 |
| Example 10 | 120 | n.a. | 0.5 |
| Example 15 | 2000 | n.a. | 1000 |
| Example 20 | n.a. | n.a. | 4 | n.a. means not active

These results show the affinity of the compounds for PPAR-γ and more particularly the specificity of the affinity of the compounds of the invention for the PPARγ subtype, compared with the affinity of the compounds for the PPARα subtype or for the PPARγ subtype.

EXAMPLE 30

Compositions

Various specific formulations based on the compounds according to the invention are illustrated in this example.

A - ORAL ROUTE:
(a) 0.2 g tablet:

| | |
|---|---|
| Compound of Example 2 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml ampules:

| | |
|---|---|
| Compound of Example 4 | 0.001 g |
| Glycerol | 0.500 g |
| 70% Sorbitol | 0.500 g |
| Sodium saccharinate | 0.010 g |
| Methyl para-hydroxybenzoate | 0.040 g |
| Flavoring | qs |
| Purified water | qs 5 ml |

(c) 0.8 g tablet:

| | |
|---|---|
| Compound of Example 1 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable suspension in 10 ml ampules:

| | |
|---|---|
| Compound of Example 10 | 0.200 g |
| Glycerol | 1.000 g |
| 70% Sorbitol | 1.000 g |
| Sodium saccharinate | 0.010 g |
| Methyl para-hydroxybenzoate | 0.080 g |
| Flavoring | qs |
| Purified water | qs 10 ml |

B - TOPICAL ROUTE:
(a) Ointment:

| | |
|---|---|
| Compound of Example 8 | 0.020 g |
| Isopropyl myristate | 81.700 g |
| Liquid petroleum jelly fluid | 9.100 g |
| Silica ("Aerosil 200" marketed by Degussa) | 9.180 g |

(b) Ointment:

| | |
|---|---|
| Compound of Example 7 | 0.300 g |
| White petroleum jelly codex | qs 100 g |

(c) Nonionic water-in-oil cream:

| | |
|---|---|
| Compound of Example 11 | 0.100 g |
| Mixture of emulsifying lanolin alcohols, waxes and oils ("Anhydrous Eucerin" marketed by BDF) | 39.900 g |
| Methyl para-hydroxybenzoate | 0.075 g |
| Propyl para-hydroxybenzoate | 0.075 g |
| Sterile demineralized water | qs 100 g |

(d) Lotion:

| | |
|---|---|
| Compound of Example 6 | 0.100 g |
| Polyethylene glycol (PEG 400) | 69.900 g |
| 95% Ethanol | 30.000 g |

(e) Hydrophobic ointment:

| | |
|---|---|
| Compound of Example 15 | 0.300 g |
| Isopropyl myristate | 36.400 g |
| Silicone oil ("Rhodorsil 47 V 300" marketed by Rhone-Poulenc) | 36.400 g |
| Beeswax | 13.600 g |
| Silicone oil ("Abil 300,000 cst" marketed by Goldschmidt) | qs 100 g |

(f) Nonionic oil-in-water cream:

| | |
|---|---|
| Compound of Example 9 | 1.000 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound having the following structural formula (I):

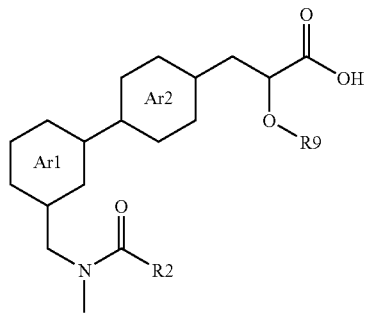

in which:
- R2 is an alkyl radical having from 1 to 12 carbon atoms, an aryl radical, an aralkyl radical, a heteroaryl radical, a heterocyclic radical, a 9-fluorenylmethyl radical or a radical of formula $(CH_2)_m(NR5)_n(C(O,N))_pR6$;
- R5, R6, m, n and p are as defined below;
- R5 is a hydrogen atom, an alkyl radical having from 1 to 12 carbon atoms, an aryl radical, an aralkyl radical, a heteroaryl radical or a heterocyclic radical,
- R6 is:
  a radical $O—(CH_2)_v—R10$,
  a hydroxyl radical, an alkyl radical having from 1 to 12 carbon atoms, an aryl radical, an aralkyl radical, a heteroaryl radical, a heterocyclic radical,
  a radical

or a radical $NR'(CH_2)_vR10$;
where R10, R', R" and v are as defined below;
- R9 is an alkyl radical having from 1 to 12 carbon atoms, or a radical selected from the group consisting of those of the following formulae:

(i)

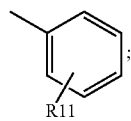

(ii) $—CO-(Q)_p—R11$; and
(iii) α-amino acid N-protected with standard amine-protecting groups;
where R11, Q and p are as defined below;
m has the value 0, 1 or 2;
n and p have the value 0 or 1;
v has the value 1, 2 or 3;
Q is an oxygen or sulfur atom or NR5;
R10 is an alkyl radical having from 1 to 12 carbon atoms, an aryl, aralkyl, heteroaryl or heterocyclic radical, a radical NH—CO—R12, a radical NH—CO—O—R12 or C—R12R13 or a radical N—R12R13, wherein R12 and R13 are as defined below;

- R' is a hydrogen atom, an alkyl radical having from 1 to 12 carbon atoms, a heteroaryl radical or a heterocyclic radical;
- R" is a hydrogen atom, an alkyl radical having from 1 to 12 carbon atoms, an aryl radical, an aralkyl radical, optionally substituted with one or more halogens, a heteroaryl radical, a heterocyclic radical, a radical $(CH_2)_v—R10$, or a radical NHR10 or NR10R10;
- R11 is a hydrogen atom, an alkyl radical having from 1 to 12 carbon atoms, an aryl radical, an aralkyl radical, a heteroaryl radical, a heterocyclic radical or a radical $(CO)_s(Z)_tR10$ with s and t having the values 0, 1 or 2;
- R12 is a hydrogen atom, an alkyl radical having from 1 to 12 carbon atoms, an aryl radical, an aralkyl radical, a heteroaryl radical or a heterocyclic radical;
- R13 is a hydrogen atom or an alkyl radical having from 1 to 12 carbon atoms;
- Z is an oxygen, nitrogen or sulfur atom;
- Ar1 and Ar2, which may be identical or different, are each an optionally substituted aromatic radical of one of the formulae:

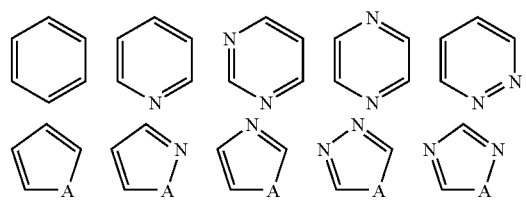

wherein A is an S or O atom or a radical N—R13, with the proviso that, when Ar1 or Ar2 is a

radical, then Ar2 or Ar1 is not a

radical, or an optical or geometrical isomer or salt thereof.

2. A compound as defined by claim 1, wherein in formula (I), Ar1 and Ar2, which may be identical or different, are each one of the unsubstituted radicals:

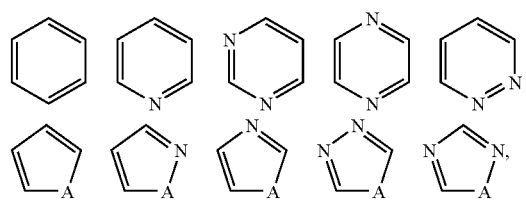

with the proviso that, when Ar1 or Ar2 is a

radical, then Ar2 or Ar1 is not a

radical.

3. A compound as defined by claim 1, in the form of a carboxylic acid salt, an organic amine salt or a salt of an amine function.

4. A compound as defined by claim 3, in the form of an alkali metal or alkaline-earth metal salt, an amino acid salt, a salt of a halogen atom or an organic acid or nitrate salt.

5. A compound as defined by claim 1, comprising at least one linear or cyclic, saturated or unsaturated, optionally branched, hydrogen-containing or fluorine-containing alkyl radical having 1 to 12 carbon atoms, which may be interrupted with a hetero atom.

6. A compound as defined by claim 1, comprising at least one phenyl, biphenyl, cinnamyl or naphthyl radical, which may be mono- or disubstituted with a halogen atom, a $CF_3$ radical, an alkyl radical having from 1 to 12 carbon atoms, an alkoxy radical having from 1 to 7 carbon atoms, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

7. A compound as defined by claim 1, comprising at least one benzyl, phenethyl or 2-naphthylmethyl radical, which may be mono- or disubstituted with a halogen atom, a $CF_3$ radical, an alkyl radical having from 1 to 12 carbon atoms, an alkoxy radical having from 1 to 7 carbon atoms, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

8. A compound as defined by claim 1, comprising at least one pyridyl, furyl, thienyl, isoxazolyl, oxadiazolyl, oxazolyl, isothiazolyl, quinazolinyl, benzothiadiazolyl, benzimidazolyl, quinoxalyl, indolyl or benzofuryl radical, optionally substituted with at least one halogen, an alkyl radical having from 1 to 12 carbon atoms, an alkoxy radical having from 1 to 7 carbon atoms, an aryl radical, a nitro function, a polyether radical, a heteroaryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl radical having from 1 to 12 carbon atoms.

9. A compound as defined by claim 1, comprising at least one morpholino, piperidino, piperazino, 2-oxo-1-piperidyl or 2-oxo-1- pyrrolidinyl radical, optionally substituted with at least one alkyl radical having from 1 to 12 carbon atoms, an alkoxy radical having from 1 to 7 carbon atoms, an aryl radical, a nitro function, a polyether radical, a heteroaryl radical, a benzoyl radical, an alkyl ester group, a carboxylic acid, a hydroxyl optionally protected with an acetyl or benzoyl group or an amino function optionally protected with an acetyl or benzoyl group or optionally substituted with at least one alkyl radical having from 1 to 12 carbon atoms.

10. A compound as defined by claim 1, comprising at least one halogen atom selected from the group consisting of a fluorine atom, a chlorine atom and a bromine atom.

11. The compound as defined by claim 1, which is selected from the group consisting of:

2(S)-Ethoxy-3-(4-{5-[(methyloctanoylamino)methyl]thiophen-3-yl }phenyl)propanoic acid, 2(S)-Ethoxy-3-(4-{5-[(methyloctanoylamino)methyl]thiophen-2-yl }phenyl)propanoic acid, 2(S)-Ethoxy-3-(4-{5-[(hexanoylmethylamino)-methyl]thiophen-3-yl }phenyl)propanoic acid, 2(S)-Ethoxy-3-(4-{5-[(methylpentanoylamino)methyl]thiophen-3-yl }phenyl)propanoic acid, 3-[4-(5-{[(2-Cyclopentylacetyl)methylamino]methyl}thiophen-3-yl)phenyl]-2(S)-ethoxypropanoic acid, 3-[4-(5-{[(3-Cyclohexylpropionyl)methylamino]methyl}thiophen-3-yl)phenyl]-2(S)-ethoxypropanoic acid, 2(S)-Ethoxy-3-[4-(5-{[methyl(6-propoxynaphthalene-2-carbonyl)amino]methyl }furan-2-yl)phenyl]propanoic acid, 2(S)-Ethoxy-3-[4-(5-{[methyl(6-propoxynaphthalene-2-carbonyl) amino]methyl}thiophen-2-yl)phenyl]propanoic acid, 2(S)-Ethoxy-3-[4-(4-{[methyl(6-propoxynaphthalene-2-carbonyl) amino]methyl}thiophen-2-yl)phenyl]propanoic acid, 2(S)-Ethoxy-3-[6-(3-{[methyl-(6-propoxynaphthalene-2-carbonyl) amino]methyl}phenyl)pyrid-3-yl]propanoic acid, 2(S)-Ethoxy-3-(6-{3-[(heptanoylmethylamino)methyl]phenyl}pyrid-3-yl) propanoic acid, 2(S)-Ethoxy-3-(6-{3-[(hexanoylmethylamino)methyl]phenyl}pyrid-3-yl) propanoic acid, 2(S)-Ethoxy-3-(4-{5-[(methyloctanoylamino)methyl]furan-2-yl}phenyl) propanoic acid, 2(S)-Ethoxy-3-(4-{5-[(hexanoylmethylamino)methyl]thiophen-3-yl}phenyl) propanoic acid, 2(S)-Ethoxy-3-(6-{5-[(methyloctanoylamino)methyl]thiophen-3-yl}pyrid-3-yl) propanoic acid, 2(S)-Ethoxy-3-(6-{5-[(hexanoylmethylamino)methyl]thiophen-3-yl}pyrid-3-yl) propanoic acid, and 2(S)-Ethoxy-3-[4-(5-{[(3-1H-indol-3-ylpropionyl)methylamino]methyl}thiophen-3-yl) phenyl]propanoic acid.

12. A compound as defined by claim 1, having at least one of the following characteristics:

R9 is an alkyl radical or a radical of formula (i) with R11 being a hydrogen or a group COOR10;

R2 is an alkyl, aryl or heteroaryl radical;

at least one of Ar1 and Ar2 is a pyridine, thiazole, pyrimidine, thiophene or triazole radical.

13. A compound as defined by claim 1, wherein in formula (I), Ar1 and Ar2, which may be identical or different, are each an optionally substituted aromatic radical of one of the formulae:

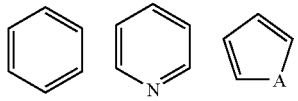

with the proviso that when Ar1 or Ar2 is a

radical, then Ar2 or Ar1 is not a

radical.

14. A compound as defined by claim 13, wherein A is an S or O atom.

15. A compound as defined by claim 1, wherein in formula (I), Ar1 and Ar2, which may be identical or different, are each an optionally substituted aromatic radical of one of the formulae:

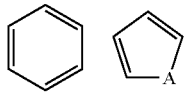

wherein A is an S or O atom, with the proviso than when Ar1 or Ar2 is a

radical, then Ar2 or Ar1 is not a

radical.

16. A compound as defined by claim 1, wherein in formula (I), Ar1 and Ar2, which may be the same or different, are each an optionally substituted aromatic radical of one of the formulae:

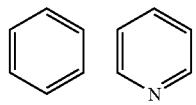

with the proviso that when Ar1 or Ar2 is a

radical, then Ar2 or Ar1 is not a

radical.

17. A compound as defined by claim 12, wherein R9 is an alkyl radical.

18. A compound as defined by claim 17, wherein R9 is ethyl.

19. A compound as defined by claim 1, wherein R2 is an alkyl, aryl or aralkyl radical.

20. A compound as defined by claim 19, wherein R2 is an aryl radical.

21. The compound as defined by claim 1, which is selected from the group consisting of:
2(S)-Ethoxy-3-[4-(5-{[methyl(6-propoxynaphthalene-2-carbonyl)amino]methyl }furan-2-yl)phenyl]propanoic acid,
2(S)-Ethoxy-3-[4-(5-{[methyl(6-propoxynaphthalene-2-carbonyl)amino]methyl }thiophen-2-yl)phenyl]propanoic acid,
2(S)-Ethoxy-3-[4-(4-{[methyl(6-propoxynaphthalene-2-carbonyl)amino]methyl}thiophen-2-yl) phenyl]propanoic acid,
2(S)-Ethoxy-3-[6-(3-{[methyl-(6-propoxynaphthalene-2-carbonyl) amino]methyl}phenyl)pyrid-3-yl]propanoic acid,
2(S)-Ethoxy-3-(6-{3-[(heptanoylmethylamino)methyl] phenyl}pyrid-3-yl)propanoic acid,
2(S)-Ethoxy-3-(6-{3-[(hexanoylmethylamino)methyl] phenyl}pyrid-3-yl)propanoic acid, and
2(S)-Ethoxy-3-(4-{5-[(methyloctanoylamino)methyl]furan-2-yl}phenyl)propanoic acid.

22. The compound as defined by claim 1, which is selected from the group consisting of:
2(S)-Ethoxy-3-[4-(5-{[methyl(6-propoxynaphthalene-2-carbonyl)amino]methyl}furan-2-yl)phenyl]propanoic acid,
2(S)-Ethoxy-3-[4-(5-{[methyl(6-propoxynaphthalene-2-carbonyl) amino]methyl}thiophen-2-yl)phenyl]propanoic acid,
2(S)-Ethoxy-3-[4-(4-{[methyl(6-propoxynaphthalene-2-carbonyl) amino]methyl}thiophen-2-yl)phenyl]propanoic acid, and 2(S)-Ethoxy-3-(4-{5-[(methyloctanoylamino)methyl]furan-2-yl}phenyl)propanoic acid.

23. The compound as defined by claim 15, which is selected from the group consisting of:
  2(S)-Ethoxy-3-(4-{5-[(methyloctanoylamino)methyl]thiophen-3-yl}phenyl)propanoic acid,
  2(S)-Ethoxy-3-(4-{5-[(methyloctanoylamino)methyl]thiophen-2-yl}phenyl)propanoic acid,
  2(S)-Ethoxy-3-(4-{5-[(hexanoylmethylaminoymethyl]thiophen-3-yl}phenyl)propanoic acid,
  2(S)-Ethoxy-3-(4-{5-[(methylpentanoylamino)methyl]thiophen-3-yl}phenyl)propanoic acid,
  3-[4-(5-{[(2-Cyclopentylacetyl)methylamino]methyl}thiophen-3-yl)phenyl]-2(S)-ethoxypropanoic acid,
  3-[4-(5-{[(3-Cyclohexylpropionyl)methylamino]methyl}thiophen-3-yl)phenyl]-2(S)-ethoxypropanoic acid,
  2(S)-Ethoxy-3-[4-(5-{[methyl(6-propoxynaphthalene-2-carbonyl) amino]methyl}furan-2-yl)phenyl]propanoic acid,
  2(S)-Ethoxy-3-[4-(5-{[methyl(6-propoxynaphthalene-2-carbonyl) amino]methyl}thiophen-2-yl)phenyl]propanoic acid,
  2(S)-Ethoxy-3-[4-(4-{[methyl(6-propoxynaphthalene-2-carbonyl) amino]methyl}thiophen-2-yl)phenyl]propanoic acid,
  2(S)-Ethoxy-3-(4-{5-[(methyloctanoylamino)methyl]furan-2-yl}phenyl)propanoic acid,
  2(S)-Ethoxy-3-(4-{5-[(hexanoylmethylamino)methyl]thiophen-3-yl}phenyl)propanoic acid, and
  2(S)-Ethoxy-3-[4-(5-{[(3-1H-indol-3-ylpropionyl)methylamino]methyl}thiophen-3-yl) phenyl]propanoic acid.

24. A cosmetic composition, comprising a cosmetically effective amount of at least one compound as defined in claim 1, formulated into a cosmetically/physiologically acceptable support therefor.

25. The cosmetic composition as defined by claim 24, said at least one compound comprising from 0.001% to 3% by weight thereof.

26. The cosmetic composition as defined by claim 24, formulated for body or hair hygiene.

27. A pharmaceutical composition, comprising a pharmaceutically effective amount of at least one compound as defined in claim 1, formulated into a pharmaceutically/physiologically acceptable support therefor.

28. The pharmaceutical composition as defined in claim 27, said at least one compound comprising from 0.001% to 10% by weight thereof.

29. A method for the activation of receptors of PPARγ, comprising contacting said receptors with an effective PPARγ receptor-activating amount of a compound having formula (I) as defined by claim 1.

30. A method of treating common acne, comedones, polymorphous acne, nodulocystic acne, acne conglobata, senile acne, or secondary acne, comprising administering to an individual in need of such treatment an effective amount of a compound having formula (I) as defined by claim 1.

31. The compound of claim 23, which is 2(S)-ethoxy-3-(4-{5-[(methyloctanoylamino)methyl]thiophen-3-yl}phenyl)propanoic acid.

* * * * *